US012709634B2

(12) United States Patent
Buschow et al.

(10) Patent No.: US 12,709,634 B2
(45) Date of Patent: Aug. 18, 2026

(54) TREATMENT OF DISEASES RELATED TO HEPATITIS B VIRUS

(71) Applicants: ISABELLA PHARMA B.V., Haarlem (NL); ERASMUS UNIVERSITY MEDICAL CENTER ROTTERDAM, Rotterdam (NL)

(72) Inventors: Sonja Ingrid Buschow, Utrecht (NL); Monica Theodora Antonetta de Beijer, Rotterdam (NL); Miranda Bernardina Johanna Molenaar, Maarssen (NL); Thomas Johannes Maria Beenakker, Leiden (NL); Wilhelmus Johannes Theodorus Alexander Krebber, Leiden (NL); Cornelis Johannes Maria Melief, Haarlem (NL); Anna-Sophia Wiekmeijer, Oegstgeest (NL); Peter van Rijn, Leiden (NL); Diahann Talia Satirah Ludovica Jansen, Leiden (NL); Wilhelmus Johannes Elizabeth van Esch, Purmerend (NL)

(73) Assignees: ISABELLA PHARMA B.V., Haarlem (NL); ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 1031 days.

(21) Appl. No.: 17/779,564

(22) PCT Filed: Dec. 4, 2020

(86) PCT No.: PCT/EP2020/084636

§ 371 (c)(1),
(2) Date: May 25, 2022

(87) PCT Pub. No.: WO2021/110919

PCT Pub. Date: Jun. 10, 2021

(65) Prior Publication Data

US 2023/0242590 A1 Aug. 3, 2023

(30) Foreign Application Priority Data

Dec. 7, 2019 (EP) .................................... 19214315

(51) Int. Cl.

| | |
|---|---|
| ***C07K 16/28*** | (2006.01) |
| ***A61K 39/29*** | (2006.01) |
| ***A61P 31/20*** | (2006.01) |
| ***C07K 14/005*** | (2006.01) |
| ***C12N 5/078*** | (2010.01) |
| *A61K 39/00* | (2006.01) |

(52) U.S. Cl.

CPC .......... *C07K 14/005* (2013.01); *A61K 39/292* (2013.01); *A61P 31/20* (2018.01); *A61K 2039/51* (2013.01); *C12N 2730/10121* (2013.01); *C12N 2730/10134* (2013.01)

(58) Field of Classification Search

None

See application file for complete search history.

(56) References Cited

U.S. PATENT DOCUMENTS

| | | | | |
|---|---|---|---|---|
| 6,689,363 | B1 * | 2/2004 | Sette | C07K 14/705 530/324 |
| 9,340,577 | B2 * | 5/2016 | Grey | A61K 39/02 |
| 10,300,132 | B2 * | 5/2019 | Georges | A61K 45/06 |
| 10,898,567 | B2 * | 1/2021 | Krebber | A61K 39/292 |
| 2006/0051746 | A1 | 3/2006 | Chisari | |

FOREIGN PATENT DOCUMENTS

| | | | |
|---|---|---|---|
| CN | 108239657 | A | 7/2018 |
| JP | 2022-534243 | A | 7/2022 |
| WO | 98/21317 | A1 | 5/1998 |
| WO | 0219986 | A1 | 3/2002 |
| WO | 2007/110098 | A1 | 10/2007 |
| WO | 2014/102540 | A1 | 7/2014 |
| WO | 2015/187009 | A1 | 12/2015 |

OTHER PUBLICATIONS

Kadowaki M. et al., "Immunochemical study on hepatitis B virus (HBV) gene products with use of synthetic peptides—chemical synthesis of HBVx-related peptides," 1985.

KR Office Action dated Sep. 23, 2025 as received in Application No. 10-2022-7023156.

Malmassari, S. et al: In vivo hierarchy of immunodominant and subdominant HLA-A*0201-restricted T-cell epitopes of HBx antigen of hepatitis B virus (Microbes and Infection 7 (2005) 626-634).

Zheng et al., "In Silico Analysis of Epitope-Based Vaccine Candidates against Hepatitis B Virus Polymerase Protein", VIRUSES, vol. 9, No. 5, Jan. 1, 2017 (Jan. 1, 2017), p. 112, XP055690912, CH ISSN: 1999-4915, DOI: 10.3390/v9050112.

Malmassari et al: "In vivo hierarchy of immunodominant and subdominant HLA-A*0201-restricted T-cell epitopes of HBx antigen of hepatitis B virus", Microbes and Infection, Elsevier, Paris, FR, vol. 7, No. 4, Apr. 1, 2005 (Apr. 1, 2005), pp. 626-634, XP027846055, ISSN: 1286-4579 [retrieved on Apr. 1, 2005].

* cited by examiner

*Primary Examiner* — Agnieszka Boesen

(74) *Attorney, Agent, or Firm* — Maschoff Brennan

(57) ABSTRACT

The invention provides novel immunogenic peptides derived from the X protein and polymerase protein of hepatitis B virus (HBV). The peptides contain epitopes that are well-conserved across multiple HBV variants and are derived from regions of proteins that are essential for viral replication. Moreover, the novel HBV antigens bind multiple HLA types and epitopes that elicit IFNγ responses in PBMCs from HBV resolvers have been identified.

7 Claims, 17 Drawing Sheets

Specification includes a Sequence Listing.

HBxAg

| | | |
|---|---|---|
| Reported HLA class I epitopes | | 99-108, 140-148, 15-23, 52-60, 91/2-100, 102-110, 135-143, 8-16, 44-53, 84-92, 97-106, 115-123, 133-141 |
| Predicted HLA-I binders (8-11 mers) | HLA*B08:01 | 58-66, 134-142, 52-60, 75-83, 91/2-100, 126-134/5, 1-9, 54-63, 67-76, 88/9-98, 125-134 |
| | HLA*B07:02 | 39-48, 63-71, 32-41, 49/0-58, 73-81, 100-108, 26-35, 37-46, 54-63, 67-75, 95-103, 24/5/6-34, 44/5-54, 58-67, 81-89, 101-110, 19-27, 37/8/9-47, 52-60, 52-60, 94-102/3, 144-152, 21/2-30, 35/6/7-45, 56/7/8-66, 70-79, 91/2-100, 132-141, 1-9, 28-36/8, 45-53/5, 75-83, 89-97/9, 146-154, 9/0-18, 27/8-37, 43/4-53, 66/7-76, 88/9-98, 126-134, 144-153/4 |
| | HLA*A24:02 | 110/1-120, 143-151 |
| | HLA*A03:01 | 81/2-91, 104-113, 130-138, 69/0-78, 85/6/7-95, 102-111, 130/1/2-140 |
| | HLA*A02:01 | 102-110, 15-23, 51/2-60, 99-108, 140-148, 8-16, 36-44/5, 63-71, 97-106, 133-142, 3/4-13, 28-37, 57-66, 91/2-100, 115-123, 132/3-141 |
| | HLA*A01:01 | 105-113, 104-112/3, 103-111/2/3, 63-71/3, 101/2-111 |

RNA binding

RNA binding

F

Polymerase 201-474

365-374 388/9-397 422-430

368/9-378

261-269 338-346 361-369 374-383 418-426 440-448 466-474

RNA binding

H

Polymerase 632-843

H

Newly identified cross-reactive peptides

| Peptide | Sequence | Reported for | Novel binder for |
|---|---|---|---|
| x52-60 | HLSLRGLPV | A*02:01 | B*08:01 |
| x92-100 | VLHKRTLGL | A*02:01 | B*08:01 |
| p166-175 | ASFCGSPYSW | B*58:01 | A*24:02 |
| p365-374 | TPARVTGGVF | B*35 / B*51 | B*07:02 |
| p500-508 | KLHLYSHPI | A*02:03 | B*08:01 |
| p549-557 | YMDDVVLGA | A*02:01 | A*01:01 |

TREATMENT OF DISEASES RELATED TO HEPATITIS B VIRUS

REFERENCE TO AN ELECTRONIC SEQUENCE LISTING

The contents of the electronic sequence listing (sequence-listing.txt; Size: 43.4 Kb; and Date of Creation: Oct. 13, 2022) is herein incorporated by reference in its entirety.

FIELD OF THE INVENTION

The present invention relates to the field of infectious diseases. In particular, it relates to immunogenic peptides, polynucleotides, immunogenic compositions and methods for treating diseases related to hepatitis B virus (HBV).

BACKGROUND OF THE INVENTION

Chronic infection with the hepatitis B virus (HBV) is a major global health problem. HBV is the prototype member of the Hepadnaviridae family, which have a strong preference for infecting liver cells (Ganem et al, 2004 N Engl J Med 350:1118).

Despite the availability since three decades of an efficacious preventive vaccine for the protection against hepatitis B, an estimated two billion people have nevertheless been infected with HBV and more than 240 million currently have chronic (long-term) hepatitis B infection, with a geographical predominance in regions outside Western Europe and North America (World Health Organization, July 2013).

Transmission of the virus between people occurs by direct blood-to-blood contact or via semen or vaginal fluid of an infected person. In endemic areas, the infection occurs characteristically by perinatal transmission from mother to child. Thus, although HBV is not transmitted casually, the virus can be easily transmitted by perinatal, percutaneous or sexual exposure. Frequent person-to-person contact with infected individuals accordingly poses a serious risk to groups such as health workers.

Infection with HBV can develop as an acute viral hepatitis, an illness that begins with general ill-health, loss of appetite, nausea, vomiting, body aches, mild fever, and dark urine, and then progresses to development of jaundice. The illness lasts for a few weeks and then gradually improves in most affected adults, although some people may have more severe liver disease (fulminant hepatic failure) which can cause death. The infection may be entirely asymptomatic and may go unrecognized.

Chronic infection with hepatitis B virus either may be asymptomatic or may be associated with a chronic inflammation of the liver (chronic hepatitis), leading to cirrhosis over a period of many years. This type of infection dramatically increases the incidence of hepatocellular carcinoma (liver cancer), also with a latency of many years. Treatment of chronically HBV-infected individuals with antiviral drugs such as nucleoside/nucleotide analogues (e.g. Entecavir and Tenofovir) or interferon (IFN)α efficiently decreases serum viral loads. However, antiviral therapy rarely leads to a sustained virological response and drug resistance occurs (Zoulim et al, 2012 B J Hepatol 56 suppl. 1 S112; EASL 2017 Clinical Practice Guidelines on the management of hepatitis B virus infection. J. Hepatology 67:370). Moreover, the great majority of HBV carriers remains untreated.

Approximately 15-40% of chronic HBV carriers will develop clinically significant liver disease in their lifetime with a high risk of death from liver cirrhosis and associated liver failure or hepatocellular carcinoma (Huang et al, 2011 Curr Opin Immunol 23:237). Due to the failure of antiviral drugs to eradicate infection, and consequently the need for long-term if not lifelong antiviral therapy with its drawbacks such as toxic side-effects and high costs, there is an urgent need for novel therapeutic approaches (Grimm et al., 2013 Clin Sci (Lond) 124:77).

Therapeutic vaccination constitutes a promising strategy to treat chronic hepatitis B. Next to the humoral immune response against HBV, which is predominantly involved in the protection against HBV infection by the current prophylactic vaccines (Lok, 2002 N Engl J Med 346:1682), the cellular immune response is unequivocally involved in the natural resistance against HBV infection.

Perinatal transmission of HBV from mothers to neonates and infections during the first years of life result in persistent infection in more than 90% of children. By contrast, infection during adulthood clears spontaneously in more than 90% of cases and results in lifelong protective immunity (Rehermann et al., 2005 Nat Rev Immunol 5:215).

In acute, self-limited hepatitis B virus infection, vigorous polyclonal and multispecific CD8+ cytotoxic T cell (CTL) and CD4+ T-helper (Th) cell responses to many HBV antigens are readily demonstrable in the peripheral blood (Michel et al, 2011 J Hepatol 54:1286).

These T cell responses are crucial in HBV clearance and control. Experiments in HBV-infected chimpanzees have shown the essential role of HBV-specific CD8+ T cells as effector cells in this process (Thimme et al, 2003 J Virol 77:68). In contrast to the response in patients with resolved HBV infections, in patients with chronic hepatitis B the T cell responses are usually very weak, focused on only a few epitopes and functionally impaired (Michel et al, 2011 J Hepatol 54:1286). The goal of therapeutic vaccination is to install vigorous and robust multivalent CTL and T-helper cell responses directed to many HBV antigens, thereby pursuing viral clearance, hepatitis control and cure.

Despite the fact that great progress has been made in understanding the etiology and epidemiology of the disease, there is still a need for an effective therapeutic HBV vaccine.

HBV-protein derived peptides that comprise presumed T cell epitopes restricted to specific HLA-types have been described in the art (WO0219986, WO2002020035, WO2014102540, WO15187009). However, many of these proposed antigens have one or more of the following drawbacks:

- Poor sequence conservation across HBV genotypes, resulting in efficacy against a (small) subset of HBV genotypes only,
- No functional link of the antigenic region they derive from to viral replication, reducing the probability that an immune response against this region will interfere with viral replication,
- Ineffective immune response because of immune exhaustion due to antigen overexposure,
- Collectively covering one or a few HLA types only, resulting in lack of efficacy in certain populations lacking these HLA types,
- Difficult to manufacture (in particular for longer peptides),
- No confirmed potential to induce a T cell response,
- No indication as to whether an immune response against the peptide antigen has the potential to resolve an infection.

SUMMARY OF THE INVENTION

The present invention provides novel long peptide antigens derived from the HBV-X and HBV polymerase proteins which resolve all or most of the disadvantages associated with previously-described peptide antigens.

The HBV long peptide antigens described herein contain novel HLA-binding peptide sequences that are well-conserved across multiple HBV genotypes, are derived from conserved regions of the proteins that are essential for viral replication and are therefore less likely to escape from HBV-specific immune responses. Moreover, the novel HBV-derived long peptide antigens harbor multiple HLA-binding peptide sequences which have the capacity to be presented by a diversity of HLA types. Furthermore, synthetic long peptides (SLPs) containing these HLA-binding peptide sequences that can be manufactured with sufficient yield and of sufficient purity are described. Moreover, SLPs that contain the newly identified HLA-binding peptide sequences have been found to elicit IFNγ responses in PBMCs from persons that have resolved HBV infection (HBV resolvers).

In a first main aspect, the invention relates to an immunogenic peptide comprising a fragment of an HBV protein, wherein said fragment is 20-34 amino acids in length and wherein said fragment comprises:

a) at least 10 consecutive amino acids of the region from position 57 to position 78 of HBV-X, preferably comprising:
   the amino acid sequence set forth in SEQ ID NO:1 (x70-78), and/or
   the amino acid sequence set forth in SEQ ID NO:2 (x67-75), and/or
   the amino acid sequence set forth in SEQ ID NO:3 (x62-73), and/or
   the amino acid sequence set forth in SEQ ID NO:4 (x58-66), and/or
   the amino acid sequence set forth in SEQ ID NO:5 (x57-66), or
b) at least 11 consecutive amino acids of the region from position 103 to position 120 of HBV-X, preferably comprising:
   the amino acid sequence set forth in SEQ ID NO:6 (x103-111), and/or
   the amino acid sequence set forth in SEQ ID NO:7 (x104-113), and/or
   the amino acid sequence set forth in SEQ ID NO:8 (x105-113), and/or
   the amino acid sequence set forth in SEQ ID NO:9 (x110-120), or
c) the amino acid sequence set forth in SEQ ID NO:10 (x132-140), or
d) the amino acid sequence set forth in SEQ ID NO:11 (p124-133), or
e) the amino acid sequence set forth in SEQ ID NO:12 (p164-173), or
f) the amino acid sequence set forth in SEQ ID NO:13 (p275-283), or
g) at least 10 consecutive amino acids of the region from position 403 to position 415 of HBV polymerase, preferably comprising:
   the amino acid sequence set forth in SEQ ID NO:14 (p403-412), and/or
   the amino acid sequence set forth in SEQ ID NO:15 (p404-412), and/or
   the amino acid sequence set forth in SEQ ID NO:16 (p407-415), or
h) at least 9 consecutive amino acids of the region from position 509 to position 523 of HBV polymerase, preferably comprising:
   the amino acid sequence set forth in SEQ ID NO:17 (p509-517), and/or
   the amino acid sequence set forth in SEQ ID NO:18 (p515-523), or
i) at least 10 consecutive amino acids of the region from position 649 to position 658 of HBV polymerase, comprising:
   the amino acid sequence set forth in SEQ ID NO:19 (p649-658), and/or
   the amino acid sequence set forth in SEQ ID NO:20 (p650-658), or
j) at least 10 consecutive amino acids of the region from position 693 to position 706 of HBV polymerase, preferably comprising:
   the amino acid sequence set forth in SEQ ID NO:21 (p693-701), and/or
   the amino acid sequence set forth in SEQ ID NO:22 (p697-706), or
k) the amino acid sequence set forth in SEQ ID NO:23 (p723-731), or
l) at least 10 consecutive amino acids of the region from position 755 to position 765 of HBV polymerase, comprising:
   the amino acid sequence set forth in SEQ ID NO:24 (p755-764), and/or
   the amino acid sequence set forth in SEQ ID NO:25 (p756-765), or
m) the amino acid sequence set forth in SEQ ID NO:26 (p829-837).

In further aspects, the invention relates to polynucleotides comprising a nucleotide sequence encoding a peptide according to the invention, to immunogenic compositions comprising immunogenic peptides or polynucleotides of the invention and to uses of peptides, polynucleotides, recombinant viruses or immunogenic compositions of the invention in the treatment of HBV related diseases.

DETAILED DESCRIPTION OF THE INVENTION

Definitions

Figure 1:
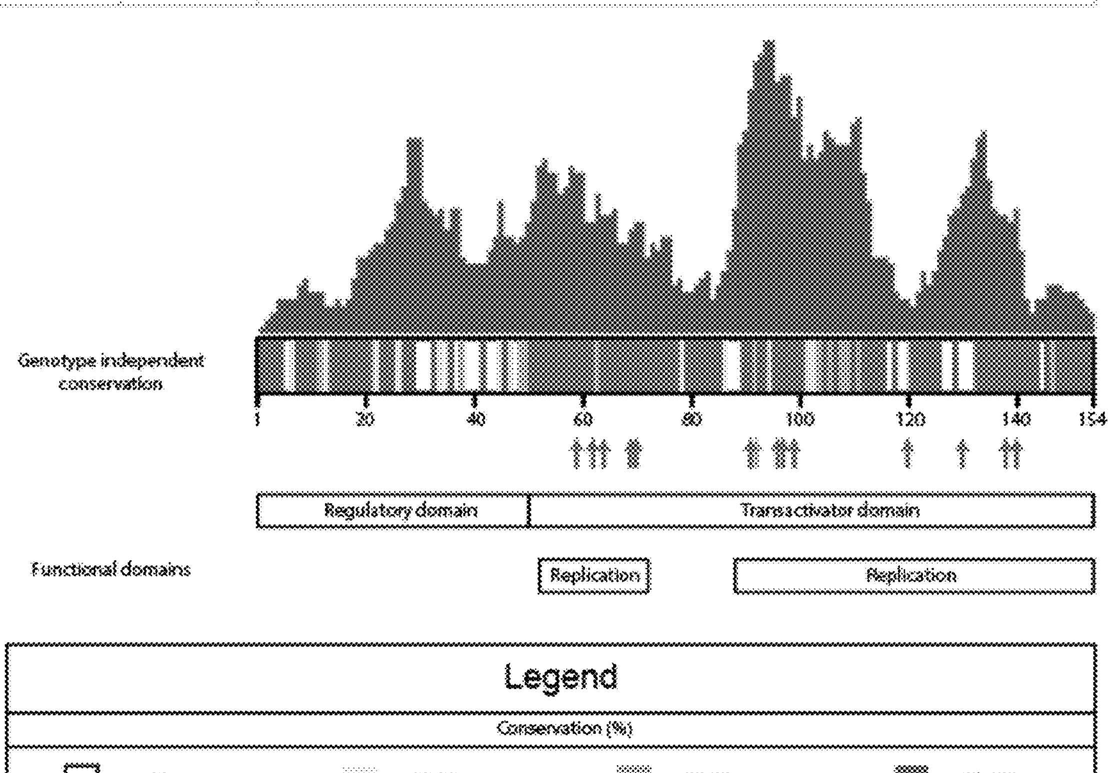
FIG. 1. Alignment of validated HLA-I epitopes and predicted HLA-binding peptide sequences to protein conservation and function for HBx. A centered bar diagram depicts the length of the consensus sequence of the HBx protein (methods) in which the conservation score across viral genotypes is indicated by a grey scale code (legend) for each amino acid. Reported validated epitope sequences obtained from the Hepitopes database are aligned to this consensus protein sequence and shown on top. Below this, potential novel binders predicted by NetMHCpan (9-11 amino acids), are depicted for each HLA-supertype representative. Below the aligned binders we plotted the frequency distribution of each amino acid within all predicted binders (8-14 amino acids in length) over the protein sequence. The conservation score (legend) of each amino acid is shown as a horizontal grey scale-coded bar diagram. Essential amino acids of which mutation leads to loss of viral persistence are indicated by arrows matching the color of the conservation score. Functional domains are depicted at the bottom according to the nomenclature of HBVdb.

The term "HBV" refers to hepatitis B virus. Eight different genotypes of HBV, termed A to H, have been described. The genotypes share significant sequence homology, but differ by at least 8% of the sequence. Within genotypes, subtypes have been described: these differ by 4-8% of the genome.

The terms "HBV polymerase" or simply "polymerase" or "Pol" refer to the polymerase encoded by the hepatis B genome. GenBank NCBI reference NC_003977.2 describes an HBV polymerase sequence that is commonly used as a reference, also set forth in SEQ ID NO:27 herein. SEQ ID NO:28 shows a consensus sequence of the HBV-polymerase based on 7489 genotypes. In one embodiment of the invention, the HBV polymerase fragment present in a peptide of the invention is more than 85%, such as more than 90%, e.g. more than 95%, such as more than 98% identical to the corresponding sequence set forth in SEQ ID NO:27. In another embodiment of the invention, the HBV polymerase fragment is more than 85%, such as more than 90%, e.g. more than 95%, such as more than 98% identical to the corresponding sequence set forth in SEQ ID NO:28. In another embodiment, the HBV polymerase referred to is of a genotype selected from the group consisting of A, B, C, D, E, F, G and H.

The terms "HBV-X", "HBx", "HBxAg", "HBV-X protein" or "X-protein" or the like refers to the X protein encoded by the hepatis B genome. GenBank NCBI reference NC_003977.2 describes an HBV-X sequence that is commonly used as a reference, also set forth in SEQ ID NO:29 herein. SEQ ID NO:30 shows a consensus sequences of the HBV-X protein based on 8127 genotypes. In one embodiment of the invention, the HBV-X fragment present in a peptide of the invention is more than 85%, such as more than 90%, e.g. more than 95%, such as more than 98% identical to the corresponding sequence set forth in SEQ ID NO:29. In another embodiment of the invention, the HBV-X fragment is more than 85%, such as more than 90%, e.g. more than 95%, such as more than 98% identical to the corresponding sequence set forth in SEQ ID NO:30. In another embodiment, the HBV-X protein referred to is of a genotype selected from the group consisting of A, B, C, D, E, F, G and H.

The numbering of the positions within HBV polymerase and HBV-X herein is with reference to the consensus sequences set forth in SEQ ID NO:28 and SEQ ID NO:30, respectively. In other words, the numbering of amino acid positions within HBV polymerase and HBV-X proteins corresponds to the numbering in the consensus sequences set forth in SEQ ID NO:28 and SEQ ID NO:30, respectively. An amino acid position in one sequence that "corresponds to" an amino acid position in another sequence is one that aligns with the other amino acid using a standard sequence alignment program such as ALIGN, ClustalW or similar, typically at default settings. It is considered well-known in the art how to align sequences and thereby determine, for a particular position in an HBV polymerase or HBV-X sequence, what the corresponding position in the consensus sequence is. For example, an alignment may show that a fragment from amino acid position 20 to position 40 in a given HBV polymerase corresponds to position 20 to 41 in the consensus sequence if there is a gap in the given HBV polymerase relative to the consensus sequence. For the avoidance of doubt: while the numbering of the positions is with reference to the consensus sequences, the actual amino-acid sequence of the fragment may differ from the consensus sequence and vary depending on the HBV genotype.

"Sequence identity" is herein defined as a relationship between two or more amino acid sequences, as determined by comparing the sequences. Sequence identity can be determined by alignment of two peptide sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman).

"Treatment" or "treating" refers to the administration of an effective amount of an immunogenic composition with the purpose of easing, ameliorating, arresting, eradicating (curing) or preventing symptoms, disorders or disease states. An "effective amount" refers to an amount effective, at dosages and for periods of time necessary, to achieve a desired therapeutic result.

When used herein, the term "immunogenic peptide" means a peptide capable of triggering or boosting an immune response. The immunogenic peptide of the invention may be unconjugated or unmodified, i.e. be a simple chain of amino acids linked by peptide bonds, or it may be further modified, e.g. conjugated, such as covalently bound to another molecule, e.g. an adjuvant.

Within the context of the present invention "20-34 amino acids in length" means that the number of amino acid residues is from 20 to 34, i.e. 20, 21, 22, 23, 24, 25, 26, 27, 28, 29, 30, 31, 32, 33 or 34 amino acid residues. Peptides of in the invention, also denominated as long peptides, exceed the length of human leukocyte antigen (HLA) class I and class II presented epitope peptide sequences. Preferably, the long peptides of the invention are synthetic peptides, also denominated herein as synthetic long peptides (SLPs).

Within the context of the present invention, the term "fragment of an HBV protein" means an amino acid sequence that corresponds to, i.e. is identical to, a partial sequence of an HBV protein. Thus, it refers to a consecutive sequence of a natural HBV protein without insertions, deletions or substitutions. If it is specified that a peptide comprises a fragment of an HBV protein of a certain length, it means that the fragment is not shorter or longer. For example, if it is specified that the fragment is 20-34 amino acids in length, this means that said fragment is not less than 20 amino acids or more than 34 amino acids in length. Thus, such a peptide does e.g. not comprise a consecutive sequence of said HBV protein of 35 amino acids in length or more. However, for the avoidance of doubt, "comprising" has its usual meaning in the art, i.e. a "peptide comprising a fragment of an HBV protein" can comprise additional sequences beyond the specified fragment, e.g. sequences not derived from said HBV protein or other partial sequences of an HBV protein which are not contiguous with said fragment in the HBV protein.

Within the context of the present invention, the terms "HLA-binding peptide" or "HLA binder" or "binder" refer to the short protein fragment part of HBV-X or HBV polymerase, that can specifically bind to an HLA molecule.

Within the context of the present invention, an "epitope" is defined as a short HLA-binding peptide bound to a specified HLA molecule, that when present on the surface of a cell, is capable of eliciting a T cell response in an individual.

Reference to an element by the indefinite article "a" or "an" does not exclude the possibility that more than one of the elements is present, unless the context clearly requires that there be one and only one of the elements. The indefinite article "a" or "an" thus usually means "at least one".

FURTHER ASPECTS AND EMBODIMENTS OF THE INVENTION

As mentioned above, in a first main aspect, the invention relates to an immunogenic peptide comprising a fragment of an HBV protein, wherein said fragment is 20-34 amino acids in length and wherein said fragment comprises:

a) at least 10 consecutive amino acids of the region from position 57 to position 78 of HBV-X, preferably comprising:
   - the amino acid sequence set forth in SEQ ID NO:1 (x70-78), and/or
   - the amino acid sequence set forth in SEQ ID NO:2 (x67-75), and/or
   - the amino acid sequence set forth in SEQ ID NO:3 (x62-73), and/or the amino acid sequence set forth in SEQ ID NO:4 (x58-66), and/or
the amino acid sequence set forth in SEQ ID NO:5 (x57-66), or b) at least 11 consecutive amino acids of the region from position 103 to position 120 of HBV-X, preferably comprising:
the amino acid sequence set forth in SEQ ID NO:6 (x103-111), and/or
the amino acid sequence set forth in SEQ ID NO:7 (x104-113), and/or
the amino acid sequence set forth in SEQ ID NO:8 (x105-113), and/or
the amino acid sequence set forth in SEQ ID NO:9 (x110-120), or c) the amino acid sequence set forth in SEQ ID NO:10 (x132-140), or d) the amino acid sequence set forth in SEQ ID NO:11 (p124-133), or e) the amino acid sequence set forth in SEQ ID NO:12 (p164-173), or f) the amino acid sequence set forth in SEQ ID NO:13 (p275-283), or g) at least 10 consecutive amino acids of the region from position 403 to position 415 of HBV polymerase, preferably comprising:
the amino acid sequence set forth in SEQ ID NO:14 (p403-412), and/or
the amino acid sequence set forth in SEQ ID NO:15 (p404-412), and/or
the amino acid sequence set forth in SEQ ID NO:16 (p407-415), or h) at least 9 consecutive amino acids of the region from position 509 to position 523 of HBV polymerase, preferably comprising:
the amino acid sequence set forth in SEQ ID NO:17 (p509-517), and/or
the amino acid sequence set forth in SEQ ID NO:18 (p515-523), or i) at least 10 consecutive amino acids of the region from position 649 to position 658 of HBV polymerase, comprising:
the amino acid sequence set forth in SEQ ID NO:19 (p649-658), and/or
the amino acid sequence set forth in SEQ ID NO:20 (p650-658), or j) at least 10 consecutive amino acids of the region from position 693 to position 706 of HBV polymerase, preferably comprising:
the amino acid sequence set forth in SEQ ID NO:21 (p693-701), and/or
the amino acid sequence set forth in SEQ ID NO:22 (p697-706), or k) the amino acid sequence set forth in SEQ ID NO:23 (p723-731), or l) at least 10 consecutive amino acids of the region from position 755 to position 765 of HBV polymerase, comprising:
the amino acid sequence set forth in SEQ ID NO:24 (p755-764), and/or
the amino acid sequence set forth in SEQ ID NO:25 (p756-765), or m) the amino acid sequence set forth in SEQ ID NO:26 (p829-837).

In one embodiment, the peptide consists of said fragment of an HBV protein.

In another embodiment, said peptide is 20-34 amino acids in length, such as 20, 21, 22, 23, 24, 25, 26, 27, 28, 29, 30, 31, 32, 33 or 34 amino acids length, such as 20-33 amino acids in length, e.g. 20-32 amino acids in length, such as 20-31 amino acids in length, e.g. 20-30 amino acids in length, such as 20-29 amino acids in length, e.g. 20-28 amino acids in length, such as 20-27 amino acids in length, e.g. 20-26 or 20-25 amino acids in length.

In a further embodiment, said fragment is 20-33 amino acids in length, such as 20, 21, 22, 23, 24, 25, 26, 27, 28, 29, 30, 31, 32, 33 or 34 amino acids length, e.g. 20-32 amino acids in length, such as 20-31 amino acids in length, e.g. 20-30 amino acids in length, such as 20-29 amino acids in length, e.g. 20-28 amino acids in length, such as 20-27 amino acids in length, e.g. 20-26 or 20-25 amino acids in length.

In a further aspect, the invention relates to an immunogenic peptide comprising a fragment of an HBV protein, wherein said fragment is 20-34 amino acids in length, such as 20, 21, 22, 23, 24, 25, 26, 27, 28, 29, 30, 31, 32 or, 33 amino acids length, and wherein said fragment comprises one or more sequences selected from the group consisting of:

the amino acid sequence set forth in SEQ ID NO:1(x70-78),
the amino acid sequence set forth in SEQ ID NO:2(x67-75),
the amino acid sequence set forth in SEQ ID NO:3(x62-73),
the amino acid sequence set forth in SEQ ID NO:4(x58-66),
the amino acid sequence set forth in SEQ ID NO:5(x57-66),
the amino acid sequence set forth in SEQ ID NO:6(x103-111),
the amino acid sequence set forth in SEQ ID NO:7(x104-113),
the amino acid sequence set forth in SEQ ID NO:8(x105-113),
the amino acid sequence set forth in SEQ ID NO:9(x110-120),
the amino acid sequence set forth in SEQ ID NO:10 (x132-140),
the amino acid sequence set forth in SEQ ID NO:11(p124-133),
the amino acid sequence set forth in SEQ ID NO:12 (p164-173),
the amino acid sequence set forth in SEQ ID NO:13 (p275-283),
the amino acid sequence set forth in SEQ ID NO:14 (p403-412),
the amino acid sequence set forth in SEQ ID NO:15 (p404-412),
the amino acid sequence set forth in SEQ ID NO:16 (p407-415),
the amino acid sequence set forth in SEQ ID NO:17 (p509-517),
the amino acid sequence set forth in SEQ ID NO:18 (p515-523),
the amino acid sequence set forth in SEQ ID NO:19 (p649-658),
the amino acid sequence set forth in SEQ ID NO:20 (p650-658),
the amino acid sequence set forth in SEQ ID NO:21 (p693-701),
the amino acid sequence set forth in SEQ ID NO:22 (p697-706), the amino acid sequence set forth in SEQ ID NO:23 (p723-731), the amino acid sequence set forth in SEQ ID NO:24 (p755-764), the amino acid sequence set forth in SEQ ID NO:25 (p756-765), and the amino acid sequence set forth in SEQ ID NO:26 (p829-837), Preferably Wherein Said Fragment Comprises:

the amino acid sequence set forth in SEQ ID NO:1(x70-78) and the amino acid sequence set forth in SEQ ID NO:2(x67-75), or the amino acid sequence set forth in SEQ ID NO:1(x70-78) and the amino acid sequence set forth in SEQ ID NO:3(x62-73), or the amino acid sequence set forth in SEQ ID NO:1(x70-78) and the amino acid sequence set forth in SEQ ID NO:4(x58-66), or the amino acid sequence set forth in SEQ ID NO:1(x70-78) and the amino acid sequence set forth in SEQ ID NO:5(x57-66), or the amino acid sequence set forth in SEQ ID NO:2(x67-75) and the amino acid sequence set forth in SEQ ID NO:3(x62-73), or the amino acid sequence set forth in SEQ ID NO:2(x67-75) and the amino acid sequence set forth in SEQ ID NO:4(x58-66), or the amino acid sequence set forth in SEQ ID NO:2(x67-75) and the amino acid sequence set forth in SEQ ID NO:5(x57-66), or the amino acid sequence set forth in SEQ ID NO:3(x62-73) and the amino acid sequence set forth in SEQ ID NO:4(x58-66), or the amino acid sequence set forth in SEQ ID NO:3(x62-73) and the amino acid sequence set forth in SEQ ID NO:5(x57-66) or the amino acid sequence set forth in SEQ ID NO:6(x103-111) and the amino acid sequence set forth in SEQ ID NO:7(x104-113), or the amino acid sequence set forth in SEQ ID NO:6(x103-111) and the amino acid sequence set forth in SEQ ID NO:8(x105-113), or the amino acid sequence set forth in SEQ ID NO:6(x103-111) and the amino acid sequence set forth in SEQ ID NO:9(x110-120), or the amino acid sequence set forth in SEQ ID NO:7(x104-113) and the amino acid sequence set forth in SEQ ID NO:9(x110-120), or the amino acid sequence set forth in SEQ ID NO:8(x105-113) and the amino acid sequence set forth in SEQ ID NO:9(x110-120), or the amino acid sequence set forth in SEQ ID NO:14 (p403-412) and the amino acid sequence set forth in SEQ ID NO:16(p407-415), or the amino acid sequence set forth in SEQ ID NO:15 (p404-412) and the amino acid sequence set forth in SEQ ID NO:16(p407-415).

As described, in one embodiment, the immunogenic peptide comprises a fragment of HBV-X, wherein said fragment is 20-34, such as 20, 21, 22, 23, 24, 25, 26, 27, 28, 29, 30, 31, 32, 33 or 34 amino acids in length and said fragment comprises at least 10 consecutive amino acids of the region from position 57 to position 78 of HBV-X, comprising:

the amino acid sequence set forth in SEQ ID NO:1(x70-78), and/or the amino acid sequence set forth in SEQ ID NO:2(x67-75), and/or the amino acid sequence set forth in SEQ ID NO:3(x62-73), and/or the amino acid sequence set forth in SEQ ID NO:4(x58-66), and/or the amino acid sequence set forth in SEQ ID NO:5(x57-66).

In a further embodiment, the immunogenic peptide comprises a fragment of HBV-X, wherein said fragment is 20-34, such as 20, 21, 22, 23, 24, 25, 26, 27, 28, 29, 30, 31, 32, 33 or 34 amino acids in length, said fragment comprises at least 10 consecutive amino acids of the region from position 57 to position 78 of HBV-X, and said fragment comprises:

the amino acid sequence set forth in SEQ ID NO:1(x70-78) and the amino acid sequence set forth in SEQ ID NO:2(x67-75), or the amino acid sequence set forth in SEQ ID NO:1(x70-78) and the amino acid sequence set forth in SEQ ID NO:3(x62-73), or the amino acid sequence set forth in SEQ ID NO:1(x70-78) and the amino acid sequence set forth in SEQ ID NO:4(x58-66), or the amino acid sequence set forth in SEQ ID NO:1(x70-78) and the amino acid sequence set forth in SEQ ID NO:5(x57-66), or the amino acid sequence set forth in SEQ ID NO:2(x67-75) and the amino acid sequence set forth in SEQ ID NO:3(x62-73), or the amino acid sequence set forth in SEQ ID NO:2(x67-75) and the amino acid sequence set forth in SEQ ID NO:4(x58-66), or the amino acid sequence set forth in SEQ ID NO:2(x67-75) and the amino acid sequence set forth in SEQ ID NO:5(x57-66), or the amino acid sequence set forth in SEQ ID NO:3(x62-73) and the amino acid sequence set forth in SEQ ID NO:4(x58-66), or the amino acid sequence set forth in SEQ ID NO:4(x62-73) and the amino acid sequence set forth in SEQ ID NO:5(x57-66).

In a further embodiment, the most N-terminal amino acid of the fragment is the amino acid at position 53 of HBV-X or the most N-terminal amino acid of the fragment is the amino acid at a position of HBV-X that is more C-terminal than 53, i.e. position 54, position 55, position 56, etc.

In another further embodiment, the most C-terminal amino acid of the fragment is the amino acid at position 91 of HBV-X or the most C-terminal amino acid of the fragment is the amino acid at a position of HBV-X that is more N-terminal than 91, i.e. position 90, position 89, position 88, etc.

In an even further embodiment:

the most N-terminal amino acid of the fragment is the amino acid at position 53 of HBV-X or the amino acid at a position of HBV-X that is more C-terminal than 53, and the most C-terminal amino acid of the fragment is the amino acid at position 91 of HBV-X or the amino acid at a position of HBV-X that is more N-terminal than 91.

Thus, in this latter embodiment, the HBV-X fragment comprised within the peptide of the invention does not extend beyond positions 53 and 91 of HBV-X.

In another embodiment, the immunogenic peptide comprises a fragment of HBV-X, wherein said fragment is 20-34, such as 20, 21, 22, 23, 24, 25, 26, 27, 28, 29, 30, 31, 32, 33 or 34 amino acids in length and said fragment comprises at least 11 consecutive amino acids of the region from position 103 to position 120 of HBV-X, comprising:

the amino acid sequence set forth in SEQ ID NO:6(x103-111), and/or the amino acid sequence set forth in SEQ ID NO:7(x104-113), and/or the amino acid sequence set forth in SEQ ID NO:8(x105-113), and/or the amino acid sequence set forth in SEQ ID NO:9(x110-120).

In a further embodiment, the immunogenic peptide comprises a fragment of HBV-X, wherein said fragment is 20-34, such as 20, 21, 22, 23, 24, 25, 26, 27, 28, 29, 30, 31, 32, 33 or 34 amino acids in length, said fragment comprises at least 11 consecutive amino acids of the region from position 103 to position 120 of HBV-X, and the fragment comprises:

the amino acid sequence set forth in SEQ ID NO:6(x103-111) and the amino acid sequence set forth in SEQ ID NO:7(x104-113), or the amino acid sequence set forth in SEQ ID NO:6(x103-111) and the amino acid sequence set forth in SEQ ID NO:8(x105-113), or the amino acid sequence set forth in SEQ ID NO:6(x103-111) and the amino acid sequence set forth in SEQ ID NO:9(x110-120), or the amino acid sequence set forth in SEQ ID NO:7(x104-113) and the amino acid sequence set forth in SEQ ID NO:9(x110-120), or the amino acid sequence set forth in SEQ ID NO:8(x105-113) and the amino acid sequence set forth in SEQ ID NO:9(x110-120).

In a further embodiment, the most N-terminal amino acid of the fragment is the amino acid at position 103 of HBV-X or the most N-terminal amino acid of the fragment is the amino acid at a position of HBV-X that is more C-terminal than 103, i.e. position 104, position 105, position 106, etc.

In another further embodiment, the most C-terminal amino acid of the fragment is the amino acid at position 122 of HBV-X or the most C-terminal amino acid of the fragment is the amino acid at a position of HBV-X that is more N-terminal than 122, i.e. position 121, position 120, position 119, etc.

In an even further embodiment, HBV-X fragment comprised within the peptide of the invention does not extend beyond positions 103 and 122 of HBV-X.

In another embodiment, the immunogenic peptide comprises a fragment of HBV-X, wherein said fragment is 20-34, such as 20, 21, 22, 23, 24, 25, 26, 27, 28, 29, 30, 31, 32, 33 or 34 amino acids in length and said fragment comprises the amino acid sequence set forth in SEQ ID NO:10(x132-140).

In a further embodiment, the most N-terminal amino acid of the fragment is the amino acid at position 116 of HBV-X or the most N-terminal amino acid of the fragment is the amino acid at a position of HBV-X that is more C-terminal than 116, i.e. position 117, position 118, position 119, etc.

In another further embodiment, the most C-terminal amino acid of the fragment is the amino acid at position 140 of HBV-X or the most C-terminal amino acid of the fragment is the amino acid at a position of HBV-X that is more N-terminal than 140, i.e. position 139, position 138, position 137, etc.

In an Even Further Embodiment:

the most N-terminal amino acid of the fragment is the amino acid at position 116 of HBV-X or the amino acid at a position of HBV-X that is more C-terminal than 116, and the most C-terminal amino acid of the fragment is the amino acid at position 140 of HBV-X or the amino acid at a position of HBV-X that is more N-terminal than 140.

Thus, in this latter embodiment, the HBV-X fragment comprised within the peptide of the invention does not extend beyond positions 116 and 140 of HBV-X.

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises the amino acid sequence set forth in SEQ ID NO:11(p124-133).

In a further embodiment, the most C-terminal amino acid of the fragment is the amino acid at position 155 of HBV polymerase or the most C-terminal amino acid of the fragment is the amino acid at a position of HBV polymerase that is more N-terminal than 155, i.e. position 154, position 153, position 152, etc.

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises the amino acid sequence set forth in SEQ ID NO:12(p164-173).

In a further embodiment, the most N-terminal amino acid of the fragment is the amino acid at position 151 of HBV polymerase or the most N-terminal amino acid of the fragment is the amino acid at a position of HBV polymerase that is more C-terminal than 151, i.e. position 152, position 153, position 154, etc.

In another further embodiment, the most C-terminal amino acid of the fragment is the amino acid at position 174 of HBV polymerase or the most C-terminal amino acid of the fragment is the amino acid at a position of HBV polymerase that is more N-terminal than 174, i.e. position 173, position 172, position 171, etc.

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises the amino acid sequence set forth in SEQ ID NO:13(p275-283).

In a further embodiment, the most N-terminal amino acid of the fragment is the amino acid at position 262 of HBV polymerase or the most N-terminal amino acid of the fragment is the amino acid at a position of HBV polymerase that is more C-terminal than 262, i.e. position 263, position 264, position 265, etc.

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises at least 10 consecutive amino acids of the region from position 403 to position 415 of HBV polymerase, comprising:

the amino acid sequence set forth in SEQ ID NO:14 (p403-412), and/or the amino acid sequence set forth in SEQ ID NO:15 (p404-412), and/or the amino acid sequence set forth in SEQ ID NO:16 (p407-415).

In a further embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length, said fragment comprises at least 10 consecutive amino acids of the region from position 403 to position 415 of HBV polymerase, comprising:

- the amino acid sequence set forth in SEQ ID NO:14 (p403-412) and the amino acid sequence set forth in SEQ ID NO:16(p407-415), or
- the amino acid sequence set forth in SEQ ID NO:15 (p404-412) and the amino acid sequence set forth in SEQ ID NO:16(p407-415).

In a further embodiment, the most N-terminal amino acid of the fragment is the amino acid at position 390 of HBV polymerase or the most N-terminal amino acid of the fragment is the amino acid at a position of HBV polymerase that is more C-terminal than 390, i.e. position 391, position 392, position 393, etc.

In another further embodiment, the most C-terminal amino acid of the fragment is the amino acid at position 425 of HBV polymerase or the most C-terminal amino acid of the fragment is the amino acid at a position of HBV polymerase that is more N-terminal than 425, i.e. position 424, position 423, position 422, etc.

In an Even Further Embodiment:

- the most N-terminal amino acid of the fragment is the amino acid at position 390 of HBV polymerase or the amino acid at a position of HBV polymerase that is more C-terminal than 390, and
- the most C-terminal amino acid of the fragment is the amino acid at position 425 of HBV polymerase or the amino acid at a position of HBV polymerase that is more N-terminal than 425.

Thus, in this latter embodiment, the HBV polymerase fragment comprised within the peptide of the invention does not extend beyond positions 390 and 425 of HBV polymerase.

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises at least 9 consecutive amino acids of the region from position 509 to position 523 of HBV polymerase, comprising:

- the amino acid sequence set forth in SEQ ID NO:17 (p509-517), and/or
- the amino acid sequence set forth in SEQ ID NO:18 (p515-523).

In a further embodiment, the most N-terminal amino acid of the fragment is the amino acid at position 503 of HBV polymerase or the most N-terminal amino acid of the fragment is the amino acid at a position of HBV polymerase that is more C-terminal than 503, i.e. position 504, position 505, position 506, etc.

In another further embodiment, the most C-terminal amino acid of the fragment is the amino acid at position 532 of HBV polymerase or the most C-terminal amino acid of the fragment is the amino acid at a position of HBV polymerase that is more N-terminal than 532, i.e. position 531, position 530, position 529, etc.

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises at least 10 consecutive amino acids of the region from position 649 to position 658 of HBV polymerase, comprising:

- the amino acid sequence set forth in SEQ ID NO:19 (p649-658), and/or
- the amino acid sequence set forth in SEQ ID NO:20 (p650-658).

In a further embodiment, the most N-terminal amino acid of the fragment is the amino acid at position 624 of HBV polymerase or the most N-terminal amino acid of the fragment is the amino acid at a position of HBV polymerase that is more C-terminal than 624, i.e. position 625, position 626, position 627, etc.

In another further embodiment, the most C-terminal amino acid of the fragment is the amino acid at position 658 of HBV polymerase or the most C-terminal amino acid of the fragment is the amino acid at a position of HBV polymerase that is more N-terminal than 658, i.e. position 657, position 656, position 655, etc.

In an Even Further Embodiment:

- the most N-terminal amino acid of the fragment is the amino acid at position 624 of HBV polymerase or the amino acid at a position of HBV polymerase that is more C-terminal than 624, and
- the most C-terminal amino acid of the fragment is the amino acid at position 658 of HBV polymerase or the amino acid at a position of HBV polymerase that is more N-terminal than 658.

Thus, in this latter embodiment, the HBV polymerase fragment comprised within the peptide of the invention does not extend beyond positions 624 and 658 of HBV polymerase.

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises at least 10 consecutive amino acids of the region from position 693 to position 706 of HBV polymerase, comprising:

- the amino acid sequence set forth in SEQ ID NO:21 (p693-701), and/or
- the amino acid sequence set forth in SEQ ID NO:22 (p697-706).

In a further embodiment, the most N-terminal amino acid of the fragment is the amino acid at position 672 of HBV polymerase or the most N-terminal amino acid of the fragment is the amino acid at a position of HBV polymerase that is more C-terminal than 672, i.e. position 671, position 670, position 696, etc.

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises the amino acid sequence set forth in SEQ ID NO:23(p723-731).

In a further embodiment, the most C-terminal amino acid of the fragment is the amino acid at position 751 of HBV polymerase or the most C-terminal amino acid of the fragment is the amino acid at a position of HBV polymerase that is more N-terminal than 751, i.e. position 750, position 749, position 748, etc.

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises at least 10 consecutive amino acids of the region from position 755 to position 765 of HBV polymerase, comprising:

the amino acid sequence set forth in SEQ ID NO:24 (p755-764), and/or the amino acid sequence set forth in SEQ ID NO:25 (p756-765).

In another embodiment, the immunogenic peptide comprises a fragment of HBV polymerase, wherein said fragment is 20-34, such as 20, 21, 22, 23, 24, 25, 26, 27, 28, 29, 30, 31, 32, 33 or 34 amino acids in length and said fragment comprises the amino acid sequence set forth in SEQ ID NO:26(p829-837).

In a further embodiment, the most N-terminal amino acid of the fragment is the amino acid at position 815 of HBV polymerase or the most N-terminal amino acid of the fragment is the amino acid at a position of HBV polymerase that is more C-terminal than 815, i.e. position 816, position 817, position 818, etc.

In a further embodiment, the peptide of the invention comprises or consists of a sequence selected from the group consisting of:

```
SEQ ID NO: 31:
HLSLRGLPVCAFSSAGPCALRFTSA (SLP1),

SEQ ID NO: 32:
LSAMSTTDLEAYFKDCLFKDWEELG (SLP2),

SEQ ID NO: 33:
ASSSSSCLHQSAVRKAAYSHLSTSK (SLP3),

SEQ ID NO: 34:
RKLHLYSHPIILGFRKIPMGVGLSP (SLP4),

SEQ ID NO: 35:
GFAAPFTQCGYPALMPLYACIQAKQA (SLP5),

SEQ ID NO: 36:
ARQRPGLCQVFADATPTGWGLAIGH (SLP6)
and

SEQ ID NO: 37:
SPSVPSHLPDRVHFASPLHVAWRPP (SLP7).
```

In a further embodiment, the peptide of the invention comprises or consists of a sequence selected from the group consisting of:

```
SEQ ID NO: 121:
KLHLYSHPIILGFRKIPMGVGLSPFLL (SLP8),

SEQ ID NO: 122:
GLLGFAAPFTQCGYPALMPLYACIQAKQAFT (SLP9),
and

SEQ ID NO: 123:
ARQRPGLCQVFADATPTGWGLAIGHQRMR (SLP10).
```

SEQ ID NOs: 121, 122 and 123 are variants of SLP4, SLP5 and SLP6, respectively. Potential improvements in these variants include: additional putative epitopes/ligands that are introduced by extending the N-/C-terminus, or an increase in manufacturability by extending or shortening the N-/C-terminus without the loss of (putative) epitopes/ligands.

In a further embodiment, the peptide of the invention does not comprise or consists of any of the peptides described under SEQ ID NOs: 53, 54, 59, 70, 76 and 79 in WO15187009, i.e.

```
SEQ ID NO: 38:
VVNEKRRLKLIMPARFYPTHTKYLPLDKGIKPYY (SEQ ID NO: 53
in WO15187009),

SEQ ID NO: 39:
YPTHTKYLPLDKGIKPYYPDQVVNHYFQTRHYL (SEQ ID NO: 54
in WO15187009),

SEQ ID NO: 40:
TAESRLVVDFSQFSRGISRVSWPKFAVPNLQSL (SEQ ID NO: 59
in WO15187009),

SEQ ID NO: 41:
QRMRGTFVAPLPIHTAELLAACFARSRSGAKL (SEQ ID NO: 70
in WO15187009),

SEQ ID NO: 42:
ALPSPSPSAVPADHGAHLSLRGLPVCAFSSAGP (SEQ ID NO: 76
in WO15187009),
or

SEQ ID NO: 43:
LEAYFKDCVFKDWEELGEEIRLKVFVLGGCRHKL (SEQ ID NO: 79
in WO15187009).
```

In a further main aspect, the invention relates to an immunogenic peptide comprising a fragment of an HBV protein, wherein said peptide is 20-34 amino acids in length and wherein said fragment comprises a sequence selected from the group consisting of: SEQ ID NO:1 to SEQ ID NO:26.

Preferably, immunogenic peptides of the invention are capable of inducing a potent combined antigen-directed CD4+ T helper and CD8+ cytotoxic T cell response, when administered to a human subject. Preferably, the peptides can be used effectively in the prevention, partial clearance and/or treatment or full clearance of HBV, an HBV-related disease or condition in a subject, preferably as detectable by:

- activation or an induction of the immune system and/or an increase in antigen-specific activated CD4+ and/or CD8+ T-cells in peripheral blood or in tissues as established by ELISpot or ELISA assay or related suitable techniques or by HLA-multimer staining of CD4+ or CD8+ T cells or an increase of the cytokines produced by these T-cells as established by intracellular cytokine staining of or cytokine capture on CD4+ and CD8+ T cells in flow cytometry after at least one week of treatment; and/or
- inhibition of proliferation of antigen-related infection or a detectable decrease of antigen-expressing cells or a decrease in cell viability of antigen-expressing cells; and/or
- induction or increased induction of cell death of antigen expressing cells; and/or
- inhibition or prevention of the increase of antigen-expressing cells; and/or
- decrease of viral load (e.g. a decrease in serum viral DNA, viral RNAs or viral proteins) premalignant stages of the disease); and/or
- decrease of hepatocytes harboring integrated viral DNA and/or covalently closed circular DNA (cccDNA)
- decrease of the reference lesion size; and/or
- decrease of the reference tumor size; and/or
- increase of survival rates (e.g. Progression Free Survival, Overall Survival).

In a preferred embodiment, a peptide used in the invention comprises a CTL epitope as described above and a T helper epitope that shows binding affinity, preferably at least intermediate binding affinity, more preferably high binding affinity to an HLA class II molecules that is encoded by an HLA allele predominant in the population of human subjects to be treated.

In a preferred embodiment, peptides used in the invention do not have a cysteine residue at the N- or C-terminus of the peptide.

Furthermore, in another preferred embodiment, peptides used in the invention do not comprise more than two cysteine residues.

In another preferred embodiment, peptides used in the invention do not comprise more than three methionines.

In another preferred embodiment, peptides used in the invention do not have a glutamine at the N-terminus.

Preferably, a peptide used in the invention, is an isolated peptide, wherein "isolated" does not reflect the extent to which the peptide is purified, but indicates that the peptide has been removed from its natural milieu (i.e., that has been subject to human manipulation), and may be a recombinantly produced peptide or a synthetically produced peptide.

Peptides are typically produced synthetically. This may be done by solid phase peptide synthesis or by any other suitable method.

In a further aspect, the invention relates to a polynucleotide comprising a nucleotide sequence encoding a peptide according to the invention. As explained above, the term "fragment of an HBV protein" means an amino acid sequence that corresponds to a partial sequence of an HBV protein. If it is specified that a peptide comprises a fragment of an HBV protein of a certain length, it means that the fragment is not shorter or longer. For example, if it is specified that the fragment is 20-34 amino acids in length, this means that such a peptide does not comprise a consecutive sequence of said HBV protein of 35 amino acids in length or more. As a consequence, a peptide of the invention will not comprise a fragment of an HBV protein which is more than 34 amino acids in length. Therefore, it is to be understood that a polynucleotide of the invention comprising a nucleotide sequence encoding a peptide according to the invention will also not encode a peptide that comprises a fragment of an HBV protein which is more than 34 amino acids in length.

In a further aspect, the invention relates to an immunogenic composition comprising:

- a peptide according to the invention as described herein or a polynucleotide according to the invention as described herein, and
- a pharmaceutically-acceptable carrier, optionally further comprising an adjuvant.

Suitable methods for polynucleotide-based vaccination have e.g. been described in Trimble et al. 2015 Lancet 386:2078; Kranz et al. 2016 Nature 534:396; WO2011015656A2; Kratzer, et al. 2018 AASLD, The Liver Meeting 2018, abstract #426; WO2017080920; and Boni et al. 2019 Int J Mol Sci 20(11):2754.

In a further aspect, the invention relates to a recombinant virus comprising a polynucleotide according to the invention.

Immunogenic compositions used in the invention are preferably for, and therefore formulated to be suitable for, administration to a human subject. Preferably, the administration is parenteral, e.g. intravenous, subcutaneous, intramuscular, intradermal, intracutaneous and/or intratumoral administration, i.e. by injection.

The immunogenic compositions are preferably chemically stable, i.e. the peptides in the composition do not chemically degrade or decompose. Thus, preferably, the amount of un-degraded, un-decomposed and/or unreacted peptides within the solution and/or composition is at least 90%, 91%, 92%, 93%, 94%, 95%, 96%, 97%, 98%, 99% or even 100% by weight as compared to its original, after storage of the solution or liquid composition for at least about 0.5, 1, 1.5, 2 or at least 3 hours at room temperature. Chemical stability can be assessed using any suitable technique known in the art, for instance using UPLC/MS as exemplified herein. When using UPLC/MS, a solution/composition is defined as chemically stable if the total % area of peaks that do not represent the desired peptide product in the UV spectrum after storage of at least about 0.5, 1, 1.5, 2 or at least 3 hours at room temperature is at most 20%, 15%, 10%, 9%, 8%, 7%, 6%, 5%, 4%, 3%, 2%, 1%, or 0% as compared to its original.

The immunogenic compositions are preferably also physically stable, i.e. the peptides in the composition do not precipitate or re-disperse. Physical stability can be assessed using any suitable technique known in the art, for instance by visual inspection or by particle distribution using a Malvern Mastersizer as exemplified herein, wherein average particle size is expressed in D(0.5). When using Malvern Mastersizer for assessing physical stability as exemplified herein, a solution/composition is defined as physically stable if the average D (0.5) after storage of at least about 0.5, 1, 1.5, 2 or at least 3 hours at room temperature is increased at most 50%, 40%, 30%, 20%, 10% or 5% as compared to its original (i.e. the freshly prepared solution directly after preparation). Preferably, a solution/composition is defined as physically stable if the average D(0.5) after storage of 3 hours at room temperature is increased at most 50%, 40%, 30%, 20%, 10% or 5%, preferably at most 20%, as compared to its original.

In one embodiment, the immunogenic composition comprises or consists of a mixture of dry or lyophilized peptides that are to be administered together.

Immunogenic compositions for use in the invention may be prepared by any suitable method. In some embodiments, the immunogenic composition(s) are prepared from dried, preferably lyophilized, peptides.

For example, the composition may be prepared by a method comprising the following steps:

a) providing a vial comprising dried, preferably lyophilized, peptides;
b) thawing the peptides, preferably for about 5-30 min;
c) adding a reconstitution composition to the vial comprising the peptides, preferably without swirling the vial;
d) allowing to admix, preferably for about 0.5-5 minutes; and
e) swirling until a clear solution is obtained, preferably for about 1-3 minutes.

Preferably, steps b) to e) are performed at room temperature.

Preferably, said vial comprises peptides in an amount for injection as a single volume in a method for prevention and/or treatment, preferably a method of treatment and/or prevention as defined herein, i.e. a single pharmaceutical dosage unit, or part thereof in case of multiple injections at difference locations of the subject's body at substantially the same time point.

In one embodiment, the reconstitution composition of step c) comprises or consists of DMSO and/or water-for-injection. In another embodiment, the reconstitution composition of step c) of the method for reconstituting peptides comprises or consists of about 60-80% v/v aqueous solution comprising an organic acid, about 5-10% v/v propylene glycol (CAS no. 57-55-6), about 10-20% v/v lower alcohol and about 5-10% v/v non-ionic hydrophilic surfactant. In one embodiment, the organic acid is citric acid and the citric acid is present in the aqueous solution in a concentration of about 0.05-0.1 M. In one embodiment, the lower alcohol is ethanol. In one embodiment, the non-ionic hydrophilic surfactant:

a. is a mono-, di or triglyceride, preferably an ethoxylated triglyceride, and/or
b. has a hydrophilic-lipophilic balance (HLB) value between 9 and 14. In a further embodiment, the non-ionic hydrophilic surfactant is ethoxylated castor oil, preferably polyoxyethyleneglyceroltriricinoleate 35 (CAS no. 61791-12-6).

In one embodiment, the composition comprises or consists of about 75% v/v aqueous solution comprising about 0.1 M citric acid, about 6.25% v/v propylene glycol (CAS no. 57-55-6), about 12.5% v/v ethanol and about 6.25% v/v polyoxyethyleneglyceroltriricinoleate 35 (CAS no. 61791-12-6).

Preferably, the amount of reconstitution composition in step c) is in a range of from about 0.5 and 2 mL, preferably 1 mL. Preferably, the amount of reconstituted peptides in step (a) is the total amount of reconstituted peptides as obtained after step e), i.e. within the clear solution obtained after step e).

In one embodiment, the reconstituted composition comprises or consists of about 1-2 mg/mL peptides, 0.038 M citric acid, about 3.13% v/v propylene glycol (CAS no. 57-55-6), about 6.25% v/v ethanol, about 3.13% v/v polyoxyethyleneglyceroltriricinoleate 35 (CAS no. 61791-12-6) and about 50% of an oil-based adjuvant, preferably Montanide ISA 51 VG (Seppic), in water.

Dried peptides may be peptides free of further constituents but may also comprise buffer components such as trifluoroacetic acid (TFA), salts such as sodium, potassium or phosphate salts (e.g. NaCl, KCl and $NaPO_4$). The amount of further constituents is preferably less than 30%, more preferably less than 25%, of the total weight of the dry peptides to be reconstituted. Dried peptides to be reconstituted may be in a physical dried state as can be obtained by processes such as, but not limited to, rotor evaporation, lyophilization (freeze drying) and spray drying.

Adjuvants

In one embodiment, a composition of the invention further comprises an adjuvant or the treatment or use according to the invention further includes administration of an adjuvant. The term "adjuvant" is used herein to refer to substances that have immune-potentiating effects and are co-administered, or added to, or co-formulated with an antigen in order to enhance, induce, elicit, and/or modulate the immunological response against the antigen when administered to a subject. In one embodiment, the adjuvant is physically linked, such as covalently linked, to the peptide (s) to be reconstituted.

In one embodiment, the adjuvant is an emulsifying adjuvant. For example, in one embodiment, the adjuvant is an oil-based adjuvant. Oil-based adjuvants can be used to form emulsions (e.g. water-in-oil or oil-in-water emulsions) and are appreciated in the art to enhance and direct the immune response. Preferably the oil-based adjuvant is a mineral oil-based adjuvant. Non-limiting examples of oil-based adjuvants are bio-based oil adjuvants (based on vegetable oil/fish oil, etc.), squalene-based adjuvant (e.g. MF59), Syntex Adjuvant Formulation (SAF; Lidgate, Deborah M, Preparation of the Syntex Adjuvant Formulation (SAF, SAF-m, and SAF-1), In: *Vaccine Adjuvants*, Volume 42 of the series Methods in Molecular Medicine™ p229-237, ISSN1543-1894), Freund's Complete Adjuvant (FCA), Freund's Incomplete Adjuvant (FIA), adjuvants based on peanut oil (e.g. Adjuvant 65), Lipovant (Byars, N. E., Allison, A. C., 1990. Immunologic adjuvants: general properties, advantages, and limitations. In: Zola, H. (Ed.), *Laboratory Methods in Immunology*. p 39-51), ASO4 (A. Tagliabue, R. Rappuoli Vaccine adjuvants: the dream becomes real Hum. Vaccine, 4 (5), 2008, p347-349), Montanide adjuvants, which are based on purified squalene and squalene emulsified with highly purified mannide mono-oleate (e.g. Montanide ISA 25 VG, 28 VG, 35 VG, 50 V, 50 V2, 51 VG, 61 VG, 70 VG, 70 M VG, 71 VG, 720 VG, 760 VG, 763 A VG, 775 VG, 780 VG, 201 VG, 206 VG, 207 VG). More preferably, the oil-based adjuvant is Montanide ISA 51VG (Seppic), which is a mixture of Drakeol VR and mannide monooleate.

Other suitable adjuvants are adjuvants that activate antigen presenting cells, such as dendritic cells. For example, such adjuvant may via the Toll-like receptors and/or via a RIG-I (Retinoic acid-Inducible Gene-1) protein and/or via an endothelin receptor. Immune modifying compounds that are capable of activation of the innate immune system can be activated particularly well via Toll like receptors (TLRs), including TLRs 1-10. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heat shock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR3 may be activated with bacterial flagellae or flagellin. TLR6 may be activated by mycobacterial lipoproteins and group B *Streptococcus* heat labile soluble factor (GBS-F) or *Staphylococcus* modulins. TLR7 may be activated by imidazoquinolines, such as imiquimod, resiquimod and derivatives imiquimod or resiquimod (e.g. 3 M-052). TLR9 may be activated by unmethylated CpG DNA or chromatin—IgG complexes. Particularly preferred adjuvants comprise, but are not limited to, synthetically produced compounds comprising dsRNA, poly(I:C), poly I:CLC, unmethylated CpG DNA which trigger TLR3 and TLR9 receptors, IC31, a TLR 9 agonist, IMSAVAC, a TLR4 agonist, Montanide ISA-51, Montanide ISA 720 (an adjuvant produced by Seppic, France). RIG-I protein is known to be activated by ds-RNA just like TLR3 (Kato et al, (2005) *Immunity,* 1: 19-28).

A further particularly preferred TLR ligand is a pam3cys and/or derivative thereof, preferably a pam3cys lipopeptide or variant or derivative thereof, preferably such as described in WO2013051936A1, more preferably U-Pam12 or U-Pam14 or AMPLIVANT®. Pam3cys and/or derivatives thereof may optionally be covalently linked to the peptide antigen(s).

Further preferred adjuvants are Cyclic dinucleotides (CDNs), Muramyl dipeptide (MDP) and poly-ICLC. In a preferred embodiment, the adjuvants of the invention are non-naturally occurring adjuvants such as the pam3cys lipopeptide derivative as described in WO2013051936A1, Poly-ICLC, imidazoquinoline such as imiquimod, resiquimod or derivatives thereof, CpG oligodeoxynucleotides (CpG-ODNs) having a non-naturally occurring sequence, and peptide-based adjuvants, such as muramyl dipeptide (MDP) or tetanus toxoid peptide, comprising non-naturally occurring amino acids.

Further preferred are adjuvants selected from the group consisting of: 1018 ISS, aluminum salts, Amplivax, AS 15, BCG, CP-870,893, CpG7909, CyaA, dSLIM, GM-CSF, IC30, IC31, ImuFact EV1P321, IS Patch, ISS, ISCOMATRIX, JuvImmune, lipoplexes, liposomes, LipoVac, MF59, monophosphoryl lipid A, Montanide IMS 1312, nanoparticles (such as nanoparticles wherein an adjuvant has been integrated), OK-432, OM-174, OM-197-MP-EC, ONTAK, PepTel®, vector system, PLGA microparticles, SRL172, virosomes and other Virus-like particles, Pam3Cys-GDPKHPKSF, YF-17D, VEGF trap, R848, beta-glucan, Aquila's QS21 stimulon, vadimezan, AsA404 (DMXAA), STING (stimulator of IFN genes) agonist (e.g. c-di-GMP VacciGrade™), PCI, NKT (natural killer T cell) agonist (e.g. alpha-galactosylceramide or alpha-GalCer, RNAdjuvant® (Curevac), retinoic acid inducible protein I ligands (e.g. 3 pRNA or 5'-triphosphate RNA).

Methods of Treatment and Uses

Immunogenic peptides of the invention, polynucleotides of the invention, recombinant viruses of the invention and immunogenic compositions of the invention can be used for the treatment of HBV infections, such as chronic HBV infections and/or the treatment of HBV-related diseases.

Examples of diseases to be treated using the immunogenic peptides, polynucleotides and immunogenic compositions of the invention include, without limitation, hepatitis B infection, such as chronic hepatitis B infection, hepatitis B-related cirrhosis and hepatitis-B related hepatocellular carcinoma.

Accordingly, in a further aspect, the invention relates to a peptide according to the invention, a polynucleotide according to the invention or an immunogenic composition according to invention for use as a medicament.

In a further aspect, the invention relates to a peptide according to the invention, a polynucleotide according to the invention or an immunogenic composition according to invention for use in the treatment or prevention of an HBV-related disease.

In a further aspect, the invention relates to a method for the treatment or prevention of HBV-related diseases comprises the step of administration, to a human subject in need thereof, of an immunogenic peptide according to the invention, a polynucleotide according to the invention or an immunogenic composition according to invention.

Preferably, administration is intravenous, subcutaneous, or intramuscular, although other administration routes can be envisaged, such as mucosal administration or intradermal and/or intracutaneous administration, e.g., by injection.

Preferably, the administration of the immunogenic composition(s) induce(s) a cytotoxic CD8+ T cell response against at least one HLA-binding peptide sequence presented by an HLA class I molecule comprised in a long peptide. More preferably, the administration of the immunogenic composition(s) induce(s) a cytotoxic CD8+ T cell response, in conjunction with a helper CD4+ T cell response against an HLA-binding peptide sequence presented by an HLA class II molecule comprised in the immunogenic composition(s). Preferably, the administration is for the prevention, partial clearance and/or treatment or full clearance of an HBV-related infection or disease in a subject, preferably as detectable by:

- activation or induction of the immune system and/or an increase in antigen-specific activated CD4+ and/or CD8+ T-cells in peripheral blood or in tissues as established by ELISpot or ELISA assay or related suitable techniques or by HLA-multimer staining of CD4+ or CD8+ T cells or an increase of the cytokines produced by these T-cells as established by intracellular cytokine staining or cytokine capture on CD4+ and CD8+ T cells in flow cytometry after at least one week of treatment; and/or
- inhibition of proliferation of antigen-related infection or a detectable decrease of antigen-expressing cells or a decrease in cell viability of antigen-expressing cells; and/or
- induction or increased induction of cell death of antigen-expressing cells; and/or
- inhibition or prevention of the increase of antigen-expressing cells; and/or
- decrease of viral load (premalignant stages of the disease); and/or
- decrease of the reference lesion size; and/or
- decrease of the reference tumor size; and/or
- increase of survival rates (e.g. PFS, OS).

Combinations

In some embodiments, the treatment comprises administration an immunogenic peptide, polynucleotide or a recombinant virus of the invention in combination with further immunogenic peptides, polynucleotides or recombinant viruses. For example, the treatment may comprise administration of two or more, such as three, four, five, six, seven, eight or more immunogenic peptides.

The two or more peptides may all be comprised within one immunogenic composition, or the plurality of peptides may be divided over two or more compositions. If the peptides are divided over two or more compositions, these compositions may be mixed prior to administration and thus be co-administered, or they may be administered separately. Typically, all compositions, and thus all peptides of the plurality of peptides will be administered to the subject within in a time frame of 24 hours, preferably within 4, 2 or 1 hour.

If two or more compositions are administered, the administration may be at the same site, e.g. in the same limb, or at two or more different sites. In the course of the treatment, the administration of the composition(s) may be carried out once or alternatively may be repeated (boosted) subsequently, such as, but not limited to, twice or three times.

In a preferred embodiment, the method of treatment comprises a combination of long peptides wherein said combination of long peptides comprises HLA-binding peptide sequences capable of binding to at least 70%, 80%, 90%, 92%, 94%, 95%, 96%, 97%, 98%, 99% or 100% of the HLA class I molecules that are encoded by HLA alleles predominant in the population of human subjects to be treated. Preferred HLA class I HLA-binding peptide sequences in long peptides according to the invention are HLA-binding peptide sequences capable of binding to the HLA class I allele supertype classes HLA-A*01, HLA-A*02, HLA-A*03, HLA-A*24, HLA-B*07, HLA-B*08, HLA-B*27, HLA-B*44, HLA-B*58, HLA-B*62, and HLA-supertype A*01 combinations, HLA-A*01/A*03 and HLA-A*01/A*24 and their respective subtypes (Sidney et al 2008 BMC Immunology 9), preferably HLA-A0101; HLA-A0201; HLA-A0206; HLA-A0301; HLA-A1101; HLA-A2301; HLA-A2402; HLA-A2501; HLA-A2601; HLA-A2902; HLA-A3001; HLA-A3002; HLA-A3101; HLA-A3201; HLA-A3303; HLA-A6801; HLA-A6802; HLA-A7401; HLA-B0702; HLA-B0801; HLA-B1301; HLA-B1302; HLA-B1402; HLA-B1501; HLA-B1502; HLA-B1525; HLA-B1801; HLA-B2702; HLA-B2705; HLA- B3501; HLA-B3503; HLA-B3701; HLA-B3801; HLA-B3901; HLA-B4001; HLA-B4002; HLA-B4402; HLA-B4403; HLA-B4601; HLA-B4801; HLA-B4901; HLA-B5001; HLA-B5101; HLA-B5201; HLA-B5301; HLA-B5501; HLA-B5601; HLA-B5701; HLA-B5801 and HLA-B5802. In a preferred embodiment, the method of treatment comprises a combination of long peptides wherein said combination of long peptides comprises HLA-binding peptide sequences capable of binding to at least 70%, 80%, 90%, 92%, 94%, 95%, 96%, 97%, 98%, 99% or 100% of the HLA class I and HLA-binding peptide sequences capable of binding to at least 20%, 30%, 40%, 42%, 44%, 45%, 46%, 47%, 48%, 49% or 50% of the HLA class II molecules that are encoded by HLA alleles predominant in the population of human subjects to be treated.

In a preferred embodiment, a long peptide used in the invention comprises an HLA-binding peptide sequence that shows binding affinity, preferably at least intermediate binding affinity, more preferably high binding affinity to an HLA class I molecules that is encoded by an HLA allele predominant in the population of human subjects to be treated and elicits a cytotoxic CD8+ T cell response. Preferably, a long peptide used in the invention comprises an HLA-binding peptide sequence that shows binding affinity, preferably at least intermediate binding affinity, more preferably high binding affinity to at least one HLA class I molecule of the group of HLA class I molecules consisting of:

HLA-A01 (i.e. A*0101 A*0112 A*2601 A*0114 A*2610 A*2602
A*0115 A*2611 A*2603 A*2604 A*2612 A*3002 A*2613
A*3003 A*0109 A*2606 A*3004 A*0110 A*2615 A*3201
A*0111 A*2618 A*3012 A*2619 A*3202 A*2621 A*3205
A*2623 A*3206 A*2624 A*3207 A*2626 A*3009 A*3601
A*2501 A*2502 A*2504 A*8001 A*2622 A*3110 A*0103
A*2609 A*0104 A*2605 A*2617 A*0106 A*3006 A*3210
A*0107 A*3204 A*3208 A*0108 A*2614 A*3203 A*2607
A*3603 A*7410 A*2608 A*3209 A*3602 A*3604);
HLA-A02 (i.e. A*0201 A*0240 A*0271 A*0202 A*0243 A*0258
A*0203 A*0212 A*0259 A*0274 A*0204 A*0213 A*0227
A*0205 A*0215 A*0228 A*0206 A*0207 A*0218 A*0214
A*0219 A*0236 A*0267 A*0217 A*0220 A*0251 A*6802
A*0269 A*0285 A*6901 A*0256 A*0241 A*0260 A*0284
A*0209 A*0257 A*6827 A*0211 A*0224 A*0272 A*0225
A*0226 A*6828 A*0244 A*0261 A*0275 A*0245 A*0262
A*0230 A*0246 A*0216 A*0263 A*0231 A*0248 A*0266
A*0249 A*0282 A*0279 A*0237 A*0268 A*0221 A*0277
A*0247 A*0222 A*0270 A*0242 A*0273 A*6815 A*0283
A*0238 A*0254 A*0278 A*0239 A*0286 A*0250);
HLA-A03 (i.e. A*0301 A*0317 A*3101 A*0307 A*6601 A*1107
A*7401 A*0312 A*1108 A*0313 A*1109 A*0314 A*1110
A*1112 A*1114 A*1116 A*1121 A*3103 A*1104 A*7402
A*3106 A*0280 A*3109 A*3111 A*6603 A*6816 A*7405
A*1106 A*3304 A*6604 A*6819 A*7407 A*1122 A*3305
A*6803 A*6821 A*3306 A*3307 A*6808 A*7411 A*3402
A*6825 A*6823 A*3403 A*6810 A*7406 A*0305 A*1102
A*3301 A*0306 A*1103 A*3303 A*0308 A*1105 A*6801
A*0310 A*0302 A*0316 A*1101 A*0304 A*6602 A*6814
A*7404 A*0309 A*6813 A*7403 A*3404 A*6812 A*6822
A*7409 A*6805 A*7408 A*6804 A*3112 A*6824 A*6820
A*6809 A*6826 A*1113 A*1115 A*1120 A*1123 A*3104
A*3105 A*0265 A*3406);
HLA-A24 (i.e. A*2301 A*2410 A*2422 A*2402 A*2411 A*2423
A*2304 A*2427 A*2307 A*2408 A*2308 A*2421 A*2429
A*2305 A*2417 A*2452 A*2425 A*2405 A*2413 A*2426
A*2435 A*2446 A*2306 A*2406 A*2418 A*2302 A*2310
A*2433 A*2440 A*2303 A*2403 A*2434 A*2443 A*2420
A*2428 A*2438 A*2448 A*2430 A*2441 A*2442 A*2312
A*2444 A*2439 A*2449 A*2409 A*2437 A*2447);
HLA-B07 (i.e. B*0702 B*0741 B*5134 B*5510 B*0703 B*0706
B*5135 B*5515 B*0705 B*0715 B*0743 B*3542 B*5136
B*1508 B*3507 B*3543 B*5116 B*5138 B*5519 B*3501
B*5117 B*5302 B*3503 B*0721 B*3511 B*3545 B*5118
B*5306 B*4201 B*3514 B*3546 B*5308 B*5101 B*3515
B*3554 B*5121 B*5310 B*5615 B*5102 B*3521 B*3555

-continued

B*5123 B*5403 B*5616 B*5103 B*3557 B*5124 B*5301
B*3561 B*5126 B*5406 B*5401 B*5128 B*5407 B*5501
B*3532 B*5129 B*5503 B*5502 B*3533 B*4204 B*5130
B*5601 B*3535 B*4205 B*5131 B*6701 B*3536 B*5132
B*7801 B*5133 B*5509 B*0707 B*3518 B*5112 B*0709
B*3529 B*5113 B*0712 B*3530 B*0714 B*3534 B*5120
B*0716 B*3537 B*5137 B*0717 B*3539 B*5304 B*0718
B*3551 B*0723 B*3553 B*5511 B*0736 B*5514 B*3502
B*3504 B*3807 B*5604 B*3505 B*3917 B*5609 B*3506
B*3509 B*4406 B*3512 B*5104 B*5612 B*3517 B*5106
B*8101 B*8102 B*5508 B*5602 B*5513 B*0737 B*3558
B*3560 B*3806 B*5610 B*4206 B*5611 B*0726 B*3522
B*5404 B*0730 B*3531 B*3910 B*7804 B*0731 B*7802
B*3524 B*0733 B*3916 B*5108 B*3538 B*0734 B*5114
B*0725 B*5504 B*0735 B*5505 B*0739 B*5105 B*5507
B*0740 B*0704 B*3540 B*5109 B*3541 B*5110 B*0742
B*3508 B*3544 B*5603 B*5111 B*5517 B*0719 B*5605
B*0722 B*0720 B*5119 B*5613 B*0724;
HLA-B08 (i.e. B*0801 B*0815 B*0819 B*0821 B*0823 B*0818
B*0820 B*0822 B*0824 B*0825 B*0811 B*0813 B*0807
B*0802 B*0809 B*0803 B*0812 B*0808 B*0816).

As mentioned, the treatment may involve administration of two or more antigens of the invention. In one embodiment, the invention provides a method for the treatment or prevention of an HBV-related disease comprising administration to a human subject of:

- a peptide as described in claim 1a) and a peptide as described in claim 1b), or
- a peptide as described in claim 1a) and a peptide as described in claim 1c), or
- a peptide as described in claim 1a) and a peptide as described in claim 1d), or
- a peptide as described in claim 1a) and a peptide as described in claim 1e), or
- a peptide as described in claim 1a) and a peptide as described in claim 1f), or
- a peptide as described in claim 1a) and a peptide as described in claim 1g), or
- a peptide as described in claim 1a) and a peptide as described in claim 1h), or
- a peptide as described in claim 1a) and a peptide as described in claim 1i), or
- a peptide as described in claim 1a) and a peptide as described in claim 1j), or
- a peptide as described in claim 1a) and a peptide as described in claim 1k), or
- a peptide as described in claim 1a) and a peptide as described in claim 1l), or
- a peptide as described in claim 1a) and a peptide as described in claim 1m), or
- a peptide as described in claim 1b) and a peptide as described in claim 1c), or
- a peptide as described in claim 1b) and a peptide as described in claim 1d), or
- a peptide as described in claim 1b) and a peptide as described in claim 1e), or
- a peptide as described in claim 1b) and a peptide as described in claim 1f), or
- a peptide as described in claim 1b) and a peptide as described in claim 1g), or
- a peptide as described in claim 1b) and a peptide as described in claim 1h), or
- a peptide as described in claim 1b) and a peptide as described in claim 1i), or
- a peptide as described in claim 1b) and a peptide as described in claim 1j), or a peptide as described in claim 1b) and a peptide as described in claim 1k), or a peptide as described in claim 1b) and a peptide as described in claim 1l), or a peptide as described in claim 1b) and a peptide as described in claim 1m), or a peptide as described in claim 1c) and a peptide as described in claim 1d), or a peptide as described in claim 1c) and a peptide as described in claim 1e), or a peptide as described in claim 1c) and a peptide as described in claim 1f), or a peptide as described in claim 1c) and a peptide as described in claim 1g), or a peptide as described in claim 1c) and a peptide as described in claim 1h), or a peptide as described in claim 1c) and a peptide as described in claim 1i), or a peptide as described in claim 1c) and a peptide as described in claim 1j), or a peptide as described in claim 1c) and a peptide as described in claim 1k), or a peptide as described in claim 1c) and a peptide as described in claim 1l), or a peptide as described in claim 1c) and a peptide as described in claim 1m), or a peptide as described in claim 1d) and a peptide as described in claim 1e), or a peptide as described in claim 1d) and a peptide as described in claim 1f), or a peptide as described in claim 1d) and a peptide as described in claim 1g), or a peptide as described in claim 1d) and a peptide as described in claim 1h), or a peptide as described in claim 1d) and a peptide as described in claim 1i), or a peptide as described in claim 1d) and a peptide as described in claim 1j), or a peptide as described in claim 1d) and a peptide as described in claim 1k), or a peptide as described in claim 1d) and a peptide as described in claim 1l), or a peptide as described in claim 1d) and a peptide as described in claim 1m), or a peptide as described in claim 1e) and a peptide as described in claim 1f), or a peptide as described in claim 1e) and a peptide as described in claim 1g), or a peptide as described in claim 1e) and a peptide as described in claim 1h), or a peptide as described in claim 1e) and a peptide as described in claim 1i), or a peptide as described in claim 1e) and a peptide as described in claim 1j), or a peptide as described in claim 1e) and a peptide as described in claim 1k), or a peptide as described in claim 1e) and a peptide as described in claim 1l), or a peptide as described in claim 1e) and a peptide as described in claim 1m), or a peptide as described in claim 1f) and a peptide as described in claim 1g), or a peptide as described in claim 1f) and a peptide as described in claim 1h), or a peptide as described in claim 1f) and a peptide as described in claim 1i), or a peptide as described in claim 1f) and a peptide as described in claim 1j), or a peptide as described in claim 1f) and a peptide as described in claim 1k), or a peptide as described in claim 1f) and a peptide as described in claim 1l), or a peptide as described in claim 1f) and a peptide as described in claim 1m), or a peptide as described in claim 1g) and a peptide as described in claim 1h), or a peptide as described in claim 1g) and a peptide as described in claim 1i), or a peptide as described in claim 1g) and a peptide as described in claim 1j), or a peptide as described in claim 1g) and a peptide as described in claim 1k), or a peptide as described in claim 1g) and a peptide as described in claim 1l), or a peptide as described in claim 1g) and a peptide as described in claim 1m), or a peptide as described in claim 1h) and a peptide as described in claim 1i), or a peptide as described in claim 1h) and a peptide as described in claim 1j), or a peptide as described in claim 1h) and a peptide as described in claim 1k), or a peptide as described in claim 1h) and a peptide as described in claim 1l), or a peptide as described in claim 1h) and a peptide as described in claim 1m), or a peptide as described in claim 1i) and a peptide as described in claim 1j), or a peptide as described in claim 1i) and a peptide as described in claim 1k), or a peptide as described in claim 1i) and a peptide as described in claim 1l), or a peptide as described in claim 1i) and a peptide as described in claim 1m), or a peptide as described in claim 1j) and a peptide as described in claim 1k), or a peptide as described in claim 1j) and a peptide as described in claim 1l), or a peptide as described in claim 1j) and a peptide as described in claim 1m), or a peptide as described in claim 1k) and a peptide as described in claim 1l), or a peptide as described in claim 1k) and a peptide as described in claim 1m), or a peptide as described in claim 1l) and a peptide as described in claim 1m) or one or two polynucleotides comprising sequences encoding any one of the afore-mentioned combinations of peptides.

Preferably, the immunogenic composition comprises or consists of an amount of peptides that constitutes a pharmaceutical dose. A pharmaceutical dose is defined herein as the amount of active ingredients (i.e. the total amounts of peptides in a peptide-based immunogenic composition) that is applied to a subject at a given time point. A pharmaceutical dose may be applied to a subject in a single volume, i.e. a single shot, or may be applied in 2, 3, 4, 5 or more separate volumes that are applied preferably at different locations of the body, for instance in the right and the left limb. Reasons for applying a single pharmaceutical dose in separate volumes may be multiples, such as avoid negative side effects, avoiding antigenic competition and/or composition analytics considerations.

A pharmaceutical dose may be an effective amount or part of an effective amount. An "effective amount" is to be understood herein as an amount or dose of active ingredients required to prevent and/or reduce the symptoms of a disease (e.g., chronic infection, pre-cancerous condition and/or cancer) relative to an untreated patient. The effective amount of active compound(s) used to practice the present invention for preventive and/or therapeutic treatment of a disease or condition varies depending upon the manner of administration, the age, body weight, and general health of the subject. Ultimately, the attending physician or veterinarian will decide the appropriate amount and dosage regimen. Such amount is referred to as an "effective" amount. This effective amount may also be the amount that is able to induce an effective cellular T cell response in the subject to be treated, or more preferably an effective systemic cellular T cell response.

Preferably, pharmaceutical dose, or total amount of peptides applied to a subject at a given time point, either in a single or in multiple injections or administrations at a certain time point, comprises an amount of peptides in the range from 0.1 microgram to 20 mg, such as about 0.1 microgram, 0.5 microgram, 1 microgram, 5 micrograms, 10 micrograms, 15 micrograms, 20 micrograms, 30 micrograms, 40 micrograms, 50 micrograms, 60 micrograms, 70 micrograms, 80 micrograms, 90 micrograms, 100 micrograms, 150 micrograms, 200 micrograms, 250 micrograms, 300 micrograms, 350 micrograms, 400 micrograms, 450 micrograms, 500 micrograms, 650 micrograms, 700 micrograms, 750 micrograms, 800 micrograms, 850 micrograms, 900 micrograms, 1 mg, 1.1 mg, 1.2 mg, 1.3 mg, 1.4 mg, 1.5 mg, 1.6 mg, 1.7 mg, 1.8 mg, 1.9 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 15 mg or about 20 mg or any value in between. Preferred ranges of pharmaceutical doses are from 0.1 microgram to 20 mg, 1 microgram to 10 mg, 10 micrograms to 5 mg, 0.5 mg to 2 mg, 0.5 mg to 10 mg or 1 mg to 5 mg or 2 to 4 mg.

In one embodiment, the immunogenic composition used in the invention is administered in a dose of between 1 microgram and 300 micrograms, e.g. between 50 micrograms and 150 micrograms, such as approximately 100 micrograms of each peptide.

The method of the invention may be part of a combination therapy with other forms of HBV treatment, which may be provided as a separate treatment or added to the immunogenic composition of the invention. The method of the invention may be combined with drugs that inhibit viral replication (e.g. nucleoside or nucleotide analogs including entecavir, tenofovir disoproxil fumarate, tenofovir alafenamide), and/or drugs that prevent HBV entry into the cell (e.g. myrcludex), and/or drugs that inhibit viral protein productions (e.g. based on siRNAs, shRNA, CRISPR/CAS9) and/or drugs that modulate the immune response (e.g. PEG-interferon $\alpha$), activate the innate immune response (e.g. $\alpha$GalCer) and/or Hepatitis B immunoglobulins (HBIG) to support the vaccine induced immune response and/or HBV prophylactic vaccines to induce HBsAg directed antibodies, and/or liver resection or transplantation and tumor ablative therapies (e.g. transendothelial embolization, radiofrequency ablation) and or drugs that inhibit VEGFR and/or kinases and or drugs that inhibit or block immune checkpoints molecules (e.g. A2AR (Adenosine A2A receptor), B7-H3/CD276, B7-H4/VTCN1, BTLA/CD272, CTLA-4/CD152, IDO (indoleamine 2,3-dioxygenase), KIR (Killer-cell Immunoglobulin-like Receptor), LAG3 (Lymphocyte Activation Gene-3), NOX2 (nicotinamide adenine dinucleotide phosphate NADPH oxidase isoform 2), PD-1 (Programmed Death 1), PD-L1, TIM-3 (T-cell Immunoglobulin domain and Mucin domain 3), VISTA (V-domain Ig suppressor of T cell activation), SIGLEC7/CD328 and SIGLEC9/CD329, NKG2A and/or drugs that stimulate stimulatory checkpoint molecules (e.g. selected Tumor Necrosis Factor (TNF) receptor superfamily members (e.g. CD27, CD40, CD122, 4-1BB/CD137, OX-40/CD134 and GITR (Glucocorticoid-Induced TNFR family Related)), CD28 and ICOS/CD278), immunosuppressive cytokines (e.g. IL-10, TGF-β and IL-6) and/or γC cytokines (e.g. IL-7, IL-15, and IL-21 or IL-2), thalidomide and/or derivatives thereof, further immunomodulators (e.g. compounds that are known to deplete immunosuppressive Tregs and/or MDSCs)).))

Figure 8:
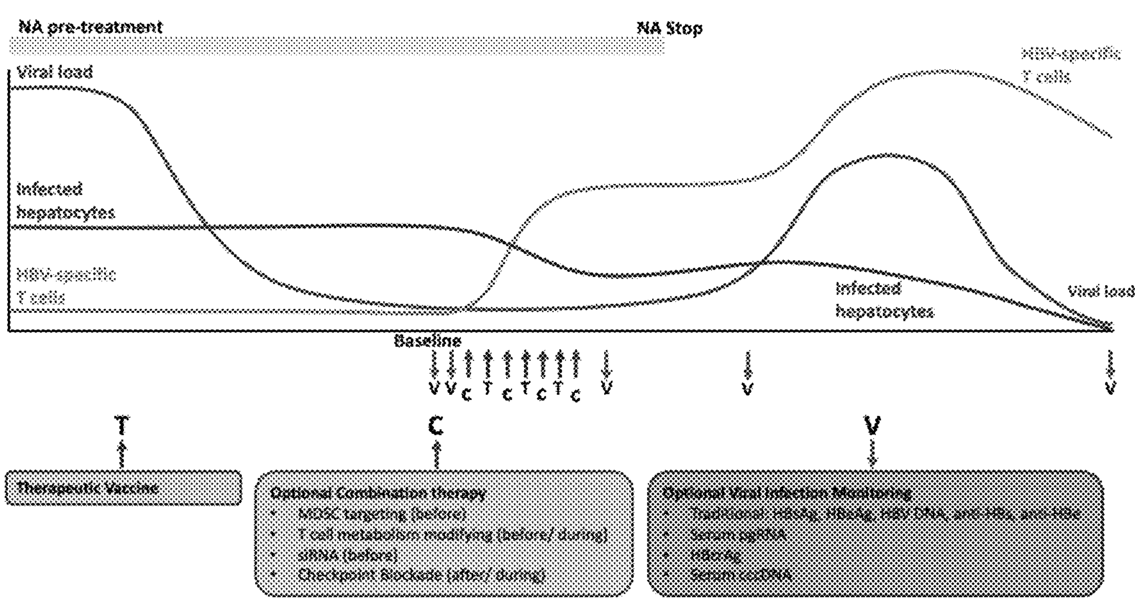
FIG. 8. Novel treatment schedule towards clearance of the HBV infection. Before start of the therapeutic vaccination (T), viral load is reduced by nucleoside/nucleotide analog (NA) treatment. When the viral load is stably low, therapeutic vaccination is given. To further improve T cell effector function, therapeutic vaccination can optionally be combined with suppressive myeloid cell (MDSC) targeting drugs (given before therapeutic vaccination), siRNA (before therapeutic vaccination), T cell metabolism modifying drugs (before or during therapeutic vaccination) or checkpoint blockade (during or after therapeutic vaccination). As a 'natural' booster, NA treatment is stopped to increase viral antigen presence, boosting HBV-specific T cells in situ to drive clearance of remaining infected hepatocytes. Adequate monitoring of the viral load is preferably carried out to evaluate vaccine efficacy and to decide on follow-up (combination) therapies and/or NA stop. Lines provide a schematic indication of the development of the indicated parameter over time. Arrows indicate preferred moments of intervention or monitoring.

In one embodiment, the immunogenic peptide(s) or composition of the invention may be combined with antiviral compounds, such as nucleoside/nucleotide analogs (NAs), in a treatment regimen comprising the following steps:

(i) antiviral (e.g. NA) treatment is given to an HBV infected patient to reduce viral load, (ii) when the viral load is significantly reduced (e.g. more than 2, 5 or 10 fold), the immunogenic peptide(s) or composition of the invention is administered (preferably intradermally or subcutaneously), and (iii) when sufficient time has passed for an initial T cell response in the patient to have occurred (e.g. between 2 and 16 weeks after the last administration of the immunogenic composition, such as between 2 and 12 weeks, e.g. between 2 and 8 weeks), optional immune monitoring (e.g. characterization of peripheral & intrahepatic T cells, in particular, determination of the vaccine specific T cell response against the administered immunogenic peptide(s) of the composition of the invention by e.g. IFNgamma ELISpot analysis or antigen specific T cell proliferation and/or FACS based phenotyping of antigen specific T cells. Optionally accompanied by determination of T cell responses against non-vaccine antigens of interest and unrelated control microbial antigens) is performed to assess whether a suitable T cell response has been evoked by the vaccine (see e.g. Rivino et al. (2018) J Clin Invest 128:668). Subsequently, antiviral treatment is interrupted or discontinued in order to increase viral antigen presentation, thus further boosting HBV-specific T cells in situ and to expose infected hepatocytes to the immune system (i.e. by increasing hepatocyte HBV protein expression and antigen presentation) to drive clearance of those remaining infected hepatocytes. To further improve T cell effector function, therapeutic vaccination can optionally be combined with suppressive myeloid cell (MDSC) targeting drugs (given before therapeutic vaccination), siRNA (before therapeutic vaccination), T cell metabolism modifying drugs (before or during therapeutic vaccination) or checkpoint blockade (during or after therapeutic vaccination). Adequate monitoring of the viral load is preferably carried out to evaluate vaccine efficacy and to decide on follow-up (combination) therapies and/or NA stop. FIG. 8 provides a non-limiting illustration of a treatment regimen according to this embodiment. This treatment regimen is particularly suitable for patients who are recommended to receive antiviral treatment according the treatment guidelines. Antiviral treatment prior to vaccination may not be necessary for infected patients that have a persistent, but low viral load. Such patients are eligible to receive a therapeutic vaccination at any given time and when sufficient time has passed for an initial T cell response in the patient to have occurred, optional immune monitoring is performed to assess whether a suitable T cell response has been evoked by the vaccine. To further improve T cell effector function, therapeutic vaccination can optionally be combined with suppressive myeloid cell (MDSC) targeting drugs (given before therapeutic vaccination), siRNA (before therapeutic vaccination), T cell metabolism modifying drugs (before or during therapeutic vaccination) or checkpoint blockade (during or after therapeutic vaccination). Adequate monitoring of the viral load is preferably carried out to evaluate vaccine efficacy and to decide on follow-up (combination) therapies.

In a further aspect, the immunogenic peptide or composition may be used in ex vivo immunization regimens. In ex vivo immunization regimens, the peptide or composition may be used to generate antigen-loaded antigen presenting cells (APCs), such as antigen-loaded activated Dendritic Cells (DCs), and subsequently stimulate expansion of antigen-specific T cells (e.g. CD4 and CD8 positive circulating T cells, Tumor Infiltrating Lymphocytes (TILs)). Such antigen-loaded APCs or expanded antigen-specific T cells are subsequently administered to a human subject.

Thus, in a further aspect, the invention relates to a peptide according to the invention or a peptide comprising a sequence selected from the group consisting of: SEQ ID NO:1 to SEQ ID NO:26 for use in ex vivo stimulation of antigen-loaded activated antigen-presenting cells or expanded antigen-specific T cells.

Similarly, in another embodiment, the method of the invention involves treating the human subject with a population of antigen-loaded activated antigen presenting cells (APCs) or expanded antigen-specific T cells, wherein said cells have been generated ex vivo (i.e. outside the body) using the immunogenic composition(s) described herein. This can e.g. be done by culturing patients' PBMCs to generate autologous activated APCs (e.g. DCs), loaded with the immunogenic compositions (i.e. antigen-loaded APCs), and subsequently stimulate and expand T cells obtained from PBMCs or Tumor Infiltrating Lymphocytes. Alternatively, antigen-specific T cells may be expanded by incubation with activated APCs cultured from PBMCs of HLA-matched healthy donors, loaded with the immunogenic compositions. Suitable techniques have been described in the art, e.g. in McCormack et al. (2018) Cytotherapy 20:385; Stevanovic et al. (2015) J Clin Oncol 33:1543; and Stevanovic et al. (2018) Clin Cancer Res, doi: 10.1158/1078-0432.

In a further embodiment, treatment with a population of activated antigen presenting cells (APCs) or expanded antigen-specific T cells is combined with direct immunization of the human subject with the immunogenic compositions described herein. Such a combined protocol may involve sequential and/or simultaneous administrations.

All patent and literature references cited in the present specification are hereby incorporated by reference in their entirety.

EXAMPLES

Example 1: Consensus Sequences for HBV-X and HBV Polymerase and Alignment with Functional Domains A frequency table was downloaded from HBVdb V42.0 (Hayer et al, 2013 Nucleic Acid Res 41:566) based on HBV sequences of all genotypes for HBV-X (n=8127) and HBV polymerase (n=7489). Positions where a gap (indicated by "-") was most frequent were deleted after which the dominating amino acid at each position was determined. Percentages of sequences containing the dominant amino acid were calculated as the conservation score.

Combining all dominant amino acids for HBV polymerase lead to the consensus sequence (SEQ ID NO:28):

```
MPLSYQHFRKLLLLDDEAGPLEEELPRLADEGLNRRVAEDLNLGNLNVS
IPWTHKVGNFTGLYSSTVPVFNPEWQTPSFPDIHLQEDIINRCQQFVGP
LTVNEKRRLKLIMPARFYPNVTKYLPLDKGIKPYYPEHVVNHYFQTRHY
LHTLWKAGILYKRETTRSASFCGSPYSWEQELQHGRLVFQTSKRHGDES
FCSQSSGILSRSPVGPCIQSQLKQSRLGLQPQQGSLARRQQGRSGSIRA
RVHPTTRRSFGVEPSGSGHIDNSASSSSSCLHQSAVRKAAYSHLSTSKR
QSSSGHAVELHNIPPSSARSQSEGPVFSCWWLQFRNSKPCSDYCLSHIV
NLLEDWGPCTEHGEHHIRIPRTPARVTGGVFLVDKNPHNTTESRLVVDF
SQFSRGNTRVSWPKFAVPNLQSLTNLLSSNLSWLSLDVSAAFYHLPLHP
AAMPHLLVGSSGLSRYVARLSSNSRIINNQHGTMQNLHDSCSRNLYVSL
LLLYKTFGRKLHLYSHPIILGFRKIPMGVGLSPFLLAQFTSAICSVVRR
AFPHCLAFSYMDDVVLGAKSVQHLESLYTAVTNFLLSLGIHLNPNKTKR
WGYSLNFMGYVIGSWGTLPQEHIVQKIKQCFRKLPVNRPIDWKVCQRIV
GLLGFAAPFTQCGYPALMPLYACIQAKQAFTFSPTYKAFLCKQYLNLYP
VARQRPGLCQVFADATPTGWGLAIGHQRMRGTFVAPLPIHTAELLAACF
ARSRSGAKLIGTDNSVVLSRKYTSFPWLLGCAANWILRGTSFVYVPSAL
NPADDPSRGRLGLYRPLLRLPFRPTTGRTSLYAVSPSVPSHLPDRVHFA
SPLHVAWRPP.
```

The resulting consensus sequence for HBV-X was determined as (SEQ ID NO:30):

```
MAARLCCQLDPARDVLCLRPVGAESRGRPLSGPLGTLPSPSPSAVPADH
GAHLSLRGLPVCAFSSAGPCALRFTSARRMETTVNAHQVLPKVLHKRTL
GLSAMSTTDLEAYFKDCVFKDWEELGEEIRLKVFVLGGCRHKLVCSPAP
CNFFTSA.
```

Figure 2:
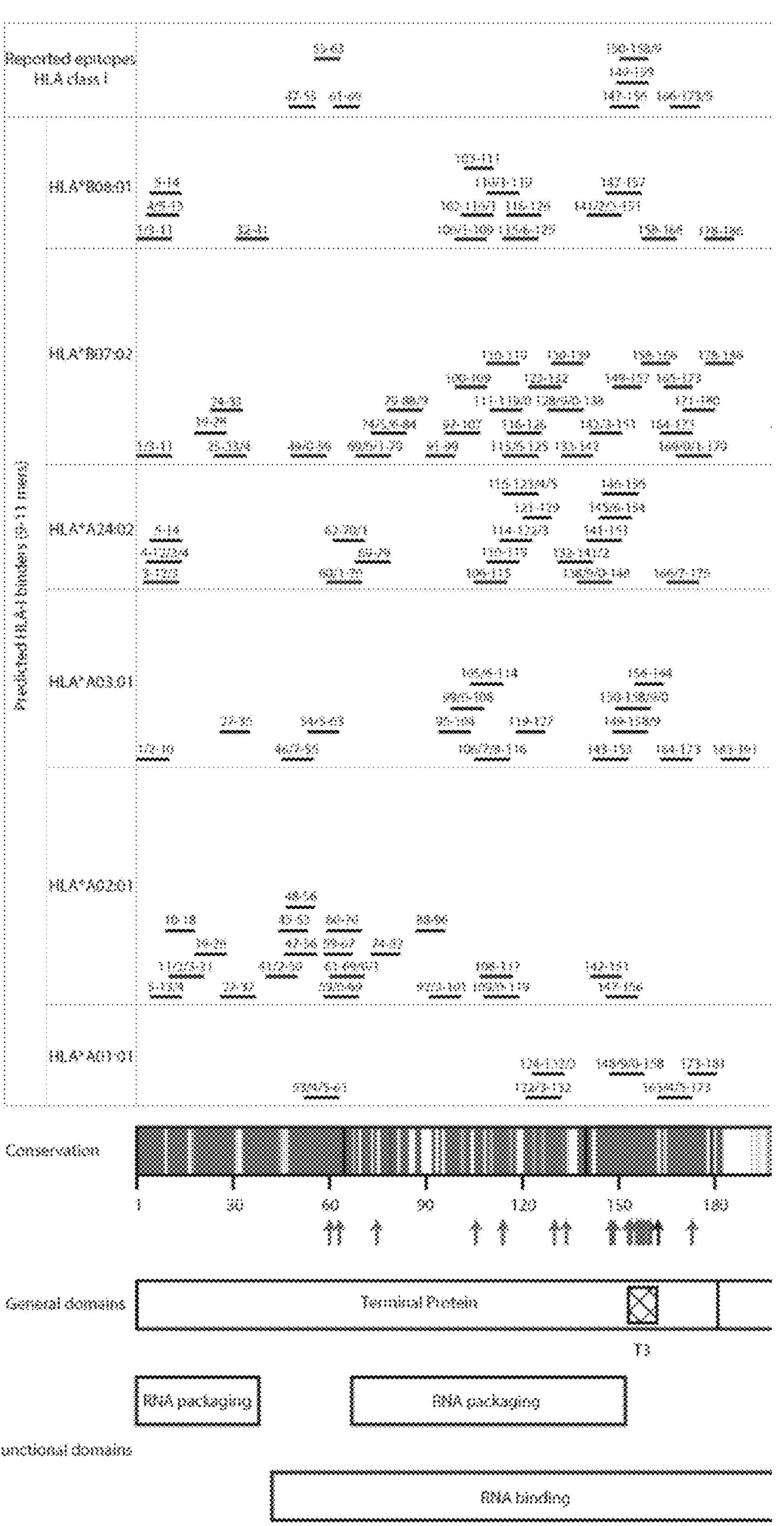
FIG. 2. Alignment of validated HLA-I epitopes and predicted HLA-binding peptide sequences to protein conservation and function for Polymerase. Depicted are the first 200 amino acids (A, E), amino acids 201-474 (B, F), 475-631 (C, G) and amino acids 632-843 (D, H). Reported validated epitope sequences obtained from the Hepitopes database are shown on top. Below this, potential novel binders predicted by NetMHCpan (9-11 amino acids) are depicted for each HLA-supertype (A-D). In addition, we plotted the frequency distribution of predicted binders (8-14 amino acids in length) over the protein sequence (E-H). The conservation score (legend) of each amino acid is shown as a horizontal grey scale-coded bar diagram. Essential amino acids for which single or combined mutation leads to loss of viral persistence 50%) are indicated by arrows matching the color of the conservation score for that particular amino acid. Amino acids which are predicted to be vital for correct folding of the viral protein are indicated with an asterisk. General domains are depicted according to previously determined nomenclature (Cao et al. 2014 J Viral Hepat 21:882) in which also the T3 domain and the YMDD motif is represented.
Figure 2:
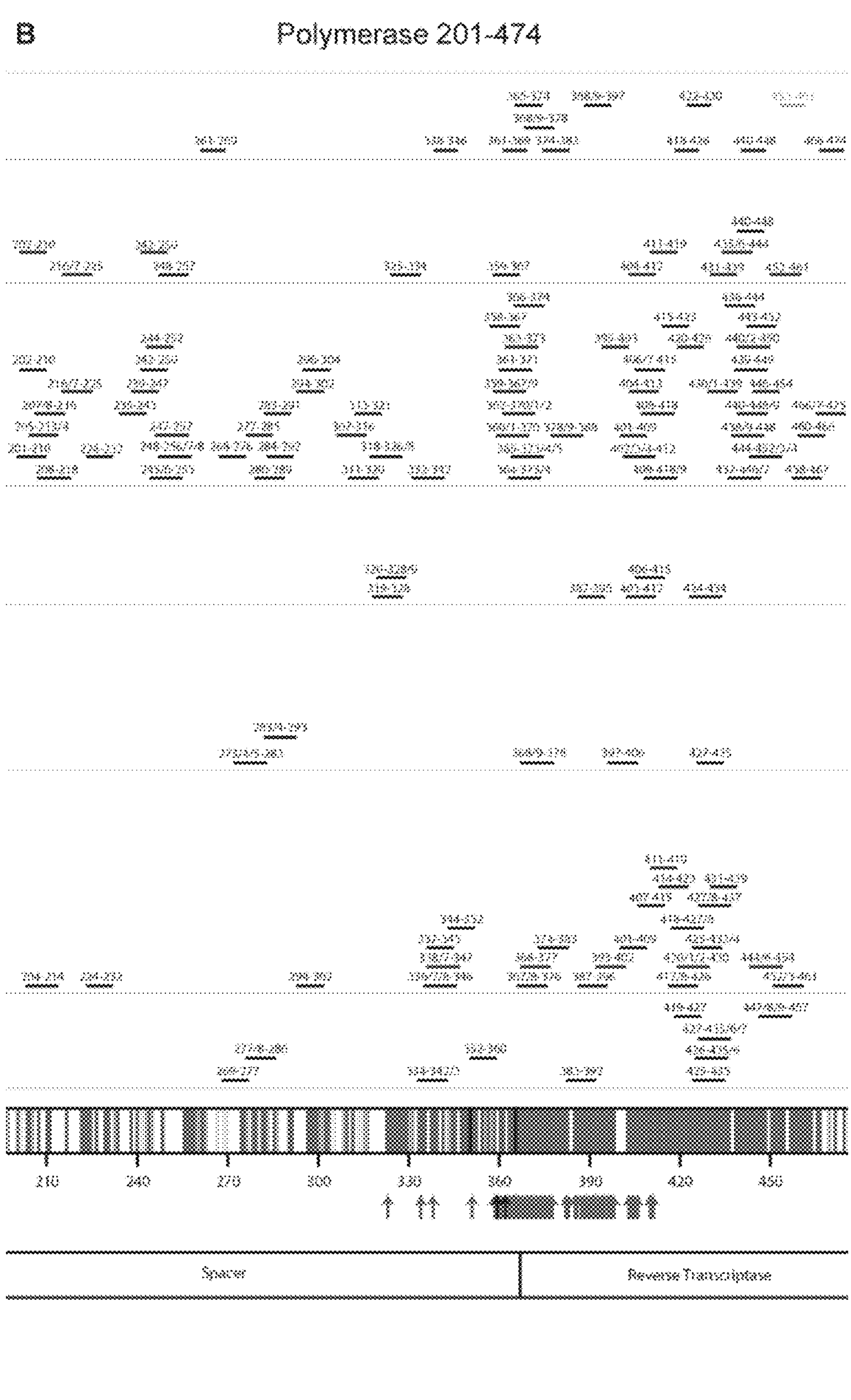
Figure 2:
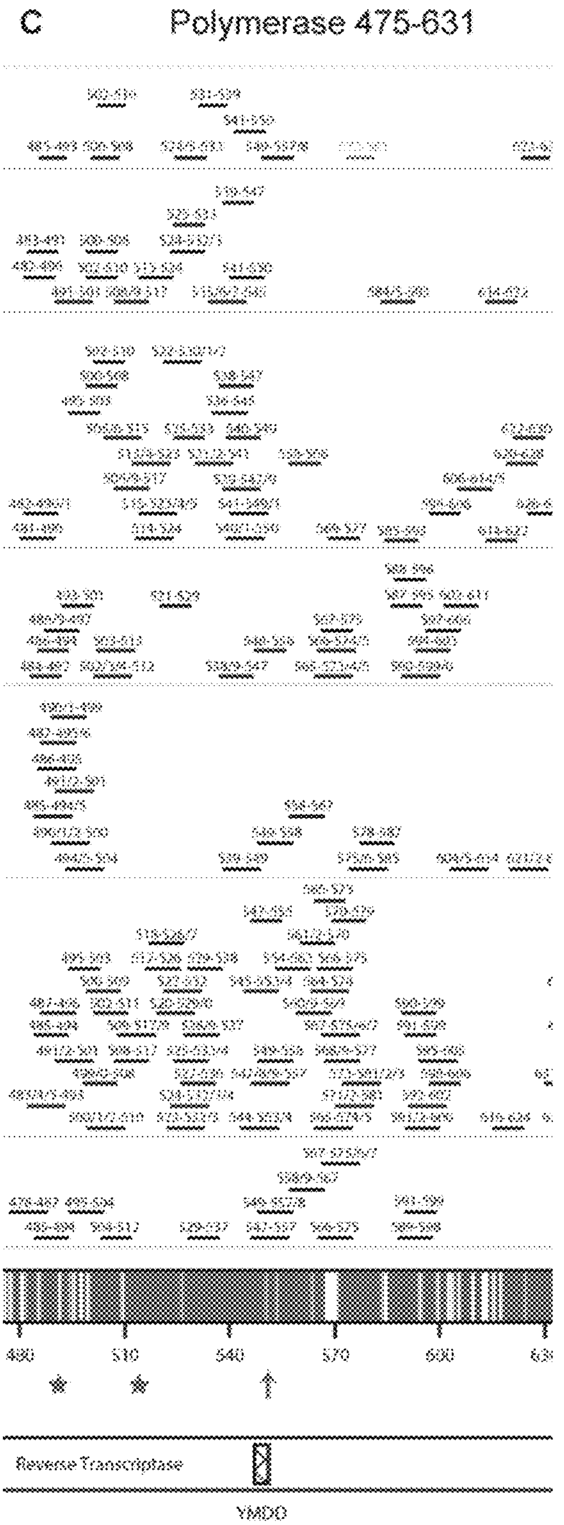
Figure 2:
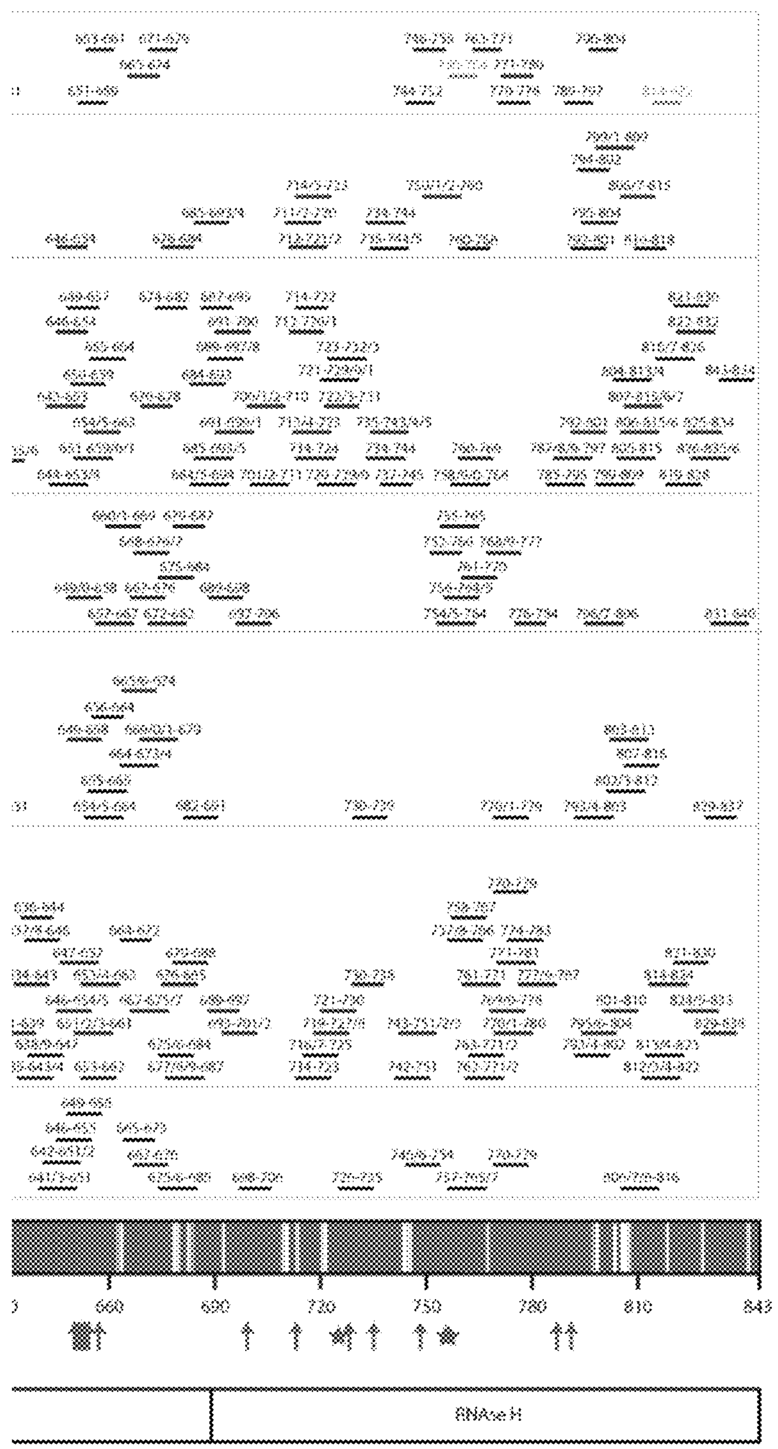
Figure 2:
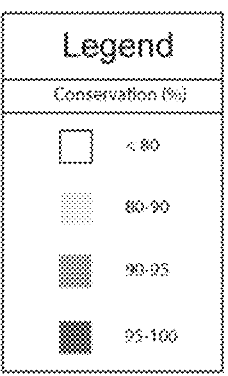
Figure 2:
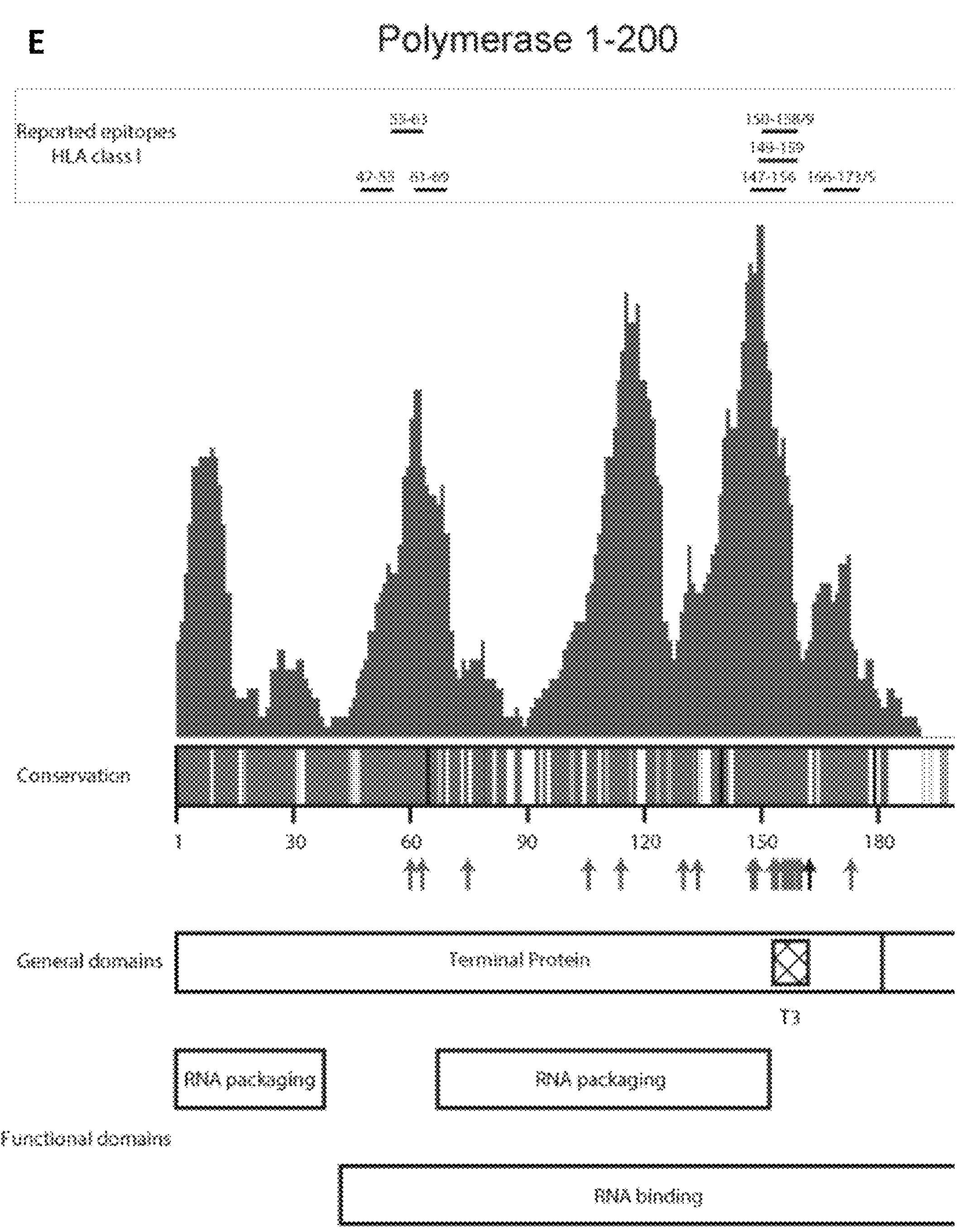
Figure 2:
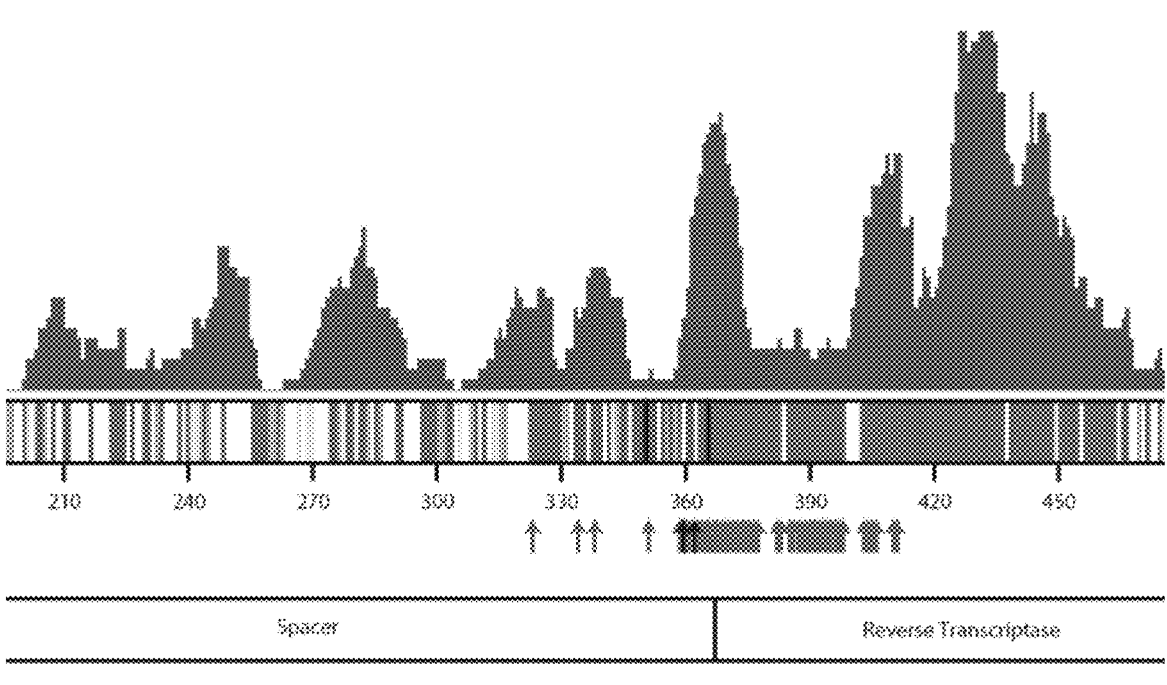
Figure 2:
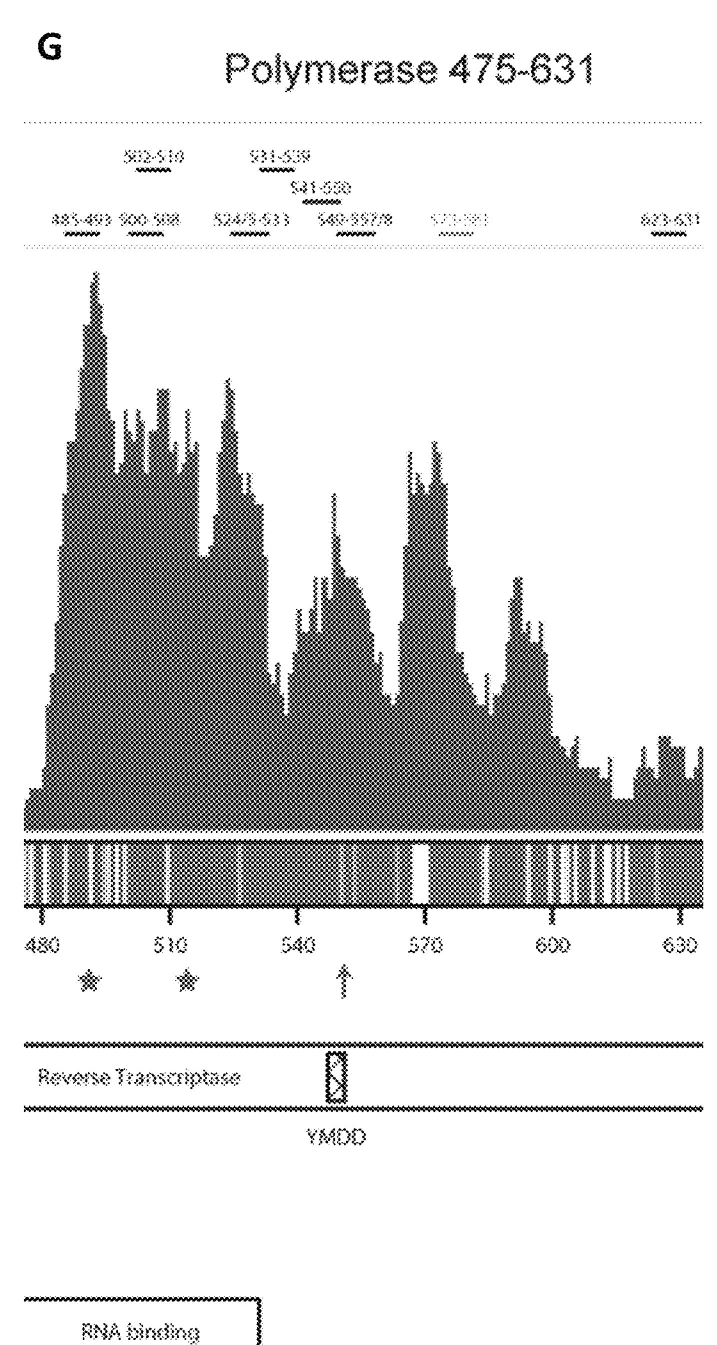
Figure 2:
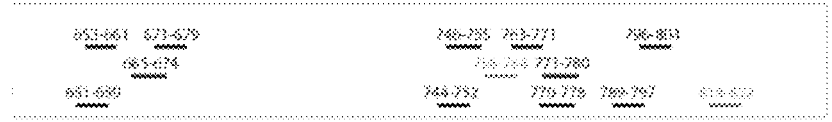
Figure 2:
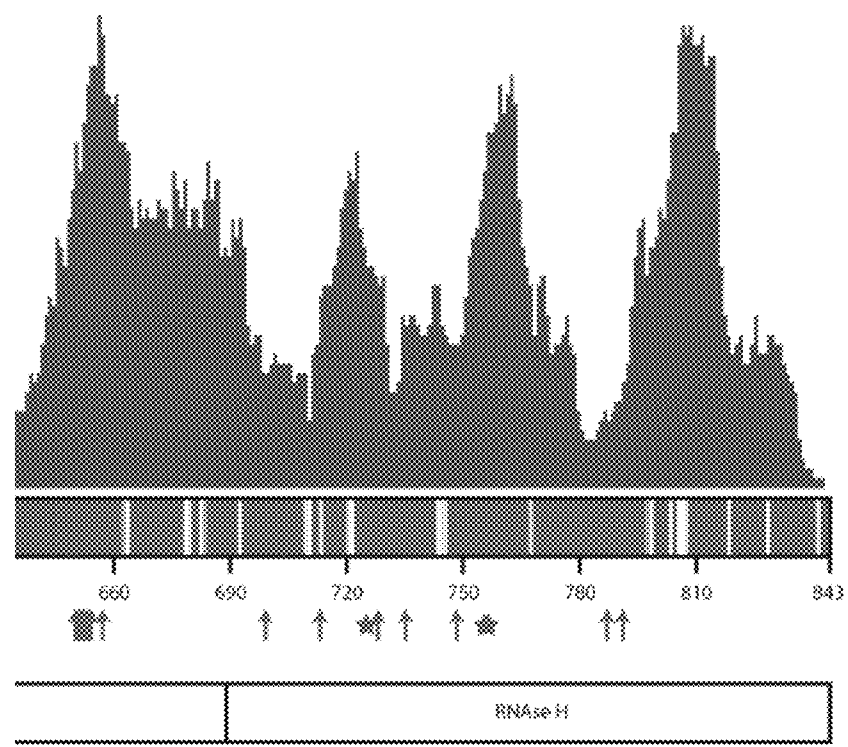
Figure 2:
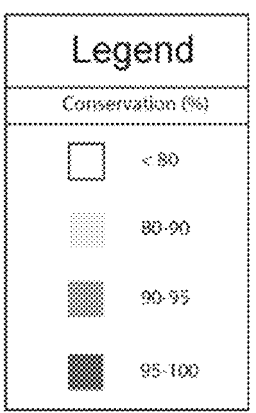

In addition, amino acids that alone or in combination were previously associated with loss of viral replication were aligned to the consensus sequence (FIGS. 1 and 2). Functionally associated amino acids were more numerous for Pol compared to HBV-X. Therefore, an additional threshold of ≥50% loss of viral persistence for Pol was introduced to select the most crucial amino acids. Tables 1 and 2 present literature references on functional domains and amino acids.

TABLE 1 literature references reporting or reviewing experimental evidence for functional domains and essential amino acids of HBV-x.

| Position in consensus sequence (SEQ ID NO: 30) | Literature reference |
|---|---|
| Essential amino acids within HBx causing loss of viral persistence upon mutation | |

TABLE 1-continued literature references reporting or reviewing experimental evidence for functional domains and essential amino acids of HBV-x.

| Position in consensus sequence (SEQ ID NO: 30) | Literature reference |
|---|---|
| 58 | Sitterlin et al. 1997 J Virol 71:6194 |
| 61 | Kumar et al. 1996 PNAS 93:5647 |
| 63 | Becker et al. 1998 J Virol 72:266 |
| 68 | Sitterlin et al. 1997 J Virol 71:6194 |
| 69 | Kumar et al. 1996 PNAS 93:5647 |
| | Becker et al. 1998 J Virol 72:266 |
| 90 | Becker et al. 1998 J Virol 72:266 |
| | Lin-Marq et al. 2001 Virology 287:266 |
| 91 | Becker et al. 1998 J Virol 72:266 |
| | Lin-Marq et al. 2001 Virology 287:266 |
| 95, 96, 98 | Lin-Marq et al. 2001 Virology 287:266 |
| 119, 129 | Sitterlin et al. 1997 J Virol 71:6194 |
| 137 | Kumar et al. 1996, PNAS 93:5647 |
| 139 | Sitterlin et al. 1997 J Virol 71:6194 |
| Functional domains within HBx implemented in viral replication | |
| 51-72 | Tang et al. 2005 J Virol 79:5548 |
| | Murakami et al. 1994 J Biol Chem 269:15118 |
| 88-154 | Tang et al. 2005 J Virol 79:5548 |
| | Gong et al. 2013 Viruses 5:1261 |

TABLE 2 literature references reporting or reviewing experimental evidence for functional domains and essential amino acids of HBV polymerase.

| Position as mentioned in literature reference | Position in consensus sequence (SEQ ID NO: 28) | Literature reference |
|---|---|---|
| Essential amino acids within Pol causing loss of viral persistence for ≥ 50% upon mutation | | |
| 60, 63 | 60, 63 | Clark et al 2017 J Virol 91:e01785 |
| 74 | 74 | Shin et al. 2011 FEBS Lett 585:3964 |
| 105 | 105 | Shin et al. 2011 J Gen Virol 92:1809 |
| 114, 130, 133 | 114, 130, 133 | Clark et al 2017 J Virol 91:e01785 |
| 147 | 147 | Shin et al. 2011 FEBS Lett 585:3964 |
| 170, 171 | 147, 148 | Badtke et al. 2009 Virology 390:130 |
| 153 | 153 | Cao et al. 2014 J Viral Hepat 21:882 |
| | | Clark et al 2017 J Virol 91:e01785 |
| 156 | 154 | Cao et al. 2014 J Viral Hepat 21:882 |
| 155 | 155 | Cao et al. 2014 J Viral Hepat 21:882 |
| | | Clark et al 2017 J Virol 91:e01785 |
| 179, 180 | 156, 157 | Cao et al. 2014 J Viral Hepat 21:882 |
| | | Badtke et al. 2009 Virology 390:130 |
| 160 | 158 | Cao et al. 2014 J Viral Hepat 21:882 |
| 182, 160 | 159, 160 | Cao et al. 2014 J Viral Hepat 21:882 |
| | | Badtke et al. 2009 Virology 390:130 |
| 162 | 162 | Clark et al 2017 J Virol 91:e01785 |
| 173 | 173 | Shin et al. 2011 FEBS Lett 585:3964 |
| 135, 146, 150, 6 | 323, 334, 338, 352 | Kim et al. 2009 J Virol 83:8032 |
| 360 | 358 | Cao et al. 2014 J Viral Hepat 21:882 |
| 361 | 359 | Cao et al. 2014 J Viral Hepat 21:882 |
| 362, 363 | 360, 361 | Cao et al. 2014 J Viral Hepat 21:882 |
| 364 | 362 | Cao et al. 2014 J Viral Hepat 21:882 |
| 365-367 | 363-365 | Cao et al. 2014 J Viral Hepat 21:882 |
| 383, 368 | 366 | Cao et al. 2014 J Viral Hepat 21:882 |
| | | Badtke et al. 2009 Virology 390:130 |
| 369 | 367 | Cao et al. 2014 J Viral Hepat 21:882 |
| 385, 370 | 368 | Cao et al. 2014 J Viral Hepat 21:882 |
| | | Badtke et al. 2009 Virology 390:130 |
| 371-375 | 369-373 | Cao et al. 2014 J Viral Hepat 21:882 |
| 376, 391 | 374 | Cao et al. 2014 J Viral Hepat 21:882 |
| | | Badtke et al. 2009 Virology 390:130 |
| 377, 392 | 375 | Cao et al. 2014 J Viral Hepat 21:882 |
| | | Badtke et al. 2009 Virology 390:130 |
| 378 | 376 | Cao et al. 2014 J Viral Hepat 21:882 |

TABLE 2-continued literature references reporting or reviewing experimental evidence for functional domains and essential amino acids of HBV polymerase.

| Position as mentioned in literature reference | Position in consensus sequence (SEQ ID NO: 28) | Literature reference |
|---|---|---|
| 394, 379 | 377 | Cao et al. 2014 J Viral Hepat 21:882 |
| | | Badtke et al. 2009 Virology 390:130 |
| 395, 399, 400, 402 | 378, 382, 383, 385 | Badtke et al. 2009 Virology 390:130 |
| 388 | 386 | Cao et al. 2014 J Viral Hepat 21:882 |
| | | Badtke et al. 2009 Virology 390:130 |
| 404, 389 | 387 | Cao et al. 2014 J Viral Hepat 21:882 |
| | | Badtke et al. 2009 Virology 390:130 |
| 390-392 | 388-390 | Cao et al. 2014 J Viral Hepat 21:882 |
| 408, 393 | 391 | Cao et al. 2014 J Viral Hepat 21:882 |
| | | Badtke et al. 2009 Virology 390:130 |
| 409, 394 | 392 | Cao et al. 2014 J Viral Hepat 21:882 |
| | | Badtke et al. 2009 Virology 390:130 |
| 410, 395 | 393 | Cao et al. 2014 J Viral Hepat 21:882 |
| | | Badtke et al. 2009 Virology 390:130 |
| 411, 396 | 394 | Cao et al. 2014 J Viral Hepat 21:882 |
| | | Badtke et al. 2009 Virology 390:130 |
| 397 | 395 | Cao et al. 2014 J Viral Hepat 21:882 |
| 413, 398 | 396 | Cao et al. 2014 J Viral Hepat 21:882 |
| | | Badtke et al. 2009 Virology 390:130 |
| 399-404 | 397, 398, 403-406 | Cao et al. 2014 J Viral Hepat 21:882 |
| 428, 429 | 411, 412 | Badtke et al. 2009 Virology 390:130 |
| 146, 205 | 492, 515 | Xu et al. 2016 BMC Bioinformatics 17:Suppl 8:280 |
| 540 | 551 | Radziwill et al. 1990 J Virol 64:613 |
| 304, 305 | 650, 651 | Wang et al. 2007 J Med Virol 79:676 |
| 652, 306 | 652 | Lin et al. 2001 J Virol 75:11827 |
| | | Wang et al. 2007 FEBS Lett 581:558 |
| 307, 308, 311 | 653, 654, 657 | Wang et al. 2007 J Med Virol 79:676 |
| 702 | 700 | Tavis et al. 2013 PLoS Pathog 9:e1003125 |
| 703 | 714 | Ko et al. 2014 J Virol 88:154 |
| 715 | 726 | Potenza et al. 2007 Protein Expr Purif 55:93 |
| 731 | 729 | Tavis et al. 2013 PLoS Pathog 9:e1003125 |
| 718, 725 | 729, 736 | Radziwill et al. 1990 J Virol 64:613 |
| 750 | 748 | Tavis et al. 2013 PLoS Pathog 9:e1003125 |
| 737 | 748 | Radziwill et al. 1990 J Virol 64:613 |
| 744, 745 | 755, 756 | Potenza et al. 2007 Protein Expr Purif 55:93 |
| 790 | 788 | Tavis et al. 2013 PLoS Pathog 9:el003125 |
| 781 | 792 | Ko et al. 2014 J Virol 88:154 |
| Functional domains within Pol implemented in viral persistence | | |
| 1-39 | 1-39 | Clark et al 2017 J Virol 91:e01785 |
| 67-152 | 67-152 | Clark et al 2017 J Virol 91:e01785 |
| 42-196 | 42-207 | Hu and Boyer 2006 J Virol 80:2141 |
| 291-520 | 302-531 | Hu and Boyer 2006 J Virol 80:2141 |

Example 2: Prediction of Novel HLA Class I Binding Peptides Derived from HBV-x and HBV Polymerase We set out to identify novel peptides that can bind at least 1 out of 6 HLA-supertypes prevalent in Caucasians, Africans or Asians for which also in vitro assays to confirm binding were at disposal (i.e. supertypes HLA-A*01; A*02; A*03; A*24; B*07; B*08). We first predicted binders spanning 8-14 amino acids for supertype representative HLA-types using the established in silico prediction tool NetMHCpan (Nielsen and Andreatta 2016, Genome Med 8:33) to make a frequency distribution of predicted binders (FIGS. 1 and 2, grey bar diagrams). The density of all predicted binders per amino acid was similar between Pol and HBx (mean±SD Pol 16.36±12.62, HBx 15.60±9.49; Mann-Whitney; p=0.57). Predicted binders spanning 9-11 amino acids were subsequently aligned to our maps outlining conservation and function described in Example 1 (FIGS. 1 and 2) since 9-11 mers are most likely to represent a relevant epitope (Trolle et al. 2016 J Immunol 196:1480).

Figure 3:
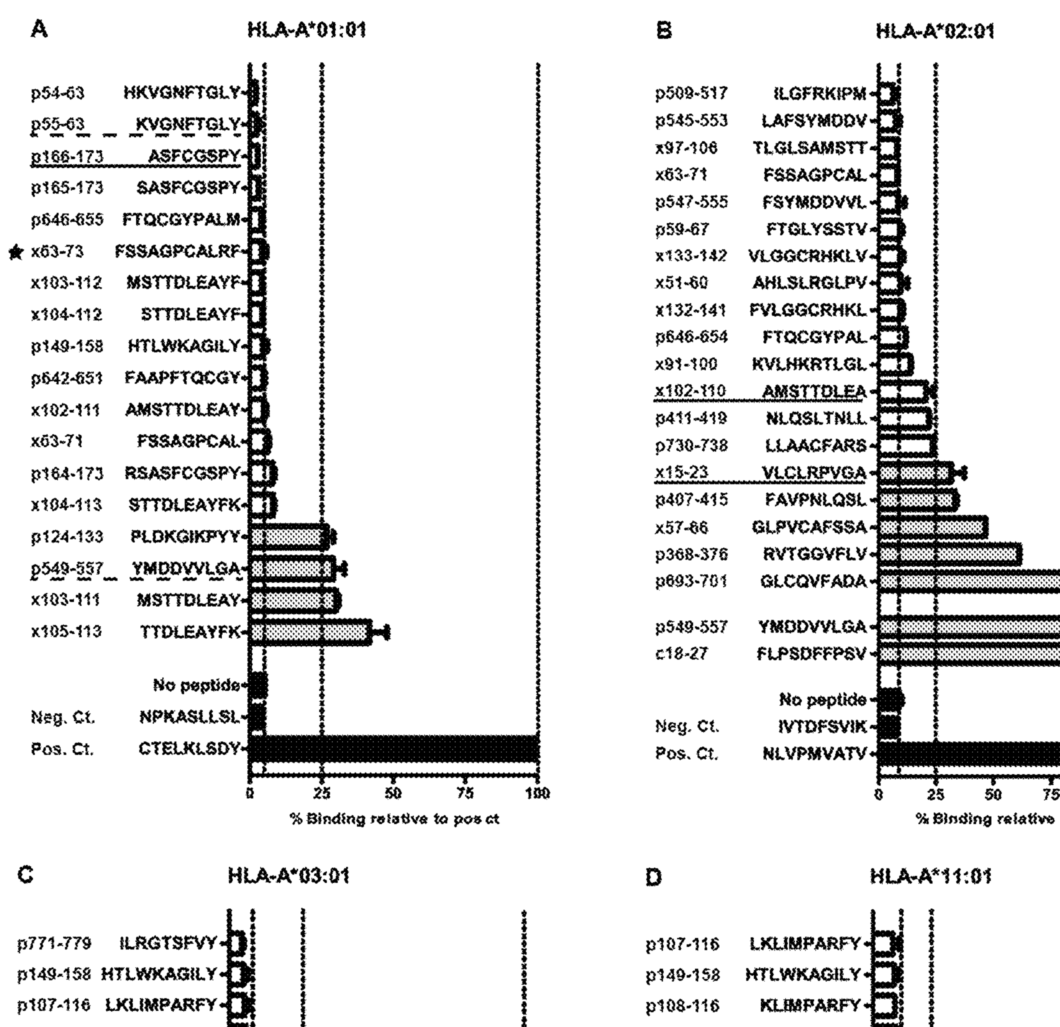
FIG. 3. In vitro binding capacity of selected predicted HLA-binding peptide sequences. Binding of predicted HLA-binding peptide sequences is represented as percent binding of positive control peptides which have a high affinity for indicated HLA-types (pos. ct.). Mean and standard deviation are depicted for controls (black), binders (>25% of positive control; grey) and non-binders (≤25% of positive control; white). Binding capacity was assessed for 6 supertype representatives and in addition HLA*11:01 was included in view of its high prevalence amongst the chronic hepatitis B patient population. These are each depicted in a separate graph (A-G). As negative control we included a known non-binding peptide for each HLA-type (neg. ct.) and a condition where no peptide was present. Closed underscored peptides are infrequently described as epitope sequences in connection with the HLA-type tested. Dotted underscored peptides are epitope sequences so far only described in connection with another HLA-type, of which cross-reactive binders are summarized in the table (H). Asterisks indicate which peptides did not meet our length and conservation thresholds.
Figure 3:
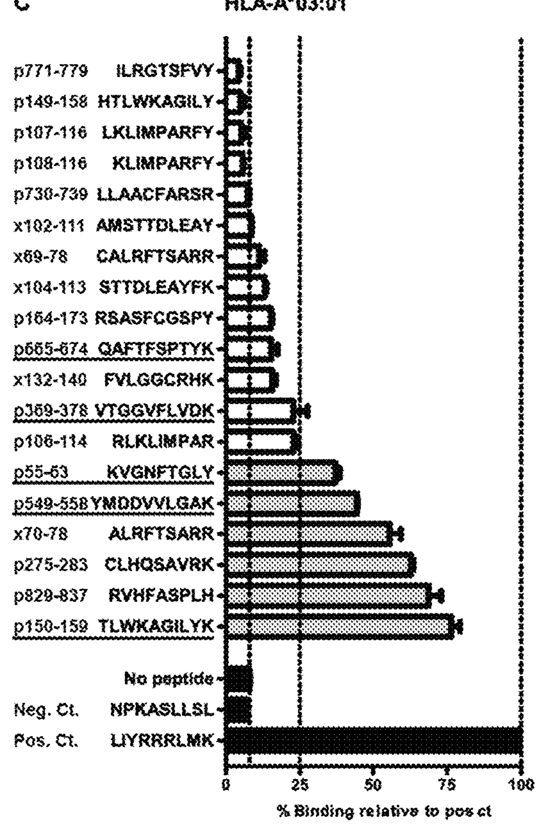
Figure 3:
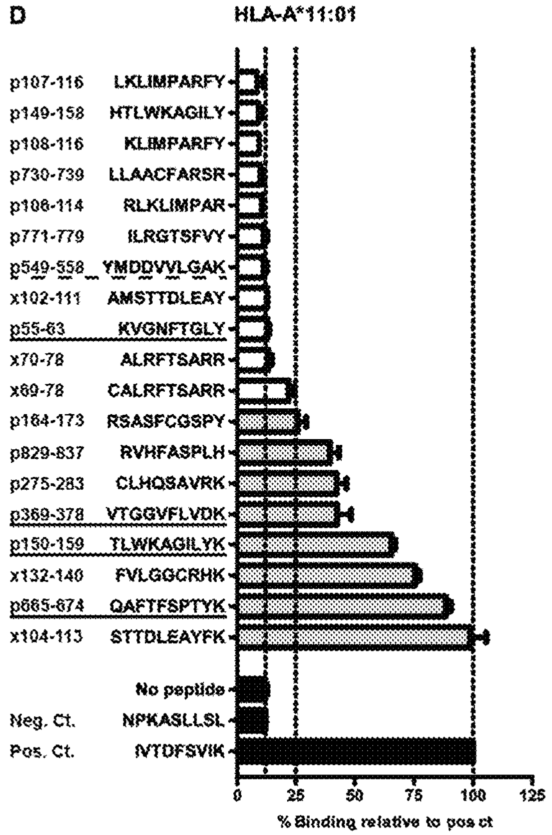
Figure 3:
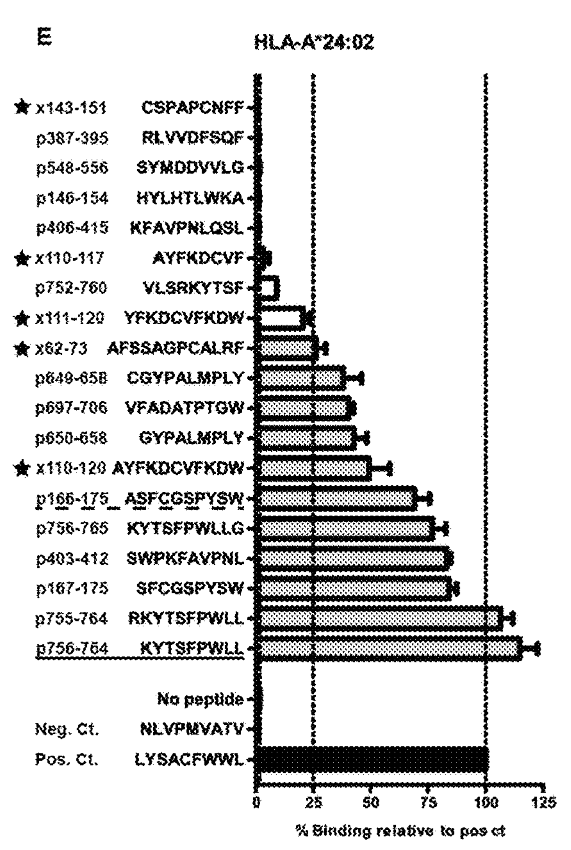
Figure 3:
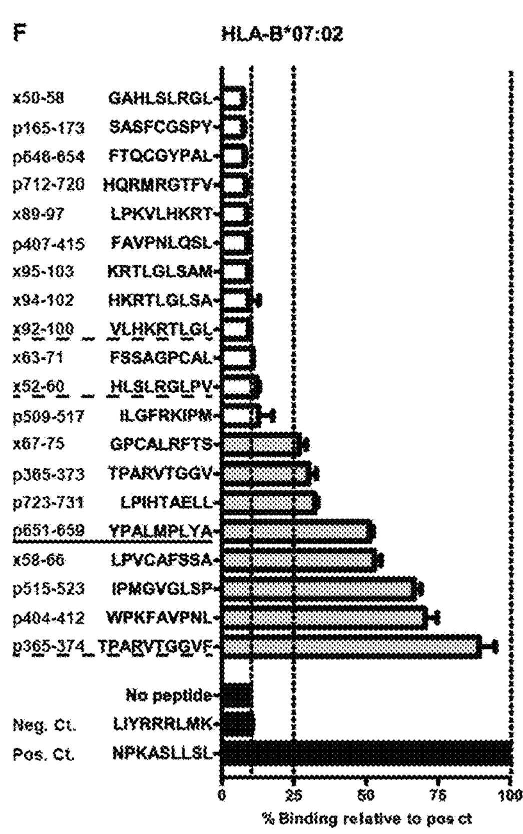
Figure 3:
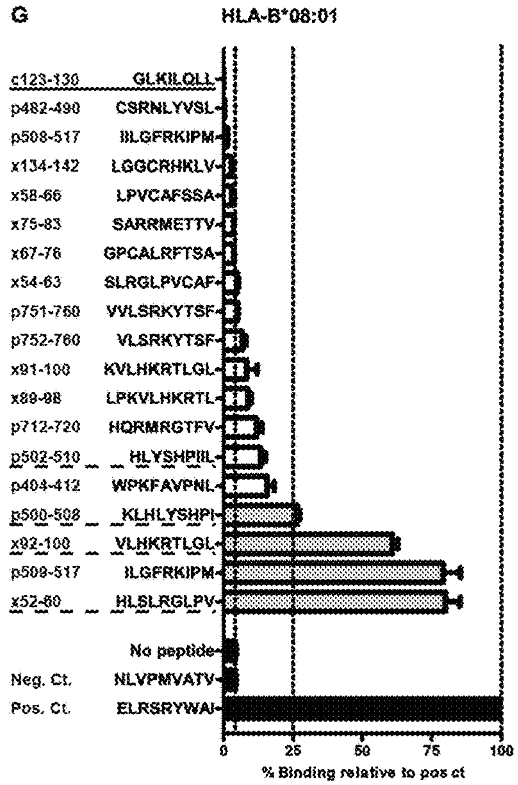

The prediction yielded a total of 251 potential novel HLA-binders for HBx and 1655 for Pol. Of these, we selected most promising peptides for validation of binding in an in vitro HLA-binding assay based on UV-induced peptide exchange (Toebes et al. 2006 Nat Med 12:246). For practical and economic reasons, we aimed to test binding of 96 unique peptide sequences over both proteins and across HLA-types. We included two well-described epitopes (Core 18-27 and Pol 549-557) to put binding capacity of our newly identified binders into context. The 96 potential binders were selected based on peptide length (9-mers preferred), predicted HLA-binding strength, conservation and functional importance of included amino acids. Not all criteria were always fulfilled for all 96 potential binders. For HLA-A*01 and HLA-A*24, there was an unsatisfactory number of predicted binders for HBx to maintain our strict thresholds for conservation and peptide length. For these conditions we therefore also included some less conserved peptides or peptides spanning 8-12 amino acids (indicated with asterisks in FIG. 3, see Example 3). In addition, we selected several peptides which were infrequently (once or twice) reported as an epitope in literature and therefore considered unestablished (FIG. 3: closed underscores, see Example 3). This included c123-130 since this was the only HBV-derived epitope registered in Hepitopes in connection with HLA-B*08. Moreover, peptides that were predicted to bind several HLA-types were prioritized throughout the selection procedure which led to a total set of 113 potential binders to test. As a whole, this selection procedure yielded 45 potential binders for HBx and 68 for Pol to validate with an in vitro binding assay. The majority of these mapped to highly conserved areas with established functional importance. The median of conservation among selected peptides was above 93% for HBx and even above 96% for Pol.

Example 3: In Vitro Binding Capacity of Selected Peptides Derived from HBx and Polymerase

3.1 Method

Synthetic peptides (Peptide 2.0 Inc) of selected potential HLA-binders were used in an in vitro binding assay as described previously (Karimzadeh et al. 2018 J Virol 92:e01891). In brief, peptide exchange reactions were performed by exposure for 30 min of conditional peptide-HLA complexes (pHLA) (0.53 μM) to long-wavelength UV using a 366 nm UV lamp (Camag) in the presence or absence of the indicated peptide (50 μM). Subsequently, the peptide exchange efficiency was analyzed using an HLA class I enzyme-linked immunosorbent assay (ELISA), which detects beta-2 microglobulin of peptide-stabilized HLA class I complexes in an exchange reaction mixture. To this end, streptavidin (2 μg/ml) was bound onto polystyrene microtiter wells (Nunc MaxiSorp). After washing and blocking, HLA complex present in exchange reaction mixtures or controls was captured by the streptavidin on the microtiter plate via its biotinylated heavy chain (incubation for 1 h at 37° C.). Nonbound material was removed by washing. Subsequently, horseradish peroxidase (HRP)-conjugated antibody to human beta-2-microglobulin (0.6 μg/ml; Sanquin Reagents B.V.) was added (incubation for 1 h at 37° C.). After removal of nonbound HRP-conjugate by washing, an ABTS [2,2'-azino-bis(3-ethylbenzothiazoline-6-sulfonic acid) diammonium salt] (Sanquin Reagents B.V.) substrate solution was added to the wells. The reaction was stopped after 8 min (incubation at room temperature) by the addition of a 2% (w/v) oxalic acid dihydrate stop solution (Sanquin Reagents B.V.) and read in a Thermo Electron Multiskan Ascent ELISA reader at 414 nm. Every peptide was independently exchanged twice. Every exchange mixture was measured in duplicate in the HLA class I ELISA. The absorbances of all the peptides were normalized to the absorbance of a known HLA allele-specific ligand with high affinity for each corresponding allele (representing 100%; Table 3). Negative controls included an HLA allele-specific non-binder and UV irradiation of the conditional HLA class I complex in the absence of a rescue peptide.

TABLE 3 reference peptides used for the in vitro binding assay classified per HLA-type.

| HLA-type | Pos ct | | Neg ct | |
|---|---|---|---|---|
| A*01:01 | Influenza A NP (44-52) | CTELKLSDY | RSV NP (306-314) | NPKASLLSL |
| A*02:01 | CMV pp65 (495-503) | NLVPMVATV | EBV EBNA3B (416-424) | IVTDFSVIK |
| A*03:01 | gp100 (614-622) | LIYRRRLMK | RSV NP (306-314) | NPKASLLSL |
| A*11:01 | EBV EBNA3B (416-424) | IVTDFSVIK | RSV NP (306-314) | NPKASLLSL |
| A*24:02 | GPR143 (126-134) | LYSACFWWL | CMV pp65 (495-503) | NLVPMVATV |
| B*07:02 | RSV NP (306-314) | NPKASLLSL | gp100 (614-622) | LIYRRRLMK |
| B*08:01 | Influenza A NP (380-388) | ELRSRYWAI | CMV pp65 (495-503) | NLVPMVATV |

3.2 Results

Binding capacity of selected peptides was tested in a plate-based in vitro binding assay as described in section 3.1. Peptides were classified as HLA-binders when their binding capacity was higher than 25% of that of a known high affinity peptide. HLA-A*11:01 and HLA-A*03:01 were both tested as members of the HLA-A*03 supertype since many HBV infected patients are Asian and HLA-A*11:01 is more prevalent in this population compared to supertype representative HLA-A*03:01 which is more prevalent in Caucasians (Chang et al 2013 Eur J Immunol 43:1109).

We identified 13 binders for HBx and 33 for Pol across HLA-supertypes (FIG. 3 Grey bars). This included novel binders that have been described previously in context of another HLA-type (FIG. 3A-G dotted underscores and 3H). Notably, both HBx- and Pol-derived binders were identified for each HLA-supertype tested. For HLA-A*02 the well-established epitopes c18-27 and p549-557 scored even better than the positive control (FIG. 3B). In contrast, binding of infrequently reported epitopes (FIG. 3: closed underscores) could not always be confirmed.

Figure 4:
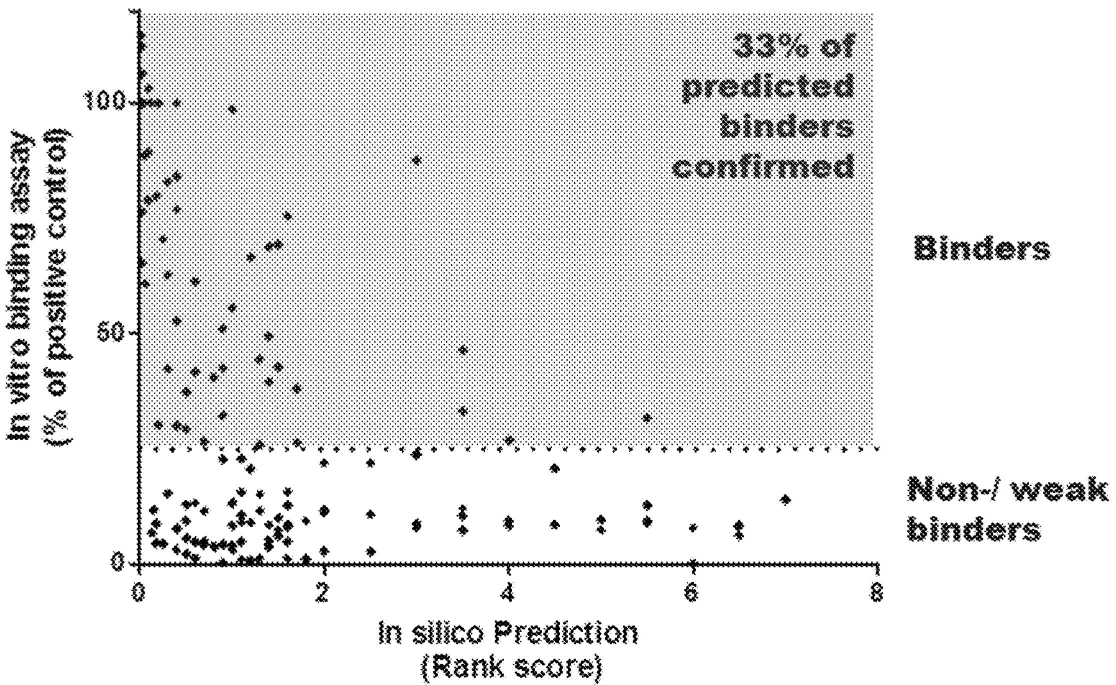
FIG. 4. Binding capacity of selected predicted HLA-binding peptide sequences versus the in silico prediction derived rank score. Binding capacity of the predicted HLA-binding sequences by in vitro HLA-binding assay as depicted in FIG. 3 is plotted against the in silico predicted HLA-binding capacity by NetMHCpan expressed as rank score. Indicated is the 25% binding of positive control cut-off to separate confirmed binders from low/non-binders.

Generally, the binding predictions were found to be fairly poor, as only a third of the predicted binders in fact had a binding capacity above the threshold. Many peptides that were predicted to bind strongly (low rank score in the in silico prediction) did not show binding above threshold in the in vitro assay (FIG. 4).

Table 4 compares predicted scores (Rank) with assay results (Bindings %) for the peptides that were tested for each HLA type.

TABLE 4

| HLA-A*01:01 | | | |
|---|---|---|---|
| Peptide | Sequence | Bindings% | Rank |
| Pos | CTELKLSDY | 100.0 | 0.04 |
| Neg | NPKASLLSL | 3.9 | 36 |
| UV | No peptide | 5.1 | |
| p166-173 | ASFCGSPY | 2.7 | 2.5 |
| x105-113 | TTDLEAYFK | 41.7 | 0.6 |
| x103-111 | MSTTDLEAY | 30.2 | 0.2 |
| p549-557 | YMDDVVLGA | 29.2 | 0.5 |
| p124-133 | PLDKGIKPYY | 26.7 | 0.7 |
| x104-113 | STTDLEAYFK | 8.0 | 1.6 |
| p164-173 | RSASFCGSPY | 7.8 | 0.4 |
| x63-71 | FSSAGPCAL | 6.2 | 1.5 |
| x102-111 | AMSTTDLEAY | 4.9 | 0.6 |
| p642-651 | FAAPFTQCGY | 4.7 | 0.175 |
| p149-158 | HTLWKAGILY | 4.4 | 0.25 |
| x104-112 | STTDLEAYF | 4.3 | 0.9 |
| x103-112 | MSTTDLEAYF | 4.1 | 1 |
| x63-73 | FSSAGPCALRF | 4.1 | 1.4 |
| p646-655 | FTQCGYPALM | 4.0 | 0.8 |
| p165-173 | SASFCGSPY | 3.1 | 0.4 |
| p55-63 | KVGNFTGLY | 2.3 | 0.5 |
| p54-63 | HKVGNFTGLY | 2.1 | 0.5 |
| HLA-A*02:01 | | | |
| Peptide | Sequence | Bindings% | Rank |
| Pos | NLVPMVATV | 100.0 | 0.40 |
| Neg | IVTDFSVIK | 7.7 | 22.00 |
| UV | No peptide | 9.0 | |
| p549-557 | YMDDVVLGA | 103.2 | 0.09 |

TABLE 4-continued

| | | | |
|---|---|---|---|
| C18-27 | FLPSDFFPSV | 112.2 | 0.02 |
| p693-701 | GLCQVFADA | 87.6 | 3.0 |
| p368-376 | RVTGGVFLV | 61.2 | 0.6 |
| x57-66 | GLPVCAFSSA | 46.5 | 3.5 |
| p407-415 | FAVPNLQSL | 33.3 | 3.5 |
| x15-23 | VLCLRPVGA | 31.7 | 5.5 |
| p730-738 | LLAACFARS | 23.7 | 3.0 |
| p411-419 | NLQSLTNLL | 21.9 | 2.5 |
| x102-110 | AMSTTDLEA | 20.7 | 4.5 |
| x91-100 | KVLHKRTLGL | 14.0 | 7.0 |
| p646-654 | FTQCGYPAL | 11.9 | 2.0 |
| x132-141 | FVLGGCRHKL | 10.4 | 3.5 |
| x51-60 | AHLSLRGLPV | 9.8 | 5.0 |
| x133-142 | VLGGCRHKLV | 9.6 | 5.0 |
| p59-67 | FTGLYSSTV | 9.4 | 1.8 |
| p547-555 | FSYMDDVVL | 8.6 | 6.5 |
| x63-71 | FSSAGPCAL | 8.2 | 6.5 |
| x97-106 | TLGLSAMSTT | 7.9 | 6.0 |
| p545-553 | LAFSYMDDV | 7.3 | 3.5 |
| p509-517 | ILGFRKIPM | 6.2 | 6.5 |
| HLA-A*03:01 | | | |
| Peptide | Sequence | Bindings% | Rank |
| Pos | LIYRRRLMK | 100.0 | 0.01 |
| Neg | NPKASLLSL | 7.0 | 48 |
| UV | No peptide | 8.0 | |
| p665-674 | QAFTFSPTYK | 15.3 | 0.3 |
| p150-159 | TLWKAGILYK | 76.3 | 0.02 |
| p829-837 | RVHFASPLH | 68.8 | 1.4 |
| p275-283 | CLHQSAVRK | 62.7 | 0.3 |
| x70-78 | ALRFTSARR | 55.6 | 1 |
| p549-558 | YMDDVVLGAK | 44.5 | 1.3 |
| p55-63 | KVGNFTGLY | 37.3 | 0.5 |
| p106-114 | RLKLIMPAR | 22.9 | 1.1 |
| p369-378 | VTGGVFLVDK | 22.8 | 0.9 |
| x132-140 | FVLGGCRHK | 15.6 | 1.6 |
| p164-173 | RSASFCGSPY | 15.2 | 1.3 |
| x104-113 | STTDLEAYFK | 13.1 | 1 |
| x69-78 | CALRFTSARR | 11.2 | 2 |
| x102-111 | AMSTTDLEAY | 8.6 | 1.6 |
| p730-739 | LLAACFARSR | 7.4 | 1.5 |

TABLE 4-continued

| | | | |
|---|---|---|---|
| p108-116 | KLIMPARFY | 5.7 | 0.5 |
| p107-116 | LKLIMPARFY | 5.2 | 1.4 |
| p149-158 | HTLWKAGILY | 4.9 | 1.1 |
| p771-779 | ILRGTSFVY | 4.3 | 0.7 |
| HLA-A*11:01 | | | |
| Peptide | Sequence | Bindings% | Rank |
| Pos | IVTDFSVIK | 100.0 | 0.12 |
| Neg | NPKASLLSL | 12.2 | 45 |
| UV | No peptide | 12.0 | |
| p665-674 | QAFTFSPTYK | 88.5 | 0.05 |
| x104-113 | STTDLEAYFK | 98.7 | 1 |
| x132-140 | FVLGGCRHK | 75.5 | 1.6 |
| p150-159 | TLWKAGILYK | 65.4 | 0.02 |
| p369-378 | VTGGVFLVDK | 42.5 | 0.9 |
| p275-283 | CLHQSAVRK | 42.3 | 0.3 |
| p829-837 | RVHFASPLH | 39.5 | 1.4 |
| p164-173 | RSASFCGSPY | 25.9 | 1.3 |
| x69-78 | CALRFTSARR | 22.0 | 2 |
| x70-78 | ALRFTSARR | 13.4 | 1 |
| p55-63 | KVGNFTGLY | 12.9 | 0.5 |
| x102-111 | AMSTTDLEAY | 12.8 | 1.6 |
| p549-558 | YMDDVVLGAK | 11.5 | 1.3 |
| p771-779 | ILRGTSFVY | 11.5 | 0.7 |
| p106-114 | RLKLIMPAR | 10.7 | 1.1 |
| p730-739 | LLAACFARSR | 9.9 | 1.5 |
| p108-116 | KLIMPARFY | 9.3 | 0.5 |
| p149-158 | HTLWKAGILY | 9.1 | 1.1 |
| p107-116 | LKLIMPARFY | 8.5 | 1.4 |
| HLA-A*24:02 | | | |
| Peptide | Sequence | Bindings% | Rank |
| Pos | LYSACFWWL | 100.0 | 0.2 |
| Neg | NLVPMVATV | 1.2 | 13 |
| UV | No peptide | 1.7 | |
| p756-764 | KYTSFPWLL | 114.7 | 0.01 |
| p755-764 | RKYTSFPWLL | 106.4 | 0.025 |
| p167-175 | SFCGSPYSW | 84.0 | 0.4 |
| p403-412 | SWPKFAVPNL | 83.0 | 0.3 |
| p756-765 | KYTSFPWLLG | 76.9 | 0.4 |
| p166-175 | ASFCGSPYSW | 69.2 | 1.5 |
| x110-120 | AYFKDCVFKDW | 49.4 | 1.4 |

TABLE 4-continued

| | | | |
|---|---|---|---|
| p650-658 | GYPALMPLY | 42.7 | 1.5 |
| p697-706 | VFADATPTGW | 40.4 | 0.8 |
| p649-658 | CGYPALMPLY | 38.1 | 1.7 |
| x62-73 | AFSSAGPCALRF | 26.3 | 1.7 |
| x111-120 | YFKDCVFKDW | 20.6 | 1.2 |
| p752-760 | VLSRKYTSF | 9.0 | 1.2 |
| x110-117 | AYFKDCVF | 3.1 | 1 |
| p406-415 | KFAVPNLQSL | 1.2 | 1.6 |
| p146-154 | HYLHTLWKA | 1.2 | 1.3 |
| p548-556 | SYMDDVVLG | 1.1 | 1.8 |
| p387-395 | RLVVDFSQF | 1.0 | 1.1 |
| x143-151 | CSPAPCNFF | 0.8 | 1.2 |
| HLA-B*07:02 | | | |
| Peptide | Sequence | Bindings% | Rank |
| Pos | NPKASLLSL | 100.0 | 0.04 |
| Neg | LIYRRRLMK | 10.3 | 16 |
| UV | No peptide | 9.2 | |
| p365-374 | TPARVTGGVF | 89.3 | 0.09 |
| p404-412 | WPKFAVPNL | 70.5 | 0.25 |
| p515-523 | IPMGVGLSP | 66.6 | 1.2 |
| x58-66 | LPVCAFSSA | 52.8 | 0.4 |
| p651-659 | YPALMPLYA | 51.1 | 0.9 |
| p723-731 | LPIHTAELL | 32.3 | 0.9 |
| p365-373 | TPARVTGGV | 30.1 | 0.4 |
| x67-75 | GPCALRFTS | 26.9 | 4 |
| p509-517 | ILGFRKIPM | 12.8 | 5.5 |
| x52-60 | HLSLRGLPV | 12.1 | 3.5 |
| x63-71 | FSSAGPCAL | 10.8 | 2.5 |
| x92-100 | VLHKRTLGL | 9.4 | 4 |
| x94-102 | HKRTLGLSA | 9.3 | 5.5 |
| x95-103 | KRTLGLSAM | 9.0 | 5.5 |
| p407-415 | FAVPNLQSL | 8.7 | 3 |
| x89-97 | LPKVLHKRT | 8.6 | 4.5 |
| p712-720 | HQRMRGTFV | 8.3 | 4 |
| p646-654 | FTQCGYPAL | 7.9 | 3 |
| p165-173 | SASFCGSPY | 7.4 | 5 |
| x50-58 | GAHLSLRGL | 7.4 | 3.5 |
| HLA-B*08:01 | | | |
| Peptide | Sequence | Bindings% | Rank |
| Pos | ELRSRYWAI | 100.0 | 0.01 |

TABLE 4-continued

| | | | |
|---|---|---|---|
| Neg | NLVPMVATV | 4.2 | 8.5 |
| UV | No peptide | 4.1 | |
| c123-130 | GLKILQLL | 0.0 | 6 |
| x52-60 | HLSLRGLPV | 79.8 | 0.175 |
| p509-517 | ILGFRKIPM | 78.9 | 0.09 |
| x92-100 | VLHKRTLGL | 60.8 | 0.06 |
| p500-508 | KLHLYSHPI | 26.5 | 0.7 |
| p404-412 | WPKFAVPNL | 15.6 | 1.1 |
| p502-510 | HLYSHPIIL | 13.3 | 0.6 |
| p712-720 | HQRMRGTFV | 11.8 | 0.15 |
| x89-98 | LPKVLHKRTL | 8.7 | 0.175 |
| x91-100 | KVLHKRTLGL | 8.3 | 1 |
| p752-760 | VLSRKYTSF | 6.7 | 0.125 |
| p751-760 | VVLSRKYTSF | 5.0 | 0.7 |
| x54-63 | SLRGLPVCAF | 4.8 | 1.6 |
| x67-76 | GPCALRFTSA | 3.7 | 0.8 |
| x75-83 | SARRMETTV | 3.6 | 1.4 |
| x58-66 | LPVCAFSSA | 2.9 | 2 |
| x134-142 | LGGCRHKLV | 2.8 | 2 |
| p508-517 | IILGFRKIPM | 1.3 | 0.6 |
| p482-490 | CSRNLYVSL | 0.3 | 0.9 |

Example 4: Immunogenicity of Selected HLA-Binding Peptides 4.1 Method

Peptides scoring higher than 25% binding in the in vitro HLA-binding assay were assessed for immunogenicity. Briefly, PBMCs were isolated by Ficoll (GE Healthcare) density centrifugation from buffy coats of 9 donors who have previously resolved HBV. Buffy coats were provided by the local blood bank with corresponding 2-digit HLA-types. 4-digit HLA typing was performed in 7 out of 9 donors using Global Screening Array (GSA) (Illumina through Human Genomics Facility Erasmus MC Rotterdam) (Table 5).

TABLE 5

HLA-1 types of HBV resolver donors used for immunogenicity testing of HLA-binders:

| | HLA-A | HLA-B | HLA-C |
|---|---|---|---|
| Donor 1 | 03:01 | 07:02 | 07:02 |
| | 02:01 | 07:02 | 07:02 |
| Donor 2* | 01 | 08 | 06 |
| | 11 | 13 | 07 |
| Donor 3 | 02:01 | 18:01 | 12:03 |
| | 25:01 | 07:02 | 07:02 |
| Donor 5 | 01:01 | 08:01 | 07:01 |
| | 24:02 | 07:02 | 07:02 |
| Donor 6 | 01:01 | 08:01 | 07:01 |

TABLE 5-continued

HLA-1 types of HBV resolver donors used for immunogenicity testing of HLA-binders:

| | HLA-A | HLA-B | HLA-C |
|---|---|---|---|
| | 02:01 | 40:01 | 03:04 |
| Donor 7 | 03:01 | 52:01 | 02:02 |
| | 11:01 | 51:01 | 12:02 |
| Donor 8 | 23:01 | 49:01 | 07:01 |
| | 11:01 | 18:01 | 12:02 |
| Donor 9* | 24 | 15 | 01 |
| | 31 | 22 | 14 |
| Donor 10 | 01:01 | 07:02 | 07:01 |
| | 02:01 | 44:02 | 07:02 |

*HLA type available only in 2-digits

All donors gave written informed consent. PBMCs were cultured in IMDM (Lonza)+2% human serum (Sanquin)+50 IU/ml hIL-2 (Miltenyi) in presence of peptide pools of max 5 peptides of interest based on HLA-matching at 10 μg/ml/peptide. After 14 days, 200.000 cells were re-stimulated with peptides of interest for 48 hr at 37° C. with 10 μg/ml/peptide in triplicate. Supernatants of re-stimulations were subsequently used in an hIFNγ ELISA (BioLegend) according to manufacturer's instructions. Plates were read at 450 nm wavelength using an Infinite 200Pro ELISA reader. hIFNγ levels were calculated from background-subtracted OD values (mean of triplicates) using a supernatant derived from a previously successful re-stimulation with c18-27 that was quantified in a separate ELISA using the hIFNγ standard provided by the manufacturer. HLA-binders with a mean OD value of at least the mean+2×SD of the DMSO control were quantified.

4.2 Results

Figure 5:
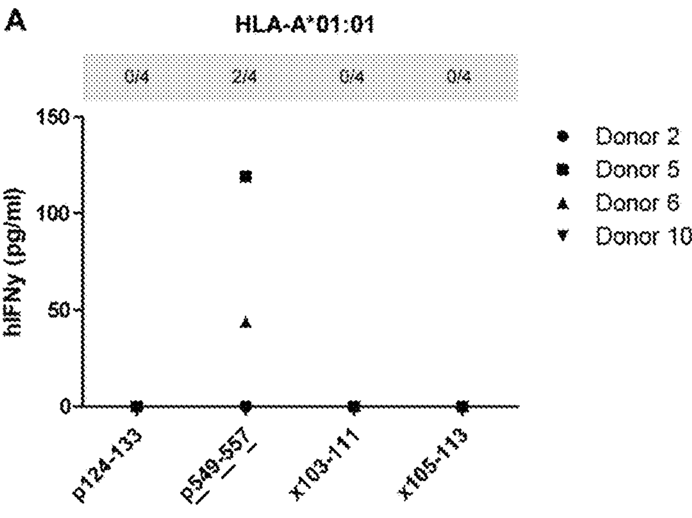
FIG. 5. Immunogenicity of HLA-binding peptide sequences. IFNγ production (DMSO subtracted) by expanded PBMCs from 9 HBV resolvers was measured in response to incubation with the confirmed HLA-binding peptide sequences and the well-established c18-27 and p549-557 epitope sequences (panel B). Grey boxes present the number of responsive donors as fraction of the total number of subjects tested for each HLA-binding peptide sequence. Closed underscored epitope sequences are infrequently described for the HLA-type tested. Dotted underscored epitope sequences are so far only described in connection with another HLA-type. Asterisks indicate which HLA-binding peptide sequences did not meet our length and conservation thresholds.
Figure 5:
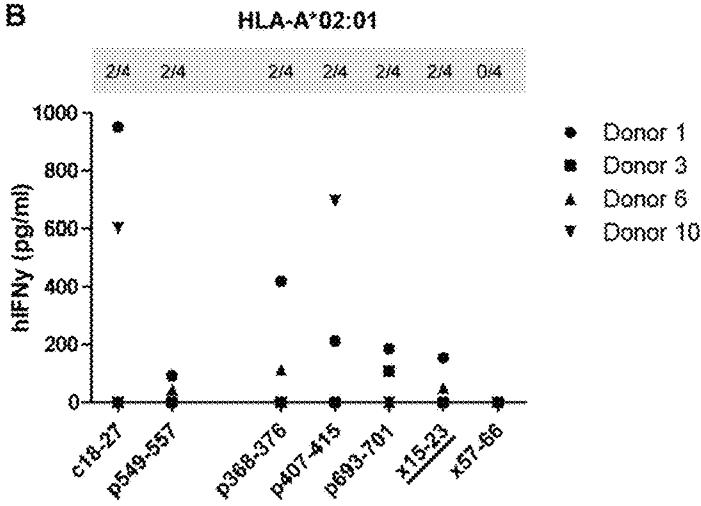
Figure 5:
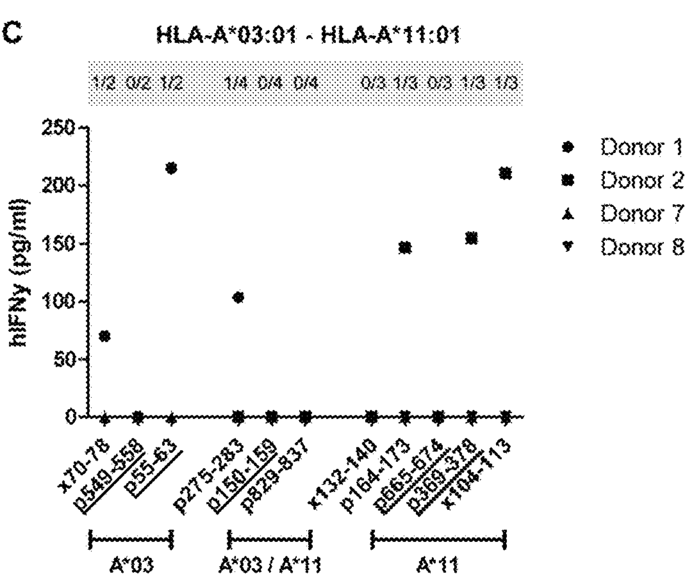
Figure 5:
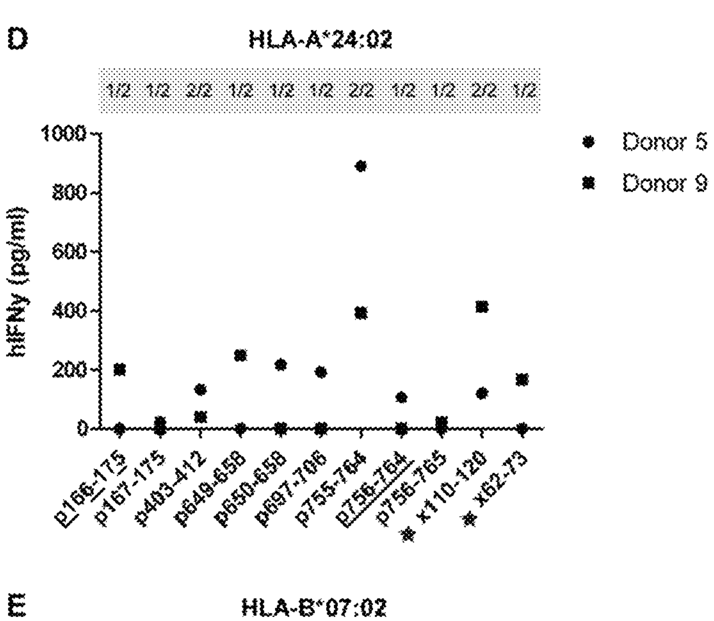
Figure 5:
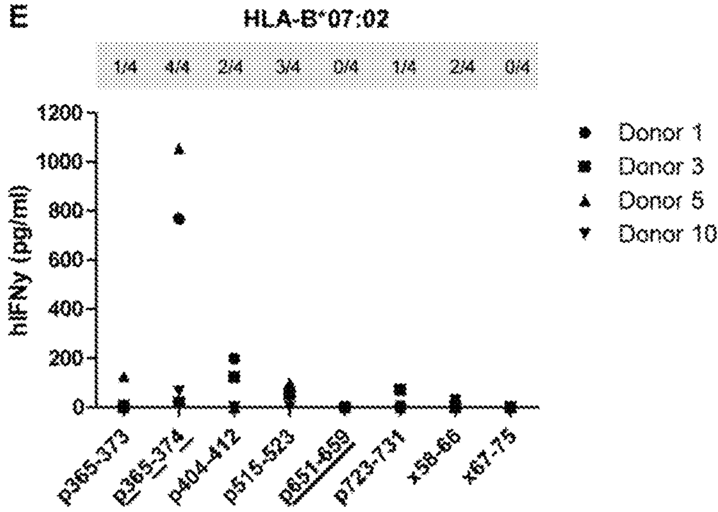
Figure 5:
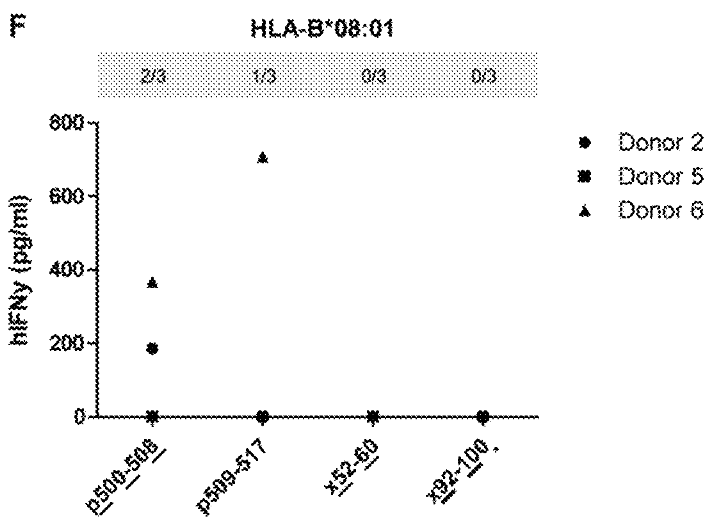

Subsequently, it was tested whether immunogenicity of HBx- and Pol-derived binders could be confirmed. PBMCs from blood donors that had previously resolved an HBV infection were expanded for 2 weeks in presence of peptide pools followed by a single peptide re-stimulation and an IFNγ ELISA as described in section 4.1. As expected, IFNγ production was detected in response to well-established epitopes c18-27 and p549-557 (FIG. 5B). IFNγ production was highly variable and some donors generally seemed to respond better than others (FIG. 5). In total we observed responses against 5 completely novel HBx- and 17 novel Pol-derived peptides. Additionally, we observed IFNγ production in response to 1 HBx- and 3 Pol-derived epitope(s) that have been infrequently described previously although none of these responses were very high (FIG. 5; closed underscore). Importantly, 4 additional Pol-derived epitopes elicited responses in donors negative for the HLA-type these epitopes were previously described for (FIG. 5; dotted underscore and table 3), indicating these peptide sequences are epitopes in multiple HLA-types. There was no measurable response to 6 Pol-derived and 7 HBx-derived HLA-binders in any of the donors tested (FIG. 5; grey boxes), but this could be due to the small number of donors. Thus, future testing of further donors might confirm immunogenicity of these HLA-binders.

Example 5

5.1 Method

To assess whether the claimed peptide fragments are immunogenic in a human setting, seven SLPs containing one or more of the epitope peptide sequences were designed, manufactured and tested using PBMC samples from fifteen different donors that have cleared an HBV infection in the past.

Design of the seven SLPs was based on 1) a naturally occurring HBV-X of HBV polymerase genotype sequence, 2) good manufacturability predicted using an in silico machine learning algorithm that was based on general synthesis principles amongst others the principle described herein above and trained with a large set of real peptide synthesis yields and 3) containing one or more of the epitope peptide sequences (see Table 6). The preferred length of the SLP was set at 25 AA. Where deemed necessary, in view of predicted bad manufacturability based on established peptide synthesis experience, flanked regions along the corresponding HBV-X or HBV polymerase sequence were included to increase manufacturability. Resulting in six SLPs of 25 AA and one SLP of 26 AA in length.

The individual SLPs (Table 6) were synthesized using solid phase Fmoc/$^{t}$Bu chemistry, treated with a cleavage cocktail, purified by HPLC and analyzed by UPLC-MS according to established methods. All reagents and solvents for solid phase peptide synthesis (SPPS) were purchased from Merck, Sigma Aldrich, Actu-All, Bachem and Biosolve, GL Biochem and used as received. Peptides synthesis was performed on a Tetras peptide synthesizer (Advanced ChemTech). The resin was dried, cooled and treated with a trifluoroacetic acid (TFA) based cleavage cocktail. After filtration of the resin, the reaction mixture was shaken at room temperature. Subsequently, the peptide was precipitated in an ether-based solution, centrifuged and the supernatant was removed. The solid precipitate was resuspended in an ether-based solution, centrifuged and the supernatant was removed. The resulting pellet was dissolved in a $H_2O$ based mixture with acetonitrile (ACN) and TFA or with acetic acid and lyophilized overnight. After purification by HPLC, based on a solvent system of TFA in $H_2O$ and TFA in ACN or TFA in $H_2O$ and TFA in ACN with tert-butanol, the selected purified fractions were pooled and lyophilized overnight. The identity and purity of the pure peptides were determined by UPLC-MS. Before use, SLPs were reconstituted in 10% DMSO and 90% $H_2O$ to achieve a concentration of 2 mM.

An IFNγ ELISpot assay was used to test the ability of SLPs to induce IFNγ production by PBMCs after 24-hour stimulation. In short, PBMCs were isolated by density gradient centrifugation from buffy coats of 15 HLA-typed donors who have previously cleared an HBV infection (Sanquin Blood bank). PBMCs were cultured in a PVDF-plate (MSIPS4510, Millipore) coated with the IFNγ-catching antibody (5 ug/ml, Mab-1-D1K, Mabtech) in the presence of 10 uM SLP or equivalent DMSO control. Cells were seeded in four replicate wells at a density of 200.000 cells per well in IMDM+8% human serum. After 20-24 hours incubation the IFNγ-detection antibody (0.3 ug/ml, Mab-7-B6-1-Biotin, Mabtech) was added followed by streptavidin-ALP (1 ug/ml, Mabtech). Development of the spots was performed by the addition of BCIP/NBT-plus substrate (100 ul/well, Mabtech) and the spots were counted with a CTL Immunospot S6 Ultimate Analyzer (Immunospot). The number of spot forming units (SFU) from four replicate wells were added and the cumulative number of spots in four replicate DMSO control wells was subtracted.

5.2 Results

Figure 6:
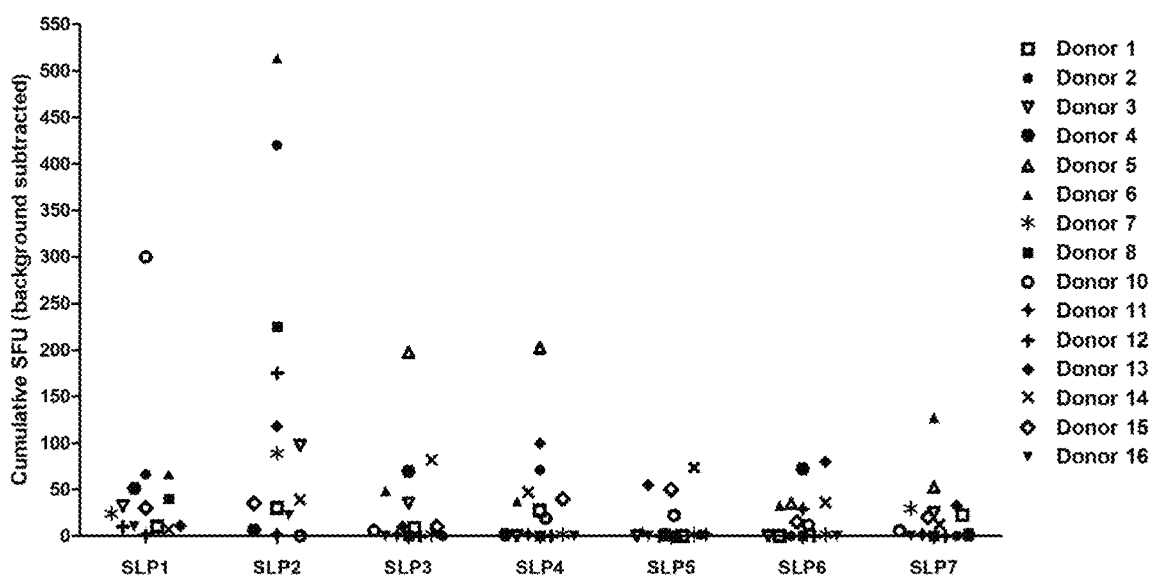
FIG. 6. IFNγ response after SLP stimulation measured by ELISpot. PBMCs from 15 donors, who have resolved an HBV infection in the past, were incubated with 10 uM SLP or equivalent concentration of DMSO for 20-24 hours and subsequent IFNγ production was measured by ELISpot. Depicted is the cumulative spot forming units (SFU) from 4 replicate wells subtracted by the cumulative SFU from 4 replicate wells of the DMSO control condition. Each dot represents one donor and every donor is depicted with a different symbol. Negative SFU are depicted as 0. Donor numbers in FIG. 6 do not necessarily correspond to donor numbers in FIG. 5.

To test the capacity of SLPs to induce IFNγ responses an IFNγ ELISpot assay was performed on PBMCs from 15 HBV revolvers. These donors have resolved an HBV infection in the past and therefore are expected to possess an HBV-specific T cell response. All SLPs, derived from both polymerase and HBx, were capable of inducing an IFNγ response (FIG. 6).

TABLE 6

| SEQ-ID | Peptide fragment sequence | Peptide fragment reference position | Epitope peptide position reference | Epitope peptide sequence |
|---|---|---|---|---|
| SLP1 | HLSLRGLPVCAFSSAGPCALRFTSA | HBx 52-76 | x57-66 | GLPVCAFSSA |
| | | | x58-66 | LPVCAFSSA |
| | | | x62-73 | AFSSAGPCALRF |
| | | | x67-75 | GPCALRFTS |
| SLP2 | LSAMSTTDLEAYFKDCLFKDWEELG | HBx 100-124 | x103-111 | MSTTDLEAY |
| | | | x104-113 | STTDLEAYFK |
| | | | x105-113 | TTDLEAYFK |
| | | | x110-120 | AYFKDCVFKDW |
| SLP3 | ASSSSSCLHQSAVRKAAYSHLSTSK | Pol 269-292 | p275-283 | CLHQSAVRK |
| SLP4 | RKLHLYSHPIILGFRKIPMGVGLSP | Pol 499-523 | p509-517 | ILGFRKIPM |
| | | | p515-523 | IPMGVGLSP |
| SLP5 | GFAAPFTQCGYPALMPLYACIQAKQA | Pol 641-666 | p649-658 | CGYPALMPLY |
| | | | p650-658 | GYPALMPLY |
| SLP6 | ARQRPGLCQVFADATPTGWGLAIGH | Pol 688-712 | p693-701 | GLCQVFADA |
| | | | p697-706 | VFADATPTGW |
| SLP7 | SPSVPSHLPDRVHFASPLHVAWRPP | Pol 819-843 | p829-837 | RVHFASPLH |

Example 6. Novel SLPs can Boost Functional CD8+ and CD4+ T Cell Responses In Vitro in Leukocytes from HBV Resolvers and Chronic HBV Patients 6.1 Methods The functional booster capacity of the novel SLPs was tested in expansion experiments. In brief, PBMCs were isolated either from buffy coats derived from healthy donors who previously cleared HBV (n=6) or from blood of chronic HBV patients who visited the outpatient clinic of the Erasmus Medical Center Rotterdam (n=5). PBMCs were cultured in IMDM (Lonza)+2% human serum (Sanquin) in the presence of SLP pools (3 uM per SLP) for 14 days. After 2 days 50 IU/ml IL-2 was added to the culture, which was repeated 3 times per week till day 14. After 14 days, 200.000 cells per well were restimulated with the individual SLPs (10 uM per SLP) or DMSO as vehicle control in quadruple. After 22 hours supernatant was harvested for cytokine analysis and the cells were used for flowcytometric analysis. Cells were pooled and stained for 30 minutes at 4° C. in the dark with the following panel; CD3 (SK7) and CD8 (RPA-T8) from eBiosciences, CD4 (SK3) from BD, CD69 (FN50) and CD107a (H4A3) from Biolegend and LIVE/DEAD Green from Invitrogen, acquired on a BD FACSCanto instrument and analyzed using FlowJo v10 (BD). Percentages of marker expression were determined by subtracting the percentage observed in the DMSO control for the corresponding marker. Secreted cytokines in culture supernatant were determined using Luminex technology. Cytokines were analyzed with a custom Procarta plate of ThermoFisher and analyzed using the MAGPIX instrument (Merck Millipore). Quantities of secreted cytokines were calculated using the standard. Background subtraction was performed by subtracting the calculated values by: Average (DMSO and irrelevant peptide)+2× SD (DMSO and irrelevant peptide).

6.2 Results

Figure 7:
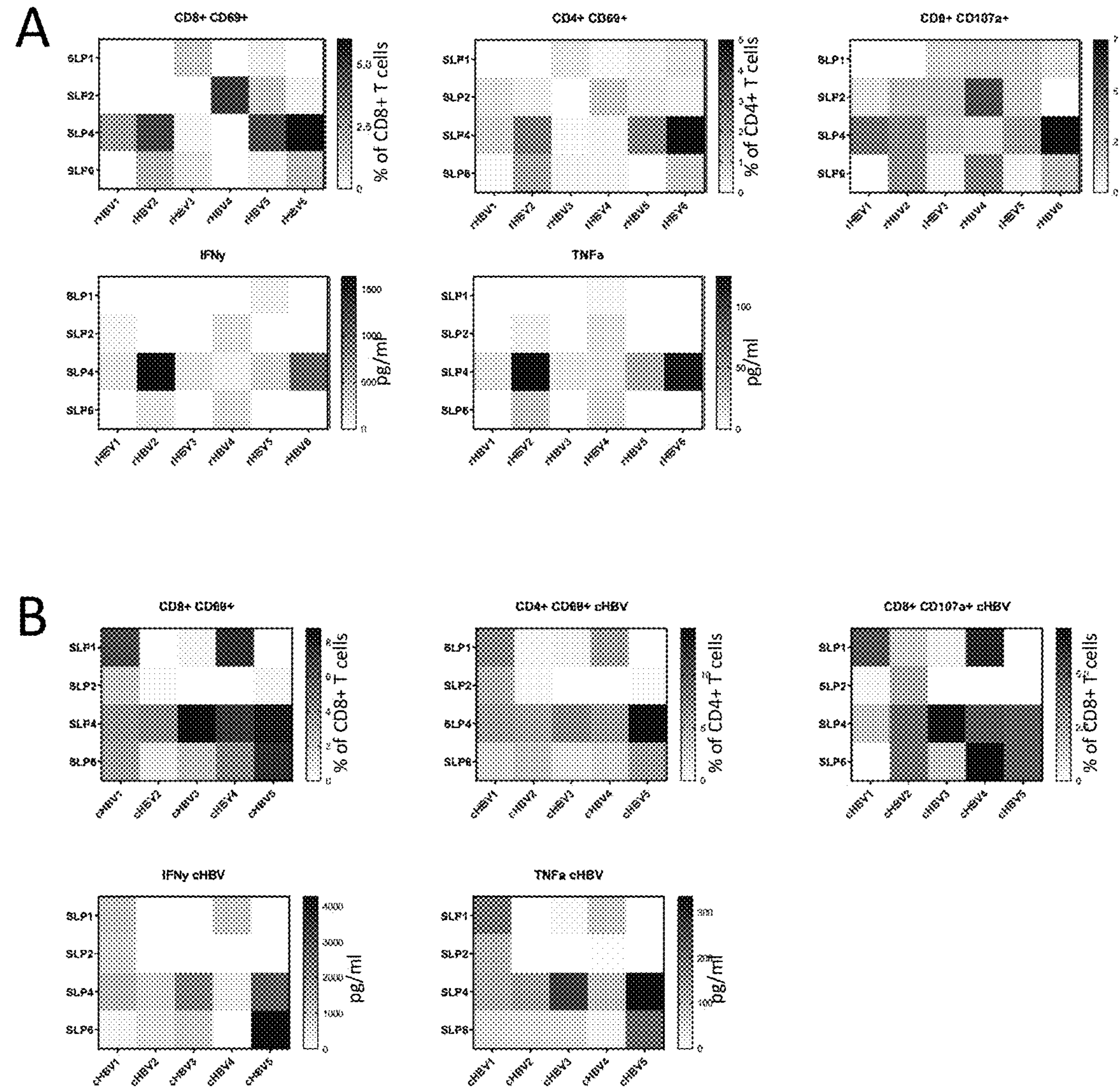
FIG. 7. Novel SLPs can boost functional CD8+ and CD4+ T cell responses in vitro in leukocytes from HBV resolvers and chronic HBV patients. Isolated PBMCs from buffy coats of healthy donors that previously cleared HBV, rHBV, (A) or PBMCs isolated from whole blood of chronic HBV patients visiting our outpatient clinic, cHBV, (B) were exposed to SLP pools containing the indicated SLPs (1, 2, 4 and 6) and allowed to expand for 14 days in the presence of IL-2. After 14 days, expanded cells were restimulated with the indicated SLP individually for 22 hours after which both cells and culture supernatants were assessed for surface makers and cytokines, respectively, indicative of functional T cell activation. Shown is the percentage of CD4+ and CD8+ T cells expressing activation marker CD69 and the percentage of CD8+ T cells expressing CD107a that is indicative of recent CD8+ T cells cytotoxic activity (subtracted by percentages observed for DMSO vehicle control samples). Also plotted is secretion of T cell cytokines IFNγ and TNFα in the supernatant as a result of SLP restimulation. Cytokine values were subtracted by the mean value observed for DMSO/irrelevant peptide control samples+2× the standard deviation of these controls.

In vitro expansion experiments mimicking vaccination indicate that all four novel SLPs (SLP1, SLP2, SLP4 and SLP6) are able to boost functional CD8+ and CD4+ T cell responses in vitro in leukocytes from HBV resolvers (rHBV1-6) and chronic HBV patients (cHBV1-5), as each of the SLPs triggered a response in at least one donor. T cell activation was demonstrated by the increased presence of CD69 on both cell types in response to SLPs (FIG. 7). That this donor T cell expansion and activation also produced functional T cells was demonstrated by the fact that CD8+ T cells displayed CD107a in response to SLPs indicating recent secretion of cytotoxic agents and by the presence of Type I T cell cytokines IFNγ and TNFα that are essential for T cell effector function.

The invention claimed is:

1. An immunogenic composition comprising:

a peptide comprising a fragment of an HBV protein, wherein said fragment is no more than 34 amino acids in length and wherein said fragment comprises or consists of a sequence selected from the group consisting of: SEQ ID NO:31 (SLP1), SEQ ID NO:32 (SLP2), SEQ ID NO:34 (SLP4) and SEQ ID NO:35 (SLP5), a pharmaceutically-acceptable carrier.

2. The immunogenic composition according to claim 1, wherein the composition further comprises an adjuvant.

3. The immunogenic composition according to claim 2, wherein the adjuvant is an immune potentiating adjuvant.

4. The immunogenic composition according to claim 1, wherein the peptide consists of the sequence set forth in SEQ ID NO:31 (SLP1).

5. The immunogenic composition according to claim 1, wherein the peptide consists of the sequence set forth in SEQ ID NO:32 (SLP2).

6. The immunogenic composition according to claim 1, wherein the peptide consists of the sequence set forth in SEQ ID NO:34 (SLP4).

7. The immunogenic composition according to claim 1, wherein the peptide consists of the sequence set forth in SEQ ID NO:35 (SLP5).

* * * * *

SEQUENCE LISTING

```
<160> NUMBER OF SEQ ID NOS: 123

<210> SEQ ID NO 1
<211> LENGTH: 9
<212> TYPE: PRT
<213> ORGANISM: Hepatitis B virus
<220> FEATURE:
<221> NAME/KEY: misc_feature
<223> OTHER INFORMATION: x70-78

<400> SEQUENCE: 1

Ala Leu Arg Phe Thr Ser Ala Arg Arg
1               5


<210> SEQ ID NO 2
<211> LENGTH: 9
<212> TYPE: PRT
<213> ORGANISM: Hepatitis B virus
<220> FEATURE:
<221> NAME/KEY: misc_feature
<223> OTHER INFORMATION: x67-75

<400> SEQUENCE: 2

Gly Pro Cys Ala Leu Arg Phe Thr Ser
1               5


<210> SEQ ID NO 3
<211> LENGTH: 12
<212> TYPE: PRT
<213> ORGANISM: Hepatitis B virus
<220> FEATURE:
<221> NAME/KEY: misc_feature
<223> OTHER INFORMATION: x62-73

<400> SEQUENCE: 3

Ala Phe Ser Ser Ala Gly Pro Cys Ala Leu Arg Phe
1               5                   10


<210> SEQ ID NO 4
<211> LENGTH: 9
<212> TYPE: PRT
<213> ORGANISM: Hepatitis B virus
<220> FEATURE:
<221> NAME/KEY: misc_feature
<223> OTHER INFORMATION: x58-66
```

<400> SEQUENCE: 4

Leu Pro Val Cys Ala Phe Ser Ser Ala
1 5

<210> SEQ ID NO 5
<211> LENGTH: 10
<212> TYPE: PRT
<213> ORGANISM: Hepatitis B virus
<220> FEATURE:
<221> NAME/KEY: misc_feature
<223> OTHER INFORMATION: x57-66

<400> SEQUENCE: 5

Gly Leu Pro Val Cys Ala Phe Ser Ser Ala
1 5 10

<210> SEQ ID NO 6
<211> LENGTH: 9
<212> TYPE: PRT
<213> ORGANISM: Hepatitis B virus
<220> FEATURE:
<221> NAME/KEY: misc_feature
<223> OTHER INFORMATION: x103-111

<400> SEQUENCE: 6

Met Ser Thr Thr Asp Leu Glu Ala Tyr
1 5

<210> SEQ ID NO 7
<211> LENGTH: 10
<212> TYPE: PRT
<213> ORGANISM: Hepatitis B virus
<220> FEATURE:
<221> NAME/KEY: misc_feature
<223> OTHER INFORMATION: x104-113

<400> SEQUENCE: 7

Ser Thr Thr Asp Leu Glu Ala Tyr Phe Lys
1 5 10

<210> SEQ ID NO 8
<211> LENGTH: 9
<212> TYPE: PRT
<213> ORGANISM: Hepatitis B virus
<220> FEATURE:
<221> NAME/KEY: misc_feature
<223> OTHER INFORMATION: x105-113

<400> SEQUENCE: 8

Thr Thr Asp Leu Glu Ala Tyr Phe Lys
1 5

<210> SEQ ID NO 9
<211> LENGTH: 11
<212> TYPE: PRT
<213> ORGANISM: Hepatitis B virus
<220> FEATURE:
<221> NAME/KEY: misc_feature
<223> OTHER INFORMATION: x110-120

<400> SEQUENCE: 9

Ala Tyr Phe Lys Asp Cys Val Phe Lys Asp Trp
1 5 10

<210> SEQ ID NO 10
<211> LENGTH: 9

<212> TYPE: PRT
<213> ORGANISM: Hepatitis B virus
<220> FEATURE:
<221> NAME/KEY: misc_feature
<223> OTHER INFORMATION: x132-140

<400> SEQUENCE: 10

Phe Val Leu Gly Gly Cys Arg His Lys
1 5

<210> SEQ ID NO 11
<211> LENGTH: 10
<212> TYPE: PRT
<213> ORGANISM: Hepatitis B virus
<220> FEATURE:
<221> NAME/KEY: misc_feature
<223> OTHER INFORMATION: p124-133

<400> SEQUENCE: 11

Pro Leu Asp Lys Gly Ile Lys Pro Tyr Tyr
1 5 10

<210> SEQ ID NO 12
<211> LENGTH: 10
<212> TYPE: PRT
<213> ORGANISM: Hepatitis B virus
<220> FEATURE:
<221> NAME/KEY: misc_feature
<223> OTHER INFORMATION: p164-173

<400> SEQUENCE: 12

Arg Ser Ala Ser Phe Cys Gly Ser Pro Tyr
1 5 10

<210> SEQ ID NO 13
<211> LENGTH: 9
<212> TYPE: PRT
<213> ORGANISM: Hepatitis B virus
<220> FEATURE:
<221> NAME/KEY: misc_feature
<223> OTHER INFORMATION: p275-283

<400> SEQUENCE: 13

Cys Leu His Gln Ser Ala Val Arg Lys
1 5

<210> SEQ ID NO 14
<211> LENGTH: 10
<212> TYPE: PRT
<213> ORGANISM: Hepatitis B virus
<220> FEATURE:
<221> NAME/KEY: misc_feature
<223> OTHER INFORMATION: p403-412

<400> SEQUENCE: 14

Ser Trp Pro Lys Phe Ala Val Pro Asn Leu
1 5 10

<210> SEQ ID NO 15
<211> LENGTH: 9
<212> TYPE: PRT
<213> ORGANISM: Hepatitis B virus
<220> FEATURE:
<221> NAME/KEY: misc_feature
<223> OTHER INFORMATION: p404-412

<400> SEQUENCE: 15

Trp Pro Lys Phe Ala Val Pro Asn Leu 1 5

<210> SEQ ID NO 16
<211> LENGTH: 9
<212> TYPE: PRT
<213> ORGANISM: Hepatitis B virus
<220> FEATURE:
<221> NAME/KEY: misc_feature
<223> OTHER INFORMATION: p407-415

<400> SEQUENCE: 16

Phe Ala Val Pro Asn Leu Gln Ser Leu
1 5

<210> SEQ ID NO 17
<211> LENGTH: 9
<212> TYPE: PRT
<213> ORGANISM: Hepatitis B virus
<220> FEATURE:
<221> NAME/KEY: misc_feature
<223> OTHER INFORMATION: p509-517

<400> SEQUENCE: 17

Ile Leu Gly Phe Arg Lys Ile Pro Met
1 5

<210> SEQ ID NO 18
<211> LENGTH: 9
<212> TYPE: PRT
<213> ORGANISM: Hepatitis B virus
<220> FEATURE:
<221> NAME/KEY: misc_feature
<223> OTHER INFORMATION: p515-523

<400> SEQUENCE: 18

Ile Pro Met Gly Val Gly Leu Ser Pro
1 5

<210> SEQ ID NO 19
<211> LENGTH: 10
<212> TYPE: PRT
<213> ORGANISM: Hepatitis B virus
<220> FEATURE:
<221> NAME/KEY: misc_feature
<223> OTHER INFORMATION: p649-658

<400> SEQUENCE: 19

Cys Gly Tyr Pro Ala Leu Met Pro Leu Tyr
1 5 10

<210> SEQ ID NO 20
<211> LENGTH: 9
<212> TYPE: PRT
<213> ORGANISM: Hepatitis B virus
<220> FEATURE:
<221> NAME/KEY: misc_feature
<223> OTHER INFORMATION: p650-658

<400> SEQUENCE: 20

Gly Tyr Pro Ala Leu Met Pro Leu Tyr
1 5

<210> SEQ ID NO 21
<211> LENGTH: 9
<212> TYPE: PRT
<213> ORGANISM: Hepatitis B virus
<220> FEATURE:
<221> NAME/KEY: misc_feature
<223> OTHER INFORMATION: p693-701

<400> SEQUENCE: 21

Gly Leu Cys Gln Val Phe Ala Asp Ala
1               5

<210> SEQ ID NO 22
<211> LENGTH: 10
<212> TYPE: PRT
<213> ORGANISM: Hepatitis B virus
<220> FEATURE:
<221> NAME/KEY: misc_feature
<223> OTHER INFORMATION: p697-706

<400> SEQUENCE: 22

Val Phe Ala Asp Ala Thr Pro Thr Gly Trp
1               5                   10

<210> SEQ ID NO 23
<211> LENGTH: 9
<212> TYPE: PRT
<213> ORGANISM: Hepatitis B virus
<220> FEATURE:
<221> NAME/KEY: misc_feature
<223> OTHER INFORMATION: p723-731

<400> SEQUENCE: 23

Leu Pro Ile His Thr Ala Glu Leu Leu
1               5

<210> SEQ ID NO 24
<211> LENGTH: 10
<212> TYPE: PRT
<213> ORGANISM: Hepatitis B virus
<220> FEATURE:
<221> NAME/KEY: misc_feature
<223> OTHER INFORMATION: p755-764

<400> SEQUENCE: 24

Arg Lys Tyr Thr Ser Phe Pro Trp Leu Leu
1               5                   10

<210> SEQ ID NO 25
<211> LENGTH: 10
<212> TYPE: PRT
<213> ORGANISM: Hepatitis B virus
<220> FEATURE:
<221> NAME/KEY: misc_feature
<223> OTHER INFORMATION: p756-765

<400> SEQUENCE: 25

Lys Tyr Thr Ser Phe Pro Trp Leu Leu Gly
1               5                   10

<210> SEQ ID NO 26
<211> LENGTH: 9
<212> TYPE: PRT
<213> ORGANISM: Hepatitis B virus
<220> FEATURE:
<221> NAME/KEY: misc_feature
<223> OTHER INFORMATION: p829-837

<400> SEQUENCE: 26

Arg Val His Phe Ala Ser Pro Leu His
1               5

<210> SEQ ID NO 27

```
<211> LENGTH: 832
<212> TYPE: PRT
<213> ORGANISM: Hepatitis B virus
<220> FEATURE:
<221> NAME/KEY: misc_feature
<223> OTHER INFORMATION: HBV polymerase sequence

<400> SEQUENCE: 27

Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Lys Val Thr Lys Tyr Leu Pro Leu Asp Lys Gly
        115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Asp Leu Gln His Gly Ala Glu Ser Phe His Gln Gln Ser Ser Gly
            180                 185                 190

Ile Leu Ser Arg Pro Pro Val Gly Ser Ser Leu Gln Ser Lys His Arg
        195                 200                 205

Lys Ser Arg Leu Gly Leu Gln Ser Gln Gln Gly His Leu Ala Arg Arg
    210                 215                 220

Gln Gln Gly Arg Ser Trp Ser Ile Arg Ala Gly Phe His Pro Thr Ala
225                 230                 235                 240

Arg Arg Pro Phe Gly Val Glu Pro Ser Gly Ser Gly His Thr Thr Asn
                245                 250                 255

Phe Ala Ser Lys Ser Ala Ser Cys Leu His Gln Ser Pro Val Arg Lys
            260                 265                 270

Ala Ala Tyr Pro Ala Val Ser Thr Phe Glu Lys His Ser Ser Ser Gly
        275                 280                 285

His Ala Val Glu Phe His Asn Leu Pro Pro Asn Ser Ala Arg Ser Gln
    290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser Leu Ile Val Asn Leu Leu Glu
                325                 330                 335

Asp Trp Gly Pro Cys Ala Glu His Gly Glu His His Ile Arg Ile Pro
            340                 345                 350

Arg Thr Pro Ser Arg Val Thr Gly Gly Val Phe Leu Val Asp Lys Asn
        355                 360                 365

Pro His Asn Thr Ala Glu Ser Arg Leu Val Val Asp Phe Ser Gln Phe
```

```
    370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
                405                 410                 415

Leu Asp Val Ser Ala Ala Phe Tyr His Leu Pro Leu His Pro Ala Ala
            420                 425                 430

Met Pro His Leu Leu Val Gly Ser Ser Gly Leu Ser Arg Tyr Val Ala
        435                 440                 445

Arg Leu Ser Ser Asn Ser Arg Ile Leu Asn Asn Gln His Gly Thr Met
    450                 455                 460

Pro Asp Leu His Asp Tyr Cys Ser Arg Asn Leu Tyr Val Ser Leu Leu
465                 470                 475                 480

Leu Leu Tyr Gln Thr Phe Gly Arg Lys Leu His Leu Tyr Ser His Pro
                485                 490                 495

Ile Ile Leu Gly Phe Arg Lys Ile Pro Met Gly Val Gly Leu Ser Pro
            500                 505                 510

Phe Leu Leu Ala Gln Phe Thr Ser Ala Ile Cys Ser Val Val Arg Arg
        515                 520                 525

Ala Phe Pro His Cys Leu Ala Phe Ser Tyr Met Asp Asp Val Val Leu
    530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
                565                 570                 575

Arg Trp Gly Tyr Ser Leu Asn Phe Met Gly Tyr Val Ile Gly Cys Tyr
            580                 585                 590

Gly Ser Leu Pro Gln Glu His Ile Ile Gln Lys Ile Lys Glu Cys Phe
        595                 600                 605

Arg Lys Leu Pro Ile Asn Arg Pro Ile Asp Trp Lys Val Cys Gln Arg
    610                 615                 620

Ile Val Gly Leu Leu Gly Phe Ala Ala Pro Phe Thr Gln Cys Gly Tyr
625                 630                 635                 640

Pro Ala Leu Met Pro Leu Tyr Ala Cys Ile Gln Ser Lys Gln Ala Phe
                645                 650                 655

Thr Phe Ser Pro Thr Tyr Lys Ala Phe Leu Cys Lys Gln Tyr Leu Asn
            660                 665                 670

Leu Tyr Pro Val Ala Arg Gln Arg Pro Gly Leu Cys Gln Val Phe Ala
        675                 680                 685

Asp Ala Thr Pro Thr Gly Trp Gly Leu Val Met Gly His Gln Arg Met
    690                 695                 700

Arg Gly Thr Phe Ser Ala Pro Leu Pro Ile His Thr Ala Glu Leu Leu
705                 710                 715                 720

Ala Ala Cys Phe Ala Arg Ser Arg Ser Gly Ala Asn Ile Ile Gly Thr
                725                 730                 735

Asp Asn Ser Val Val Leu Ser Arg Lys Tyr Thr Ser Phe Pro Trp Leu
            740                 745                 750

Leu Gly Cys Ala Ala Asn Trp Ile Leu Arg Gly Thr Ser Phe Val Tyr
        755                 760                 765

Val Pro Ser Ala Leu Asn Pro Ala Asp Asp Pro Ser Arg Gly Arg Leu
    770                 775                 780

Gly Leu Ser Arg Pro Leu Leu Arg Leu Pro Phe Arg Pro Thr Thr Gly
785                 790                 795                 800
```

```
Arg Thr Ser Leu Tyr Ala Asp Ser Pro Ser Val Pro Ser His Leu Pro
                805                 810                 815

Asp Arg Val His Phe Ala Ser Pro Leu His Val Ala Trp Arg Pro Pro
            820                 825                 830


<210> SEQ ID NO 28
<211> LENGTH: 843
<212> TYPE: PRT
<213> ORGANISM: Hepatitis B virus
<220> FEATURE:
<221> NAME/KEY: misc_feature
<223> OTHER INFORMATION: HBV polymerase consensus sequence

<400> SEQUENCE: 28

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

Asp Ile His Leu Gln Glu Asp Ile Ile Asn Arg Cys Gln Gln Phe Val
                85                  90                  95

Gly Pro Leu Thr Val Asn Glu Lys Arg Arg Leu Lys Leu Ile Met Pro
            100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu His Val Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Lys Arg His
            180                 185                 190

Gly Asp Glu Ser Phe Cys Ser Gln Ser Ser Gly Ile Leu Ser Arg Ser
        195                 200                 205

Pro Val Gly Pro Cys Ile Gln Ser Gln Leu Lys Gln Ser Arg Leu Gly
    210                 215                 220

Leu Gln Pro Gln Gln Gly Ser Leu Ala Arg Arg Gln Gln Gly Arg Ser
225                 230                 235                 240

Gly Ser Ile Arg Ala Arg Val His Pro Thr Thr Arg Arg Ser Phe Gly
                245                 250                 255

Val Glu Pro Ser Gly Ser Gly His Ile Asp Asn Ser Ala Ser Ser Ser
            260                 265                 270

Ser Ser Cys Leu His Gln Ser Ala Val Arg Lys Ala Ala Tyr Ser His
        275                 280                 285

Leu Ser Thr Ser Lys Arg Gln Ser Ser Ser Gly His Ala Val Glu Leu
    290                 295                 300

His Asn Ile Pro Pro Ser Ser Ala Arg Ser Gln Ser Glu Gly Pro Val
305                 310                 315                 320

Phe Ser Cys Trp Trp Leu Gln Phe Arg Asn Ser Lys Pro Cys Ser Asp
```

-continued

```
                325                 330                 335

Tyr Cys Leu Ser His Ile Val Asn Leu Leu Glu Asp Trp Gly Pro Cys
            340                 345                 350

Thr Glu His Gly Glu His His Ile Arg Ile Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Leu Pro Leu His Pro Ala Ala Met Pro His Leu Leu
        435                 440                 445

Val Gly Ser Ser Gly Leu Ser Arg Tyr Val Ala Arg Leu Ser Ser Asn
    450                 455                 460

Ser Arg Ile Ile Asn Asn Gln His Gly Thr Met Gln Asn Leu His Asp
465                 470                 475                 480

Ser Cys Ser Arg Asn Leu Tyr Val Ser Leu Leu Leu Leu Tyr Lys Thr
                485                 490                 495

Phe Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
        515                 520                 525

Phe Thr Ser Ala Ile Cys Ser Val Val Arg Arg Ala Phe Pro His Cys
    530                 535                 540

Leu Ala Phe Ser Tyr Met Asp Asp Val Val Leu Gly Ala Lys Ser Val
545                 550                 555                 560

Gln His Leu Glu Ser Leu Tyr Thr Ala Val Thr Asn Phe Leu Leu Ser
                565                 570                 575

Leu Gly Ile His Leu Asn Pro Asn Lys Thr Lys Arg Trp Gly Tyr Ser
            580                 585                 590

Leu Asn Phe Met Gly Tyr Val Ile Gly Ser Trp Gly Thr Leu Pro Gln
        595                 600                 605

Glu His Ile Val Gln Lys Ile Lys Gln Cys Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ala Lys Gln Ala Phe Thr Phe Ser Pro Thr
            660                 665                 670

Tyr Lys Ala Phe Leu Cys Lys Gln Tyr Leu Asn Leu Tyr Pro Val Ala
        675                 680                 685

Arg Gln Arg Pro Gly Leu Cys Gln Val Phe Ala Asp Ala Thr Pro Thr
    690                 695                 700

Gly Trp Gly Leu Ala Ile Gly His Gln Arg Met Arg Gly Thr Phe Val
705                 710                 715                 720

Ala Pro Leu Pro Ile His Thr Ala Glu Leu Leu Ala Ala Cys Phe Ala
                725                 730                 735

Arg Ser Arg Ser Gly Ala Lys Leu Ile Gly Thr Asp Asn Ser Val Val
            740                 745                 750
```

```
Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
    770                 775                 780

Asn Pro Ala Asp Asp Pro Ser Arg Gly Arg Leu Gly Leu Tyr Arg Pro
785                 790                 795                 800

Leu Leu Arg Leu Pro Phe Arg Pro Thr Thr Gly Arg Thr Ser Leu Tyr
                805                 810                 815

Ala Val Ser Pro Ser Val Pro Ser His Leu Pro Asp Arg Val His Phe
            820                 825                 830

Ala Ser Pro Leu His Val Ala Trp Arg Pro Pro
        835                 840


<210> SEQ ID NO 29
<211> LENGTH: 154
<212> TYPE: PRT
<213> ORGANISM: Hepatitis B virus
<220> FEATURE:
<221> NAME/KEY: misc_feature
<223> OTHER INFORMATION: HBV-X sequene

<400> SEQUENCE: 29

Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Phe Ser Gly
            20                  25                  30

Ser Leu Gly Thr Leu Ser Ser Pro Ser Pro Ser Ala Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
        115                 120                 125

Leu Lys Val Phe Val Leu Gly Gly Cys Arg His Lys Leu Val Cys Ala
    130                 135                 140

Pro Ala Pro Cys Asn Phe Phe Thr Ser Ala
145                 150


<210> SEQ ID NO 30
<211> LENGTH: 154
<212> TYPE: PRT
<213> ORGANISM: Hepatitis B virus
<220> FEATURE:
<221> NAME/KEY: misc_feature
<223> OTHER INFORMATION: HBV-X consensus sequence

<400> SEQUENCE: 30

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Ser Gly
            20                  25                  30

Pro Leu Gly Thr Leu Pro Ser Pro Ser Pro Ser Ala Val Pro Ala Asp
        35                  40                  45
```

-continued

His Gly Ala His Leu Ser Leu Arg Gly Leu Pro Val Cys Ala Phe Ser
50 55 60

Ser Ala Gly Pro Cys Ala Leu Arg Phe Thr Ser Ala Arg Arg Met Glu
65 70 75 80

Thr Thr Val Asn Ala His Gln Val Leu Pro Lys Val Leu His Lys Arg
85 90 95

Thr Leu Gly Leu Ser Ala Met Ser Thr Thr Asp Leu Glu Ala Tyr Phe
100 105 110

Lys Asp Cys Val Phe Lys Asp Trp Glu Glu Leu Gly Glu Glu Ile Arg
115 120 125

Leu Lys Val Phe Val Leu Gly Gly Cys Arg His Lys Leu Val Cys Ser
130 135 140

Pro Ala Pro Cys Asn Phe Phe Thr Ser Ala
145 150

<210> SEQ ID NO 31
<211> LENGTH: 25
<212> TYPE: PRT
<213> ORGANISM: Hepatitis B virus
<220> FEATURE:
<221> NAME/KEY: misc_feature
<223> OTHER INFORMATION: SLP1

<400> SEQUENCE: 31

His Leu Ser Leu Arg Gly Leu Pro Val Cys Ala Phe Ser Ser Ala Gly
1 5 10 15

Pro Cys Ala Leu Arg Phe Thr Ser Ala
20 25

<210> SEQ ID NO 32
<211> LENGTH: 25
<212> TYPE: PRT
<213> ORGANISM: Hepatitis B virus
<220> FEATURE:
<221> NAME/KEY: misc_feature
<223> OTHER INFORMATION: SLP2

<400> SEQUENCE: 32

Leu Ser Ala Met Ser Thr Thr Asp Leu Glu Ala Tyr Phe Lys Asp Cys
1 5 10 15

Leu Phe Lys Asp Trp Glu Glu Leu Gly
20 25

<210> SEQ ID NO 33
<211> LENGTH: 25
<212> TYPE: PRT
<213> ORGANISM: Hepatitis B virus
<220> FEATURE:
<221> NAME/KEY: misc_feature
<223> OTHER INFORMATION: SLP3

<400> SEQUENCE: 33

Ala Ser Ser Ser Ser Ser Cys Leu His Gln Ser Ala Val Arg Lys Ala
1 5 10 15

Ala Tyr Ser His Leu Ser Thr Ser Lys
20 25

<210> SEQ ID NO 34
<211> LENGTH: 25
<212> TYPE: PRT
<213> ORGANISM: Hepatitis B virus
<220> FEATURE:

<221> NAME/KEY: misc_feature
<223> OTHER INFORMATION: SLP4

<400> SEQUENCE: 34

Arg Lys Leu His Leu Tyr Ser His Pro Ile Ile Leu Gly Phe Arg Lys
1 5 10 15

Ile Pro Met Gly Val Gly Leu Ser Pro
20 25

<210> SEQ ID NO 35
<211> LENGTH: 26
<212> TYPE: PRT
<213> ORGANISM: Hepatitis B virus
<220> FEATURE:
<221> NAME/KEY: misc_feature
<223> OTHER INFORMATION: SLP5

<400> SEQUENCE: 35

Gly Phe Ala Ala Pro Phe Thr Gln Cys Gly Tyr Pro Ala Leu Met Pro
1 5 10 15

Leu Tyr Ala Cys Ile Gln Ala Lys Gln Ala
20 25

<210> SEQ ID NO 36
<211> LENGTH: 25
<212> TYPE: PRT
<213> ORGANISM: Hepatitis B virus
<220> FEATURE:
<221> NAME/KEY: misc_feature
<223> OTHER INFORMATION: SLP6

<400> SEQUENCE: 36

Ala Arg Gln Arg Pro Gly Leu Cys Gln Val Phe Ala Asp Ala Thr Pro
1 5 10 15

Thr Gly Trp Gly Leu Ala Ile Gly His
20 25

<210> SEQ ID NO 37
<211> LENGTH: 25
<212> TYPE: PRT
<213> ORGANISM: Hepatitis B virus
<220> FEATURE:
<221> NAME/KEY: misc_feature
<223> OTHER INFORMATION: SLP7

<400> SEQUENCE: 37

Ser Pro Ser Val Pro Ser His Leu Pro Asp Arg Val His Phe Ala Ser
1 5 10 15

Pro Leu His Val Ala Trp Arg Pro Pro
20 25

<210> SEQ ID NO 38
<211> LENGTH: 34
<212> TYPE: PRT
<213> ORGANISM: Hepatitis B virus

<400> SEQUENCE: 38

Val Val Asn Glu Lys Arg Arg Leu Lys Leu Ile Met Pro Ala Arg Phe
1 5 10 15

Tyr Pro Thr His Thr Lys Tyr Leu Pro Leu Asp Lys Gly Ile Lys Pro
20 25 30

Tyr Tyr

<210> SEQ ID NO 39
<211> LENGTH: 33
<212> TYPE: PRT
<213> ORGANISM: Hepatitis B virus

<400> SEQUENCE: 39

```
Tyr Pro Thr His Thr Lys Tyr Leu Pro Leu Asp Lys Gly Ile Lys Pro
1               5                   10                  15

Tyr Tyr Pro Asp Gln Val Val Asn His Tyr Phe Gln Thr Arg His Tyr
            20                  25                  30

Leu
```

<210> SEQ ID NO 40
<211> LENGTH: 33
<212> TYPE: PRT
<213> ORGANISM: Hepatitis B virus

<400> SEQUENCE: 40

```
Thr Ala Glu Ser Arg Leu Val Val Asp Phe Ser Gln Phe Ser Arg Gly
1               5                   10                  15

Ile Ser Arg Val Ser Trp Pro Lys Phe Ala Val Pro Asn Leu Gln Ser
            20                  25                  30

Leu
```

<210> SEQ ID NO 41
<211> LENGTH: 32
<212> TYPE: PRT
<213> ORGANISM: Hepatitis B virus

<400> SEQUENCE: 41

```
Gln Arg Met Arg Gly Thr Phe Val Ala Pro Leu Pro Ile His Thr Ala
1               5                   10                  15

Glu Leu Leu Ala Ala Cys Phe Ala Arg Ser Arg Ser Gly Ala Lys Leu
            20                  25                  30
```

<210> SEQ ID NO 42
<211> LENGTH: 33
<212> TYPE: PRT
<213> ORGANISM: Hepatitis B virus

<400> SEQUENCE: 42

```
Ala Leu Pro Ser Pro Ser Pro Ser Ala Val Pro Ala Asp His Gly Ala
1               5                   10                  15

His Leu Ser Leu Arg Gly Leu Pro Val Cys Ala Phe Ser Ser Ala Gly
            20                  25                  30

Pro
```

<210> SEQ ID NO 43
<211> LENGTH: 34
<212> TYPE: PRT
<213> ORGANISM: Hepatitis B virus

<400> SEQUENCE: 43

```
Leu Glu Ala Tyr Phe Lys Asp Cys Val Phe Lys Asp Trp Glu Glu Leu
1               5                   10                  15

Gly Glu Glu Ile Arg Leu Lys Val Phe Val Leu Gly Gly Cys Arg His
            20                  25                  30

Lys Leu
```

<210> SEQ ID NO 44

<211> LENGTH: 8
<212> TYPE: PRT
<213> ORGANISM: Hepatitis B virus
<220> FEATURE:
<221> NAME/KEY: misc_feature
<223> OTHER INFORMATION: p166-173

<400> SEQUENCE: 44

Ala Ser Phe Cys Gly Ser Pro Tyr
1               5

<210> SEQ ID NO 45
<211> LENGTH: 9
<212> TYPE: PRT
<213> ORGANISM: Hepatitis B virus
<220> FEATURE:
<221> NAME/KEY: misc_feature
<223> OTHER INFORMATION: p549-557

<400> SEQUENCE: 45

Tyr Met Asp Asp Val Val Leu Gly Ala
1               5

<210> SEQ ID NO 46
<211> LENGTH: 9
<212> TYPE: PRT
<213> ORGANISM: Hepatitis B virus
<220> FEATURE:
<221> NAME/KEY: misc_feature
<223> OTHER INFORMATION: x63-71

<400> SEQUENCE: 46

Phe Ser Ser Ala Gly Pro Cys Ala Leu
1               5

<210> SEQ ID NO 47
<211> LENGTH: 10
<212> TYPE: PRT
<213> ORGANISM: Hepatitis B virus
<220> FEATURE:
<221> NAME/KEY: misc_feature
<223> OTHER INFORMATION: x102-111

<400> SEQUENCE: 47

Ala Met Ser Thr Thr Asp Leu Glu Ala Tyr
1               5                   10

<210> SEQ ID NO 48
<211> LENGTH: 10
<212> TYPE: PRT
<213> ORGANISM: Hepatitis B virus
<220> FEATURE:
<221> NAME/KEY: misc_feature
<223> OTHER INFORMATION: p642-651

<400> SEQUENCE: 48

Phe Ala Ala Pro Phe Thr Gln Cys Gly Tyr
1               5                   10

<210> SEQ ID NO 49
<211> LENGTH: 10
<212> TYPE: PRT
<213> ORGANISM: Hepatitis B virus
<220> FEATURE:
<221> NAME/KEY: misc_feature
<223> OTHER INFORMATION: p149-158

<400> SEQUENCE: 49

```
His Thr Leu Trp Lys Ala Gly Ile Leu Tyr
1               5                   10


<210> SEQ ID NO 50
<211> LENGTH: 9
<212> TYPE: PRT
<213> ORGANISM: Hepatitis B virus
<220> FEATURE:
<221> NAME/KEY: misc_feature
<223> OTHER INFORMATION: x104-112

<400> SEQUENCE: 50

Ser Thr Thr Asp Leu Glu Ala Tyr Phe
1               5


<210> SEQ ID NO 51
<211> LENGTH: 10
<212> TYPE: PRT
<213> ORGANISM: Hepatitis B virus
<220> FEATURE:
<221> NAME/KEY: misc_feature
<223> OTHER INFORMATION: x103-112

<400> SEQUENCE: 51

Met Ser Thr Thr Asp Leu Glu Ala Tyr Phe
1               5                   10


<210> SEQ ID NO 52
<211> LENGTH: 11
<212> TYPE: PRT
<213> ORGANISM: Hepatitis B virus
<220> FEATURE:
<221> NAME/KEY: misc_feature
<223> OTHER INFORMATION: x63-73

<400> SEQUENCE: 52

Phe Ser Ser Ala Gly Pro Cys Ala Leu Arg Phe
1               5                   10


<210> SEQ ID NO 53
<211> LENGTH: 10
<212> TYPE: PRT
<213> ORGANISM: Hepatitis B virus
<220> FEATURE:
<221> NAME/KEY: misc_feature
<223> OTHER INFORMATION: p646-655

<400> SEQUENCE: 53

Phe Thr Gln Cys Gly Tyr Pro Ala Leu Met
1               5                   10


<210> SEQ ID NO 54
<211> LENGTH: 9
<212> TYPE: PRT
<213> ORGANISM: Hepatitis B virus
<220> FEATURE:
<221> NAME/KEY: misc_feature
<223> OTHER INFORMATION: p165-173

<400> SEQUENCE: 54

Ser Ala Ser Phe Cys Gly Ser Pro Tyr
1               5


<210> SEQ ID NO 55
<211> LENGTH: 9
<212> TYPE: PRT
<213> ORGANISM: Hepatitis B virus
<220> FEATURE:
```

<221> NAME/KEY: misc_feature
<223> OTHER INFORMATION: p55-63

<400> SEQUENCE: 55

Lys Val Gly Asn Phe Thr Gly Leu Tyr
1 5

<210> SEQ ID NO 56
<211> LENGTH: 10
<212> TYPE: PRT
<213> ORGANISM: Hepatitis B virus
<220> FEATURE:
<221> NAME/KEY: misc_feature
<223> OTHER INFORMATION: p54-63

<400> SEQUENCE: 56

His Lys Val Gly Asn Phe Thr Gly Leu Tyr
1 5 10

<210> SEQ ID NO 57
<211> LENGTH: 10
<212> TYPE: PRT
<213> ORGANISM: Hepatitis B virus
<220> FEATURE:
<221> NAME/KEY: misc_feature
<223> OTHER INFORMATION: c18-27

<400> SEQUENCE: 57

Phe Leu Pro Ser Asp Phe Phe Pro Ser Val
1 5 10

<210> SEQ ID NO 58
<211> LENGTH: 9
<212> TYPE: PRT
<213> ORGANISM: Hepatitis B virus
<220> FEATURE:
<221> NAME/KEY: misc_feature
<223> OTHER INFORMATION: p368-376

<400> SEQUENCE: 58

Arg Val Thr Gly Gly Val Phe Leu Val
1 5

<210> SEQ ID NO 59
<211> LENGTH: 9
<212> TYPE: PRT
<213> ORGANISM: Hepatitis B virus
<220> FEATURE:
<221> NAME/KEY: misc_feature
<223> OTHER INFORMATION: x15-23

<400> SEQUENCE: 59

Val Leu Cys Leu Arg Pro Val Gly Ala
1 5

<210> SEQ ID NO 60
<211> LENGTH: 9
<212> TYPE: PRT
<213> ORGANISM: Hepatitis B virus
<220> FEATURE:
<221> NAME/KEY: misc_feature
<223> OTHER INFORMATION: p730-738

<400> SEQUENCE: 60

Leu Leu Ala Ala Cys Phe Ala Arg Ser
1 5

<210> SEQ ID NO 61
<211> LENGTH: 9
<212> TYPE: PRT
<213> ORGANISM: Hepatitis B virus
<220> FEATURE:
<221> NAME/KEY: misc_feature
<223> OTHER INFORMATION: p411-419

<400> SEQUENCE: 61

Asn Leu Gln Ser Leu Thr Asn Leu Leu
1               5

<210> SEQ ID NO 62
<211> LENGTH: 9
<212> TYPE: PRT
<213> ORGANISM: Hepatitis B virus
<220> FEATURE:
<221> NAME/KEY: misc_feature
<223> OTHER INFORMATION: x102-110

<400> SEQUENCE: 62

Ala Met Ser Thr Thr Asp Leu Glu Ala
1               5

<210> SEQ ID NO 63
<211> LENGTH: 10
<212> TYPE: PRT
<213> ORGANISM: Hepatitis B virus
<220> FEATURE:
<221> NAME/KEY: misc_feature
<223> OTHER INFORMATION: x91-100

<400> SEQUENCE: 63

Lys Val Leu His Lys Arg Thr Leu Gly Leu
1               5                   10

<210> SEQ ID NO 64
<211> LENGTH: 9
<212> TYPE: PRT
<213> ORGANISM: Hepatitis B virus
<220> FEATURE:
<221> NAME/KEY: misc_feature
<223> OTHER INFORMATION: p646-654

<400> SEQUENCE: 64

Phe Thr Gln Cys Gly Tyr Pro Ala Leu
1               5

<210> SEQ ID NO 65
<211> LENGTH: 10
<212> TYPE: PRT
<213> ORGANISM: Hepatitis B virus
<220> FEATURE:
<221> NAME/KEY: misc_feature
<223> OTHER INFORMATION: x132-141

<400> SEQUENCE: 65

Phe Val Leu Gly Gly Cys Arg His Lys Leu
1               5                   10

<210> SEQ ID NO 66
<211> LENGTH: 10
<212> TYPE: PRT
<213> ORGANISM: Hepatitis B virus
<220> FEATURE:
<221> NAME/KEY: misc_feature
<223> OTHER INFORMATION: x51-60

<400> SEQUENCE: 66

Ala His Leu Ser Leu Arg Gly Leu Pro Val
1 5 10

<210> SEQ ID NO 67
<211> LENGTH: 10
<212> TYPE: PRT
<213> ORGANISM: Hepatitis B virus
<220> FEATURE:
<221> NAME/KEY: misc_feature
<223> OTHER INFORMATION: x133-142

<400> SEQUENCE: 67

Val Leu Gly Gly Cys Arg His Lys Leu Val
1 5 10

<210> SEQ ID NO 68
<211> LENGTH: 9
<212> TYPE: PRT
<213> ORGANISM: Hepatitis B virus
<220> FEATURE:
<221> NAME/KEY: misc_feature
<223> OTHER INFORMATION: p59-67

<400> SEQUENCE: 68

Phe Thr Gly Leu Tyr Ser Ser Thr Val
1 5

<210> SEQ ID NO 69
<211> LENGTH: 9
<212> TYPE: PRT
<213> ORGANISM: Hepatitis B virus
<220> FEATURE:
<221> NAME/KEY: misc_feature
<223> OTHER INFORMATION: p547-555

<400> SEQUENCE: 69

Phe Ser Tyr Met Asp Asp Val Val Leu
1 5

<210> SEQ ID NO 70
<211> LENGTH: 10
<212> TYPE: PRT
<213> ORGANISM: Hepatitis B virus
<220> FEATURE:
<221> NAME/KEY: misc_feature
<223> OTHER INFORMATION: x97-106

<400> SEQUENCE: 70

Thr Leu Gly Leu Ser Ala Met Ser Thr Thr
1 5 10

<210> SEQ ID NO 71
<211> LENGTH: 9
<212> TYPE: PRT
<213> ORGANISM: Hepatitis B virus
<220> FEATURE:
<221> NAME/KEY: misc_feature
<223> OTHER INFORMATION: p545-553

<400> SEQUENCE: 71

Leu Ala Phe Ser Tyr Met Asp Asp Val
1 5

<210> SEQ ID NO 72
<211> LENGTH: 10
<212> TYPE: PRT
<213> ORGANISM: Hepatitis B virus
<220> FEATURE:
<221> NAME/KEY: misc_feature
<223> OTHER INFORMATION: p665-674

<400> SEQUENCE: 72

Gln Ala Phe Thr Phe Ser Pro Thr Tyr Lys
1 5 10

<210> SEQ ID NO 73
<211> LENGTH: 10
<212> TYPE: PRT
<213> ORGANISM: Hepatitis B virus
<220> FEATURE:
<221> NAME/KEY: misc_feature
<223> OTHER INFORMATION: p150-159

<400> SEQUENCE: 73

Thr Leu Trp Lys Ala Gly Ile Leu Tyr Lys
1 5 10

<210> SEQ ID NO 74
<211> LENGTH: 10
<212> TYPE: PRT
<213> ORGANISM: Hepatitis B virus
<220> FEATURE:
<221> NAME/KEY: misc_feature
<223> OTHER INFORMATION: p549-558

<400> SEQUENCE: 74

Tyr Met Asp Asp Val Val Leu Gly Ala Lys
1 5 10

<210> SEQ ID NO 75
<211> LENGTH: 9
<212> TYPE: PRT
<213> ORGANISM: Hepatitis B virus
<220> FEATURE:
<221> NAME/KEY: misc_feature
<223> OTHER INFORMATION: p106-114

<400> SEQUENCE: 75

Arg Leu Lys Leu Ile Met Pro Ala Arg
1 5

<210> SEQ ID NO 76
<211> LENGTH: 10
<212> TYPE: PRT
<213> ORGANISM: Hepatitis B virus
<220> FEATURE:
<221> NAME/KEY: misc_feature
<223> OTHER INFORMATION: p369-378

<400> SEQUENCE: 76

Val Thr Gly Gly Val Phe Leu Val Asp Lys
1 5 10

<210> SEQ ID NO 77
<211> LENGTH: 10
<212> TYPE: PRT
<213> ORGANISM: Hepatitis B virus
<220> FEATURE:
<221> NAME/KEY: misc_feature
<223> OTHER INFORMATION: x69-78

<400> SEQUENCE: 77

Cys Ala Leu Arg Phe Thr Ser Ala Arg Arg
1 5 10

<210> SEQ ID NO 78
<211> LENGTH: 10
<212> TYPE: PRT
<213> ORGANISM: Hepatitis B virus
<220> FEATURE:
<221> NAME/KEY: misc_feature
<223> OTHER INFORMATION: p730-739

<400> SEQUENCE: 78

Leu Leu Ala Ala Cys Phe Ala Arg Ser Arg
1 5 10

<210> SEQ ID NO 79
<211> LENGTH: 9
<212> TYPE: PRT
<213> ORGANISM: Hepatitis B virus
<220> FEATURE:
<221> NAME/KEY: misc_feature
<223> OTHER INFORMATION: p108-116

<400> SEQUENCE: 79

Lys Leu Ile Met Pro Ala Arg Phe Tyr
1 5

<210> SEQ ID NO 80
<211> LENGTH: 10
<212> TYPE: PRT
<213> ORGANISM: Hepatitis B virus
<220> FEATURE:
<221> NAME/KEY: misc_feature
<223> OTHER INFORMATION: p107-116

<400> SEQUENCE: 80

Leu Lys Leu Ile Met Pro Ala Arg Phe Tyr
1 5 10

<210> SEQ ID NO 81
<211> LENGTH: 9
<212> TYPE: PRT
<213> ORGANISM: Hepatitis B virus
<220> FEATURE:
<221> NAME/KEY: misc_feature
<223> OTHER INFORMATION: p771-779

<400> SEQUENCE: 81

Ile Leu Arg Gly Thr Ser Phe Val Tyr
1 5

<210> SEQ ID NO 82
<211> LENGTH: 9
<212> TYPE: PRT
<213> ORGANISM: Hepatitis B virus
<220> FEATURE:
<221> NAME/KEY: misc_feature
<223> OTHER INFORMATION: p756-764

<400> SEQUENCE: 82

Lys Tyr Thr Ser Phe Pro Trp Leu Leu
1 5

<210> SEQ ID NO 83
<211> LENGTH: 9
<212> TYPE: PRT
<213> ORGANISM: Hepatitis B virus
<220> FEATURE:
<221> NAME/KEY: misc_feature
<223> OTHER INFORMATION: p403-412

<400> SEQUENCE: 83

Ser Phe Cys Gly Ser Pro Tyr Ser Trp
1 5

<210> SEQ ID NO 84
<211> LENGTH: 10
<212> TYPE: PRT
<213> ORGANISM: Hepatitis B virus
<220> FEATURE:
<221> NAME/KEY: misc_feature
<223> OTHER INFORMATION: p166-175

<400> SEQUENCE: 84

Ala Ser Phe Cys Gly Ser Pro Tyr Ser Trp
1 5 10

<210> SEQ ID NO 85
<211> LENGTH: 10
<212> TYPE: PRT
<213> ORGANISM: Hepatitis B virus
<220> FEATURE:
<221> NAME/KEY: misc_feature
<223> OTHER INFORMATION: x111-120

<400> SEQUENCE: 85

Tyr Phe Lys Asp Cys Val Phe Lys Asp Trp
1 5 10

<210> SEQ ID NO 86
<211> LENGTH: 9
<212> TYPE: PRT
<213> ORGANISM: Hepatitis B virus
<220> FEATURE:
<221> NAME/KEY: misc_feature
<223> OTHER INFORMATION: p752-760

<400> SEQUENCE: 86

Val Leu Ser Arg Lys Tyr Thr Ser Phe
1 5

<210> SEQ ID NO 87
<211> LENGTH: 8
<212> TYPE: PRT
<213> ORGANISM: Hepatitis B virus
<220> FEATURE:
<221> NAME/KEY: misc_feature
<223> OTHER INFORMATION: x110-117

<400> SEQUENCE: 87

Ala Tyr Phe Lys Asp Cys Val Phe
1 5

<210> SEQ ID NO 88
<211> LENGTH: 10
<212> TYPE: PRT
<213> ORGANISM: Hepatitis B virus
<220> FEATURE:
<221> NAME/KEY: misc_feature
<223> OTHER INFORMATION: p406-415

<400> SEQUENCE: 88

Lys Phe Ala Val Pro Asn Leu Gln Ser Leu
1 5 10

<210> SEQ ID NO 89
<211> LENGTH: 9
<212> TYPE: PRT

<213> ORGANISM: Hepatitis B virus
<220> FEATURE:
<221> NAME/KEY: misc_feature
<223> OTHER INFORMATION: p146-154

<400> SEQUENCE: 89

His Tyr Leu His Thr Leu Trp Lys Ala
1               5

<210> SEQ ID NO 90
<211> LENGTH: 9
<212> TYPE: PRT
<213> ORGANISM: Hepatitis B virus
<220> FEATURE:
<221> NAME/KEY: misc_feature
<223> OTHER INFORMATION: p548-556

<400> SEQUENCE: 90

Ser Tyr Met Asp Asp Val Val Leu Gly
1               5

<210> SEQ ID NO 91
<211> LENGTH: 9
<212> TYPE: PRT
<213> ORGANISM: Hepatitis B virus
<220> FEATURE:
<221> NAME/KEY: misc_feature
<223> OTHER INFORMATION: p387-395

<400> SEQUENCE: 91

Arg Leu Val Val Asp Phe Ser Gln Phe
1               5

<210> SEQ ID NO 92
<211> LENGTH: 9
<212> TYPE: PRT
<213> ORGANISM: Hepatitis B virus
<220> FEATURE:
<221> NAME/KEY: misc_feature
<223> OTHER INFORMATION: x143-151

<400> SEQUENCE: 92

Cys Ser Pro Ala Pro Cys Asn Phe Phe
1               5

<210> SEQ ID NO 93
<211> LENGTH: 10
<212> TYPE: PRT
<213> ORGANISM: Hepatitis B virus
<220> FEATURE:
<221> NAME/KEY: misc_feature
<223> OTHER INFORMATION: p365-374

<400> SEQUENCE: 93

Thr Pro Ala Arg Val Thr Gly Gly Val Phe
1               5                   10

<210> SEQ ID NO 94
<211> LENGTH: 9
<212> TYPE: PRT
<213> ORGANISM: Hepatitis B virus
<220> FEATURE:
<221> NAME/KEY: misc_feature
<223> OTHER INFORMATION: p651-659

<400> SEQUENCE: 94

Tyr Pro Ala Leu Met Pro Leu Tyr Ala
1               5

<210> SEQ ID NO 95
<211> LENGTH: 9
<212> TYPE: PRT
<213> ORGANISM: Hepatitis B virus
<220> FEATURE:
<221> NAME/KEY: misc_feature
<223> OTHER INFORMATION: p365-373

<400> SEQUENCE: 95

Thr Pro Ala Arg Val Thr Gly Gly Val
1               5

<210> SEQ ID NO 96
<211> LENGTH: 9
<212> TYPE: PRT
<213> ORGANISM: Hepatitis B virus
<220> FEATURE:
<221> NAME/KEY: misc_feature
<223> OTHER INFORMATION: x52-60

<400> SEQUENCE: 96

His Leu Ser Leu Arg Gly Leu Pro Val
1               5

<210> SEQ ID NO 97
<211> LENGTH: 9
<212> TYPE: PRT
<213> ORGANISM: Hepatitis B virus
<220> FEATURE:
<221> NAME/KEY: misc_feature
<223> OTHER INFORMATION: x92-100

<400> SEQUENCE: 97

Val Leu His Lys Arg Thr Leu Gly Leu
1               5

<210> SEQ ID NO 98
<211> LENGTH: 9
<212> TYPE: PRT
<213> ORGANISM: Hepatitis B virus
<220> FEATURE:
<221> NAME/KEY: misc_feature
<223> OTHER INFORMATION: x94-102

<400> SEQUENCE: 98

His Lys Arg Thr Leu Gly Leu Ser Ala
1               5

<210> SEQ ID NO 99
<211> LENGTH: 9
<212> TYPE: PRT
<213> ORGANISM: Hepatitis B virus
<220> FEATURE:
<221> NAME/KEY: misc_feature
<223> OTHER INFORMATION: x95-103

<400> SEQUENCE: 99

Lys Arg Thr Leu Gly Leu Ser Ala Met
1               5

<210> SEQ ID NO 100
<211> LENGTH: 9
<212> TYPE: PRT
<213> ORGANISM: Hepatitis B virus
<220> FEATURE:
<221> NAME/KEY: misc_feature
<223> OTHER INFORMATION: x89-97

<400> SEQUENCE: 100

Leu Pro Lys Val Leu His Lys Arg Thr
1 5

<210> SEQ ID NO 101
<211> LENGTH: 9
<212> TYPE: PRT
<213> ORGANISM: Hepatitis B virus
<220> FEATURE:
<221> NAME/KEY: misc_feature
<223> OTHER INFORMATION: p712-720

<400> SEQUENCE: 101

His Gln Arg Met Arg Gly Thr Phe Val
1 5

<210> SEQ ID NO 102
<211> LENGTH: 9
<212> TYPE: PRT
<213> ORGANISM: Hepatitis B virus
<220> FEATURE:
<221> NAME/KEY: misc_feature
<223> OTHER INFORMATION: x50-58

<400> SEQUENCE: 102

Gly Ala His Leu Ser Leu Arg Gly Leu
1 5

<210> SEQ ID NO 103
<211> LENGTH: 8
<212> TYPE: PRT
<213> ORGANISM: Hepatitis B virus
<220> FEATURE:
<221> NAME/KEY: misc_feature
<223> OTHER INFORMATION: c123-130

<400> SEQUENCE: 103

Gly Leu Lys Ile Leu Gln Leu Leu
1 5

<210> SEQ ID NO 104
<211> LENGTH: 9
<212> TYPE: PRT
<213> ORGANISM: Hepatitis B virus
<220> FEATURE:
<221> NAME/KEY: misc_feature
<223> OTHER INFORMATION: p500-508

<400> SEQUENCE: 104

Lys Leu His Leu Tyr Ser His Pro Ile
1 5

<210> SEQ ID NO 105
<211> LENGTH: 9
<212> TYPE: PRT
<213> ORGANISM: Hepatitis B virus
<220> FEATURE:
<221> NAME/KEY: misc_feature
<223> OTHER INFORMATION: p502-510

<400> SEQUENCE: 105

His Leu Tyr Ser His Pro Ile Ile Leu
1 5

<210> SEQ ID NO 106
<211> LENGTH: 10

<212> TYPE: PRT
<213> ORGANISM: Hepatitis B virus
<220> FEATURE:
<221> NAME/KEY: misc_feature
<223> OTHER INFORMATION: x89-98

<400> SEQUENCE: 106

Leu Pro Lys Val Leu His Lys Arg Thr Leu
1 5 10

<210> SEQ ID NO 107
<211> LENGTH: 10
<212> TYPE: PRT
<213> ORGANISM: Hepatitis B virus
<220> FEATURE:
<221> NAME/KEY: misc_feature
<223> OTHER INFORMATION: p751-760

<400> SEQUENCE: 107

Val Val Leu Ser Arg Lys Tyr Thr Ser Phe
1 5 10

<210> SEQ ID NO 108
<211> LENGTH: 10
<212> TYPE: PRT
<213> ORGANISM: Hepatitis B virus
<220> FEATURE:
<221> NAME/KEY: misc_feature
<223> OTHER INFORMATION: x54-63

<400> SEQUENCE: 108

Ser Leu Arg Gly Leu Pro Val Cys Ala Phe
1 5 10

<210> SEQ ID NO 109
<211> LENGTH: 10
<212> TYPE: PRT
<213> ORGANISM: Hepatitis B virus
<220> FEATURE:
<221> NAME/KEY: misc_feature
<223> OTHER INFORMATION: x67-76

<400> SEQUENCE: 109

Gly Pro Cys Ala Leu Arg Phe Thr Ser Ala
1 5 10

<210> SEQ ID NO 110
<211> LENGTH: 9
<212> TYPE: PRT
<213> ORGANISM: Hepatitis B virus
<220> FEATURE:
<221> NAME/KEY: misc_feature
<223> OTHER INFORMATION: x75-83

<400> SEQUENCE: 110

Ser Ala Arg Arg Met Glu Thr Thr Val
1 5

<210> SEQ ID NO 111
<211> LENGTH: 9
<212> TYPE: PRT
<213> ORGANISM: Hepatitis B virus
<220> FEATURE:
<221> NAME/KEY: misc_feature
<223> OTHER INFORMATION: x134-142

<400> SEQUENCE: 111

Leu Gly Gly Cys Arg His Lys Leu Val 1 5

<210> SEQ ID NO 112
<211> LENGTH: 10
<212> TYPE: PRT
<213> ORGANISM: Hepatitis B virus
<220> FEATURE:
<221> NAME/KEY: misc_feature
<223> OTHER INFORMATION: p508-517

<400> SEQUENCE: 112

Ile Ile Leu Gly Phe Arg Lys Ile Pro Met
1 5 10

<210> SEQ ID NO 113
<211> LENGTH: 9
<212> TYPE: PRT
<213> ORGANISM: Hepatitis B virus
<220> FEATURE:
<221> NAME/KEY: misc_feature
<223> OTHER INFORMATION: p482-490

<400> SEQUENCE: 113

Cys Ser Arg Asn Leu Tyr Val Ser Leu
1 5

<210> SEQ ID NO 114
<211> LENGTH: 9
<212> TYPE: PRT
<213> ORGANISM: Influenza A virus
<220> FEATURE:
<221> NAME/KEY: misc_feature
<223> OTHER INFORMATION: NP 44-52

<400> SEQUENCE: 114

Cys Thr Glu Leu Lys Leu Ser Asp Tyr
1 5

<210> SEQ ID NO 115
<211> LENGTH: 9
<212> TYPE: PRT
<213> ORGANISM: Respiratory syncytial virus
<220> FEATURE:
<221> NAME/KEY: misc_feature
<223> OTHER INFORMATION: NP 306-314

<400> SEQUENCE: 115

Asn Pro Lys Ala Ser Leu Leu Ser Leu
1 5

<210> SEQ ID NO 116
<211> LENGTH: 9
<212> TYPE: PRT
<213> ORGANISM: Cytomegalovirus
<220> FEATURE:
<221> NAME/KEY: misc_feature
<223> OTHER INFORMATION: pp65 495-503

<400> SEQUENCE: 116

Asn Leu Val Pro Met Val Ala Thr Val
1 5

<210> SEQ ID NO 117
<211> LENGTH: 9
<212> TYPE: PRT
<213> ORGANISM: Epstein Barr virus
<220> FEATURE:
<221> NAME/KEY: misc_feature

<223> OTHER INFORMATION: 416-424

<400> SEQUENCE: 117

Ile Val Thr Asp Phe Ser Val Ile Lys
1 5

<210> SEQ ID NO 118
<211> LENGTH: 9
<212> TYPE: PRT
<213> ORGANISM: Homo sapiens
<220> FEATURE:
<221> NAME/KEY: misc_feature
<223> OTHER INFORMATION: gp100 614-622

<400> SEQUENCE: 118

Leu Ile Tyr Arg Arg Arg Leu Met Lys
1 5

<210> SEQ ID NO 119
<211> LENGTH: 9
<212> TYPE: PRT
<213> ORGANISM: Homo sapiens
<220> FEATURE:
<221> NAME/KEY: misc_feature
<223> OTHER INFORMATION: GPR143 126-134

<400> SEQUENCE: 119

Leu Tyr Ser Ala Cys Phe Trp Trp Leu
1 5

<210> SEQ ID NO 120
<211> LENGTH: 9
<212> TYPE: PRT
<213> ORGANISM: Influenza A virus
<220> FEATURE:
<221> NAME/KEY: misc_feature
<223> OTHER INFORMATION: NP 380-388

<400> SEQUENCE: 120

Glu Leu Arg Ser Arg Tyr Trp Ala Ile
1 5

<210> SEQ ID NO 121
<211> LENGTH: 27
<212> TYPE: PRT
<213> ORGANISM: Hepatitis B virus

<400> SEQUENCE: 121

Lys Leu His Leu Tyr Ser His Pro Ile Ile Leu Gly Phe Arg Lys Ile
1 5 10 15

Pro Met Gly Val Gly Leu Ser Pro Phe Leu Leu
20 25

<210> SEQ ID NO 122
<211> LENGTH: 31
<212> TYPE: PRT
<213> ORGANISM: Hepatitis B virus

<400> SEQUENCE: 122

Gly Leu Leu Gly Phe Ala Ala Pro Phe Thr Gln Cys Gly Tyr Pro Ala
1 5 10 15

Leu Met Pro Leu Tyr Ala Cys Ile Gln Ala Lys Gln Ala Phe Thr
20 25 30

<210> SEQ ID NO 123

-continued

```
<211> LENGTH: 29
<212> TYPE: PRT
<213> ORGANISM: Hepatitis B virus

<400> SEQUENCE: 123

Ala Arg Gln Arg Pro Gly Leu Cys Gln Val Phe Ala Asp Ala Thr Pro
1               5                   10                  15

Thr Gly Trp Gly Leu Ala Ile Gly His Gln Arg Met Arg
            20                  25
```